United States Patent
Mizuki et al.

(10) Patent No.: US 9,318,709 B2
(45) Date of Patent: *Apr. 19, 2016

(54) MATERIAL FOR ORGANIC ELECTROLUMINESCENCE DEVICE, AND ORGANIC ELECTROLUMINESCENCE DEVICE USING THE SAME

(71) Applicant: IDEMITSU KOSAN CO., LTD., Chiyoda-ku (JP)

(72) Inventors: Yumiko Mizuki, Sodegaura (JP); Nobuhiro Yabunouchi, Sodegaura (JP); Tetsuya Inoue, Sodegaura (JP); Kumiko Hibino, Sodegaura (JP); Kazuki Nishimura, Sodegaura (JP)

(73) Assignee: IDEMITSU KOSAN CO., LTD., Chiyoda-ku (JP)

(*) Notice: Subject to any disclaimer, the term of this patent is extended or adjusted under 35 U.S.C. 154(b) by 371 days.

This patent is subject to a terminal disclaimer.

(21) Appl. No.: 13/900,939

(22) Filed: May 23, 2013

(65) Prior Publication Data

US 2014/0001451 A1 Jan. 2, 2014

Related U.S. Application Data

(60) Provisional application No. 61/651,271, filed on May 24, 2012.

(30) Foreign Application Priority Data

May 24, 2012 (JP) ................................. 2012-118854

(51) Int. Cl.
*H01L 51/50* (2006.01)
*H01L 51/00* (2006.01)
(Continued)

(52) U.S. Cl.
CPC .......... *H01L 51/0067* (2013.01); *C07D 403/04* (2013.01); *C09B 57/00* (2013.01);
(Continued)

(58) Field of Classification Search
None
See application file for complete search history.

(56) References Cited

U.S. PATENT DOCUMENTS

2004/0086745 A1 5/2004 Iwakuma et al.
2005/0127823 A1 6/2005 Iwakuma et al.
(Continued)

FOREIGN PATENT DOCUMENTS

KR 10-2012-0092908 A 3/2005
WO WO 03/078541 A1 9/2003
(Continued)

OTHER PUBLICATIONS

U.S. Appl. No. 13/900,939, filed May 23, 2013, Mizuki, et al.
(Continued)

*Primary Examiner* — Gregory Clark
(74) *Attorney, Agent, or Firm* — Oblon, McClelland, Maier & Neustadt, L.L.P.

(57) ABSTRACT

A material for an organic electroluminescence device represented by the following formula (I):

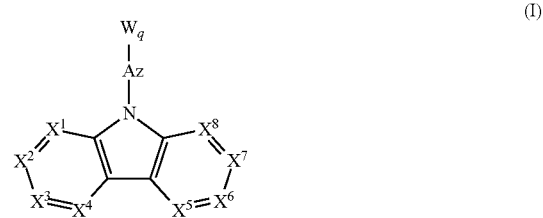

wherein $X^1$ to $X^8$ are a nitrogen atom, CH, CHal or $CR^a$; Az is a nitrogen-containing six-membered ring or a fused polycyclic group including a nitrogen-containing six-membered ring; W is an aromatic hydrocarbon group having 6 to 30 ring carbon atoms which is substituted by at least one cyano group or a heterocyclic group having 5 to 30 ring atoms which is substituted by at least one cyano group.

17 Claims, 1 Drawing Sheet

(51) Int. Cl.
*C07D 403/04* (2006.01)
*C09K 11/06* (2006.01)
*C09B 57/00* (2006.01)

(52) U.S. Cl.
CPC ........... *C09K 11/06* (2013.01); *H01L 51/0072* (2013.01); *C09K 2211/1007* (2013.01); *C09K 2211/1011* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01)

(56) References Cited

U.S. PATENT DOCUMENTS

| | | |
|---|---|---|
| 2005/0249976 A1 | 11/2005 | Iwakuma et al. |
| 2008/0145705 A1 | 6/2008 | Narihiro et al. |
| 2010/0230660 A1 | 9/2010 | Yokoyama et al. |
| 2010/0308322 A1* | 12/2010 | Yokoyama et al. ............. 257/40 |
| 2011/0309338 A1* | 12/2011 | Iwakuma ............. C07D 401/04 257/40 |
| 2012/0126221 A1* | 5/2012 | Kitamura et al. ................ 257/40 |
| 2012/0235129 A1 | 9/2012 | Iwakuma et al. |
| 2012/0298969 A1 | 11/2012 | Yokoyama et al. |
| 2012/0298975 A1 | 11/2012 | Iwakuma et al. |
| 2012/0319099 A1 | 12/2012 | Iwakuma et al. |
| 2013/0214258 A1 | 8/2013 | Mizuki et al. |

FOREIGN PATENT DOCUMENTS

| | | |
|---|---|---|
| WO | WO 03/080760 A1 | 10/2003 |
| WO | WO 2005/022961 A1 | 3/2005 |
| WO | WO 2008/020611 A1 | 2/2008 |
| WO | WO 2009/102016 A1 | 8/2009 |

OTHER PUBLICATIONS

U.S. Appl. No. 13/778,629, filed Feb. 27, 2013, Mizuki, et al.
International Search Report issued Aug. 6, 2013 in PCT/JP2013/003264 with English Translation of Category of Cited Documents.

* cited by examiner

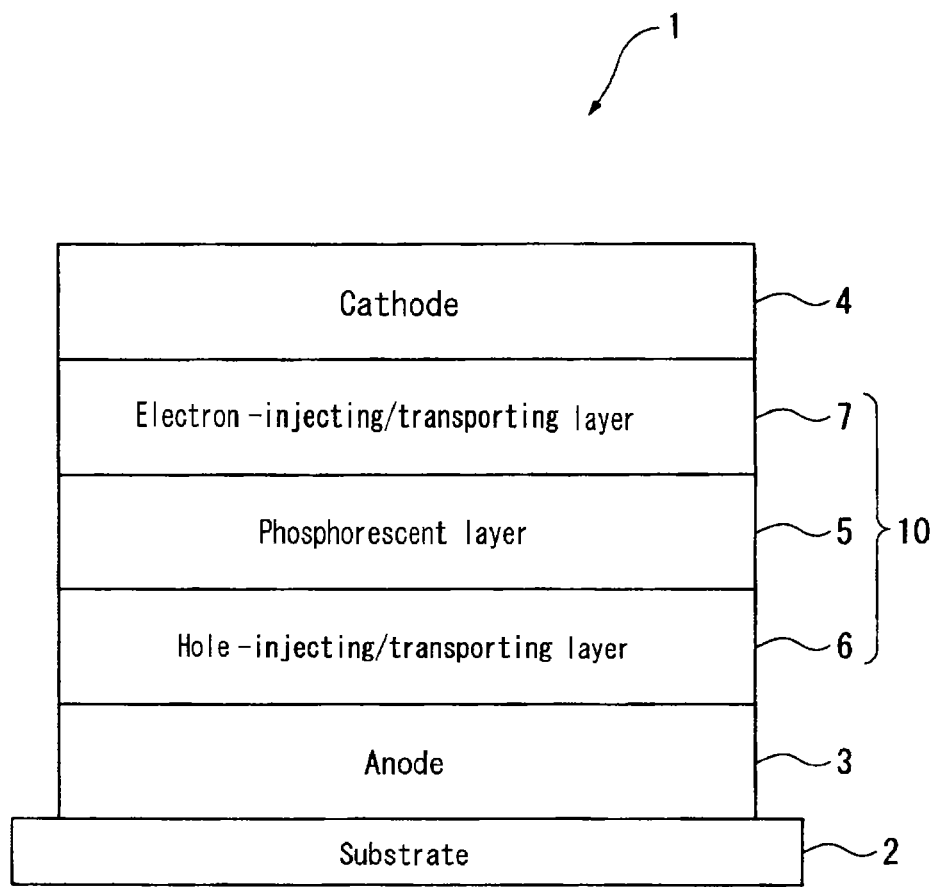

MATERIAL FOR ORGANIC ELECTROLUMINESCENCE DEVICE, AND ORGANIC ELECTROLUMINESCENCE DEVICE USING THE SAME

TECHNICAL FIELD

The invention relates to a material for an organic electroluminescence device, and an organic electroluminescence device using the same.

BACKGROUND ART

When a voltage is applied to an organic electroluminescence device (also hereinafter referred to as an organic EL device), holes and electrons are injected into an emitting layer from an anode and a cathode, respectively. In the emitting layer, the injected holes and electrons are recombined to form excitons. At this time, according to electron spins statistics, singlet excitons and triplet excitons are generated in a rate of 25%:75%. The emitting type is classified into two groups, i.e. fluorescent type and phosphorescent type, according to the emitting system. In the case of fluorescent type, due to using the emitting by singlet excitons, the internal quantum efficiency is regarded as having a limitation of 25%. On the other hand, in the case of phosphorescent type, emission by triplet excitons is used. As a result, it is known that if the intersystem crossing from singlet excitons occurs efficiently, the internal quantum efficiency can be increased to 100%.

Traditionally, for an organic EL device, suitable device designing has been made depending on the emitting mechanism, i.e. fluorescent type emission or phosphorescence type emission. In particular, as for a phosphorescent organic EL device, it is known that a high-performance device cannot be obtained by simple application of the technology of a fluorescent device due to its emission properties. The reason therefor is generally assumed to be as follows.

Since phosphorescent emission is emission utilizing triplet excitons, the energy gap of a compound used in the emitting layer must be large. The reason therefor is that, the singlet energy (i.e. a difference in energy between the lowest excited singlet state and the ground state) of a certain compound is normally larger than the triplet energy (i.e. a difference in energy between the lowest excited triplet energy state and the ground state) of the compound.

Therefore, in order to efficiently confine the triplet energy of the phosphorescent dopant material in the device, it is required to use a host material having a triplet energy larger than the triplet energy of the phosphorescent dopant material. Further, when an electron-transporting layer and a hole-transporting layer are provided in adjacent to the emitting layer, a compound having a triplet energy larger than that of the phosphorescent dopant material must be used in the electron-transporting layer and the hole-transporting layer. In this way, based on the conventional device design concept, as compared with a compound used in a fluorescent organic EL device, a compound having a further larger energy gap is used in a phosphorescent organic EL device, whereby a driving voltage in the entire organic EL device is increased.

Moreover, hydrocarbon-based compounds having high oxidative resistance and reductive resistance, which are useful for fluorescent devices, have a wide broadening of pi-cloud, and thus have a small energy gap. Hence, for a phosphorescent organic EL device, such hydrocarbon-based compounds can hardly be selected, and organic compounds containing hetero atoms such as oxygen or nitrogen tend to be selected. As a result, a phosphorescent organic EL device has a disadvantage of a shorter life time as compared with a fluorescent organic EL device.

In addition, the relaxation rate of triplet excitons of phosphorescent dopant materials is much longer than that of singlet excitons. This influences the device performance. That is, the emission from singlet excitons has a rapid relaxation rate resulting in emission, and thus diffusion of excitons into neighboring layers of the emitting layer (hole-transporting layer and electron-transporting layer, for example) hardly occurs, whereby efficient emitting can be expected. On the other hand, emission from triplet excitons is slowly relaxed due to the spin-forbidden principle, and thus diffusion of excitons into neighboring layers occurs easily. As a result, thermal energy deactivation occurs from other than the specific phosphorescent emitting compounds. That is, as compared with fluorescent organic EL device, it is more important to control the region where electrons and holes are recombined.

For the reasons mentioned above, in order to obtain a high-performance phosphorescent organic EL device, it is required to select different materials from those used in a fluorescent organic EL device and to design differently from the fluorescent organic EL device.

As such an organic EL material, traditionally, carbazole derivatives, which are known for their high triplet energy and as a main skeleton of a hole-transporting material, have been used as a useful phosphorescent host material.

Patent Document 1 discloses that a compound containing a carbazole skeleton and a nitrogen-containing heterocyclic group in the same molecule is used as an organic EL device material. The compound is molecularly designed such that carrier transporting is balanced, by introducing an electron-deficient nitrogen-containing heterocyclic group to the hole-transporting carbazole skeleton.

However, the life of an organic EL device is required to be further improved, and it is desired to develop an organic EL device material capable of realizing a more long life time.

RELATED ART DOCUMENTS

Patent Documents

[Patent Document 1] WO2003/080760

SUMMARY OF THE INVENTION

An object of the invention is to provide an organic electroluminescence device capable of obtaining a long-life phosphorescent emission and a material for an organic electroluminescence device which can realize it.

According to the invention, the following aromatic heterocyclic derivative, material for an organic electroluminescence device, material solution for an organic electroluminescence device and organic electroluminescence device using the same are provided.

1. A material for an organic electroluminescence device represented by the following formula (I):

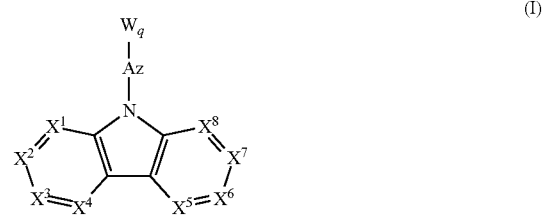

wherein in the formula (I),

X$^1$ to X$^8$ are independently a nitrogen atom, CH, CHal or CR$^a$;

Hals are independently a halogen atom;

R$^a$s are independently a substituted or unsubstituted aromatic hydrocarbon group having 6 to 30 carbon atoms that form a ring (hereinafter referred to as "ring carbon atoms"), a substituted or unsubstituted heterocyclic group having 5 to 30 atoms that form a ring (hereinafter referred to as "ring atoms"), a substituted or unsubstituted alkyl group having 1 to 30 carbon atoms, a substituted or unsubstituted silyl group or a cyano group;

when plural Hals or plural R$^a$s are present, the plural Hals or the R$^a$s may be the same or different;

when two adjacent groups of X$^1$ to X$^5$ are CR$^a$, R$^a$s in the adjacent CR$^a$s may be bonded to each other to form a ring;

Az is a substituted or unsubstituted nitrogen-containing six-membered ring, or a substituted or unsubstituted fused polycyclic group which contains a nitrogen-containing six-membered ring;

q is an integer of 1 to 4;

W is an aromatic hydrocarbon group having 6 to 30 ring carbon atoms which is substituted by at least one cyano group and may comprise a substituent that is not a cyano group, or an heterocyclic group having 5 to 30 ring atoms which is substituted by at least one cyano group and may comprise a substituent that is not a cyano group; and, when plural Ws are present, the plural Ws may be the same or deferent;

provided that the substituted or unsubstituted heterocyclic group having 5 to 30 ring atoms and the heterocyclic group having 5 to 30 ring atoms which is substituted by at least one cyano group and may comprise a substituent that is not a cyano group, are not a group represented by the following formula (A), and further, the substituent of each of the above groups does not include the group represented by the following formula (A);

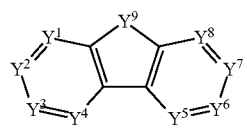

(A)

wherein in the formula (A),

Y$^1$ to Y$^8$ are the same as X$^1$ to X$^8$ in the formula (I), or a carbon atom which forms a single bond;

Y$^9$ is NH, NR$^c$ or a nitrogen atom which forms a single bond; and,

R$^c$ is a substituted or unsubstituted aromatic hydrocarbon group having 6 to 30 ring carbon atoms, a substituted or unsubstituted heterocyclic group having 5 to 30 ring atoms or a substituted or unsubstituted alkyl group having 1 to 30 carbon atoms.

2. The material for an organic electroluminescence device according to 1, which is represented by the following formula (I-2):

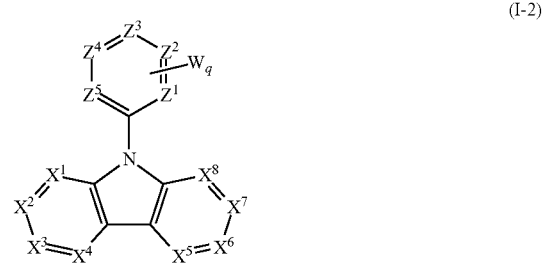

(I-2)

wherein in the formula (I-2),

X$^1$ to X$^8$, W and q are as defined in the formula (I);

Z$^1$ to Z$^5$ are independently a nitrogen atom, a carbon atom which bonds to W, CH, CHal or CR$^b$, and at least one of Z$^1$ to Z$^5$ is a nitrogen atom;

Hals are independently a halogen atom;

R$^b$s are independently a substituted or unsubstituted aromatic hydrocarbon group having 6 to 30 ring carbon atoms, a substituted or unsubstituted heterocyclic group having 5 to 30 ring atoms or a substituted or unsubstituted alkyl group having 1 to 30 carbon atoms;

when plural Hals or plural R$^b$s are present, the plural Hals or the plural R$^b$s may be the same or different; and, when two adjacent groups of Z$^1$ to Z$^5$ are CR$^b$, R$^b$s in the adjacent CR$^b$s may be bonded to each other to form a ring;

provide that the substituted or unsubstituted heterocyclic group having 5 to 30 ring atoms in the R$^b$ is not a group represented by the following formula (A), and further, the substituent of each of the above groups does not include the group represented by the following formula (A).

3. The material for an organic electroluminescence device according to 1, wherein the Az is a substituted or unsubstituted nitrogen-containing six-membered ring having 1 to 3 nitrogen atoms, or a substituted or unsubstituted fused polycyclic group which contains a nitrogen-containing six-membered ring.

4. The material for an organic electroluminescence device according to 2, wherein 1 to 3 of the Z$^1$ to Z$^5$ is a nitrogen atom.

5. The material for an organic electroluminescence device according to 1, wherein the Az is a ring group selected from the group consisting of a substituted or unsubstituted pyrimidine ring, a substituted or unsubstituted pyridine ring, a substituted or unsubstituted triazine ring and a substituted or unsubstituted quinazoline ring.

6. The material for an organic electroluminescence device according to any of 1 to 5, wherein the W is a cyano-substituted phenyl group, a cyano-substituted biphenyl group, a cyano-substituted 9,9-diphenylfluorenyl group, a cyano-substituted 9,9'-spirobi[9H-fluorene]-2-yl group, a cyano-substituted 9,9-dimethylfluorenyl group, a cyano-substituted dibenzofuranyl group or a cyano-substituted dibenzothiophenyl group.

7. The material for an organic electroluminescence device according to any of 1 to 6, wherein the q is 1.

8. The material for an organic electroluminescence device according to claim any of 1 to 7, wherein at least one of the X$^3$ and X$^8$ is CR$^a$, and the R$^a$s are independently a substituted or unsubstituted aromatic hydrocarbon group having 6 to 30 ring carbon atoms or a substituted or unsubstituted heterocyclic group having 5 to 30 ring atoms.

9. The material for an organic electroluminescence device according to any of 1 to 8, wherein at least one of the X$^2$ and $X^7$ is $CR^a$, and the $R^a$s are independently a substituted or unsubstituted aromatic hydrocarbon group having 6 to 30 ring carbon atoms or a substituted or unsubstituted heterocyclic group having 5 to 30 ring atoms.

10. The material for an organic electroluminescence device according to any of 1 to 9, wherein the $R^a$ is selected from the group consisting of a substituted or unsubstituted phenyl group, a substituted or unsubstituted naphthyl group, a substituted or unsubstituted biphenyl group, a substituted or unsubstituted terphenyl group, a substituted or unsubstituted quaterphenyl group, a substituted or unsubstituted triphenylenyl group, a substituted or unsubstituted phenanthrenyl group, a substituted or unsubstituted fluorenyl group, a substituted or unsubstituted spirofluorenyl group, a substituted or unsubstituted 9,9-diphenylfluorenyl group, a substituted or unsubstituted 9,9'-spirobi[9H-fluorene]-2-yl group, a substituted or unsubstituted 9,9-dimethylfluorenyl group, a substituted or unsubstituted benzo[c]phenanthrenyl group, a substituted or unsubstituted benzo[a]triphenylenyl group, a substituted or unsubstituted naphtho[1,2-c]phenanthrenyl group, a substituted or unsubstituted naphtho[1,2-a]triphenylenyl group, a substituted or unsubstituted dibenzo[a,c]triphenylenyl group, a substituted or unsubstituted dibenzothiophene ring, a substituted or unsubstituted isoquinoline ring, a substituted or unsubstituted quinoxaline ring, a substituted or unsubstituted pyridine ring, a substituted or unsubstituted pyrazine ring, a substituted or unsubstituted pyrimidine ring, a substituted or unsubstituted pyridazine ring, a substituted or unsubstituted triazine ring, a substituted or unsubstituted quinoline ring, a substituted or unsubstituted dibenzofuran ring, a substituted or unsubstituted benzo[c]dibenzofuran ring, a substituted or unsubstituted alkyl group having 1 to 30 carbon atoms, a substituted or unsubstituted silyl group and a cyano group.

11. The material for an organic electroluminescence device according to any of 2 to 10, wherein the $Z^1$ to $Z^5$ that are not a carbon atom bonding to a nitrogen atom or W, are independently CH or $CR^b$, and the $R^b$ is selected from the group consisting of a substituted or unsubstituted phenyl group, a substituted or unsubstituted naphthyl group, a substituted or unsubstituted biphenyl group, a substituted or unsubstituted terphenyl group, a substituted or unsubstituted quaterphenyl group, a substituted or unsubstituted triphenylenyl group, a substituted or unsubstituted phenanthrenyl group, a substituted or unsubstituted fluorenyl group, a substituted or unsubstituted spirofluorenyl group, a substituted or unsubstituted 9,9-diphenylfluorenyl group, a substituted or unsubstituted 9,9'-spirobi[9H-fluorene]-2-yl group, a substituted or unsubstituted 9,9-dimethylfluorenyl group, a substituted or unsubstituted benzo[c]phenanthrenyl group, a substituted or unsubstituted benzo[a]triphenylenyl group, a substituted or unsubstituted naphtho[1,2-c]phenanthrenyl group, a substituted or unsubstituted naphtho[1,2-a]triphenylenyl group, a substituted or unsubstituted dibenzo[a,c]triphenylenyl group, a substituted or unsubstituted dibenzothiophene ring, a substituted or unsubstituted isoquinoline ring, a substituted or unsubstituted quinoxaline ring, a substituted or unsubstituted pyridine ring, a substituted or unsubstituted pyrazine ring, a substituted or unsubstituted pyrimidine ring, a substituted or unsubstituted pyridazine ring, a substituted or unsubstituted triazine ring, a substituted or unsubstituted quinoline ring, a substituted or unsubstituted dibenzofuran ring, a substituted or unsubstituted benzo[c]dibenzofuran ring and a substituted or unsubstituted alkyl group having 1 to 30 carbon atoms.

12. An organic electroluminescence device comprising:
an anode, a cathode, and
one or more organic thin film layers including an emitting layer between the cathode and the anode,
wherein at least one of the organic thin film layers comprises the material for an organic electroluminescence device according to any of 1 to 11.

13. The organic electroluminescence device according to 12, wherein the emitting layer comprises the material for an organic electroluminescence device.

14. The organic electroluminescence device according to 12 or 13, wherein the emitting layer comprises a phosphorescent material, and the phosphorescent material is an ortho-metalized complex of a metal atom selected from iridium (Ir), osmium (Os) and platinum (Pt).

According to the invention, an organic EL device capable of obtaining long-life phosphorescent emission and a material for an organic electroluminescence device which can realize it can be provided.

BRIEF DESCRIPTION OF THE DRAWINGS

FIG. 1 is a schematic cross-sectional view showing one example of the organic EL device of the invention.

(Material for Organic Electroluminescence Device)

The material for organic electroluminescence device of the invention (hereinafter, often abbreviated as "the material for an organic EL device of the invention") is a compound represented by the following formula (I).

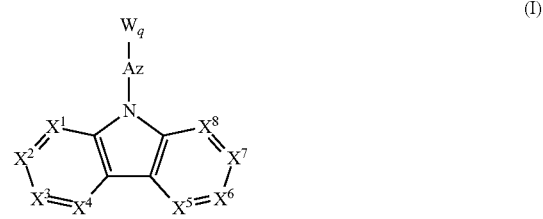

In the formula (I),
$X^1$ to $X^8$ are independently a nitrogen atom, CH, CHal or $CR^a$.

Hals are independently a halogen atom.

$R^a$s are independently a substituted or unsubstituted aromatic hydrocarbon group having 6 to 30 carbon atoms that form a ring (hereinafter referred to as the "ring carbon atoms"), a substituted or unsubstituted heterocyclic group having 5 to 30 atoms that form a ring (hereinafter referred to as the "ring atoms"), a substituted or unsubstituted alkyl group having 1 to 30 carbon atoms, a substituted or unsubstituted silyl group or a cyano group.

When plural Hals or plural $R^a$s are present, the plural Hals or the $R^a$s may be the same or different.

When two adjacent groups of $X^1$ to $X^5$ are $CR^a$, $R^a$s in the adjacent $CR^a$s may be bonded to each other to form a ring.

Az is a substituted or unsubstituted nitrogen-containing six-membered ring, or a substituted or unsubstituted fused polycyclic group which contains a nitrogen-containing six-membered ring.

q is an integer of 1 to 4.

W is an aromatic hydrocarbon group having 6 to 30 ring carbon atoms which is substituted by at least one cyano group and may comprise a substituent that is not a cyano group, or an heterocyclic group having 5 to 30 ring atoms which is substituted by at least one cyano group and may comprise a substituent that is not a cyano group.

When plural Ws are present, the plural Ws may be the same or deferent.

However, the substituted or unsubstituted heterocyclic group having 5 to 30 ring atoms and the heterocyclic group having 5 to 30 ring atoms which is substituted by at least one cyano group and may comprise a substituent that is not a cyano group, are not a group represented by the following formula (A), and further, the substituent of each of the above groups does not include the group represented by the following formula (A):

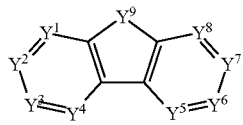

(A)

In the formula (A),
$Y^1$ to $Y^8$ are the same as $X^1$ to $X^8$ in the formula (I), or a carbon atom which forms a single bond. That is, $Y^1$ to $Y^8$ are independently a nitrogen atom, CH, CHal', $CR^{a'}$ or a carbon atom which forms a single bond.

Hal's are independently a halogen atom.

$R^{a'}$s are independently a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted silyl group or a cyano group.

Specific examples of Hal' and CRa' include the same as those of Hal and $CR^a$ described later.

$Y^9$ is NH, $NR^c$ or a nitrogen atom which forms a single bond.

$R^c$ is a substituted or unsubstituted aromatic hydrocarbon group having 6 to 30 ring carbon atoms, a substituted or unsubstituted heterocyclic group having 5 to 30 ring atoms or a substituted or unsubstituted alkyl group having 1 to 30 carbon atoms.

Here, in the above formula (A), if $Y^9$ is a nitrogen atom which forms a single bond, it corresponds to a group represented by the following formula (A-2) in the above formula (A):

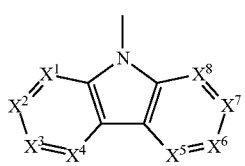

(A-2)

The material for an organic EL device of the invention comprises only one group represented by the above formula (A-2) in the above formula (I), and does not comprise groups represented by the above formula (A) that are not the group represented by the above formula (A-2) in the above formula (I). The same can be applied to the formula (I-2) described later as well.

Examples of the group represented by the formula (A) that is not contained in the material for an organic EL device of the invention include the group having an atomic bonding at any of positions of $Y^1$ to $Y^8$, in addition to the group represented by the above formula (A-2), that is the group having an atomic bonding at the position of $Y^9$.

The material for an organic EL device of the invention is preferably represented by the following formula (I-2):

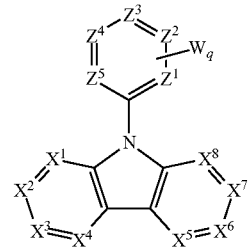

(I-2)

In the formula (I-2),
$X^1$ to $X^8$, W and q are as defined in the formula (I).
$Z^1$ to $Z^8$ are independently a nitrogen atom, a carbon atom which bonds to W, CH, CHal or $CR^b$, and at least one of $Z^1$ to $Z^5$ is a nitrogen atom.

Hals are independently a halogen atom.

$R^b$s are independently a substituted or unsubstituted aromatic hydrocarbon group having 6 to 30 ring carbon atoms, a substituted or unsubstituted heterocyclic group having 5 to 30 ring atoms or a substituted or unsubstituted alkyl group having 1 to 30 carbon atoms.

When plural Hals or plural $R^b$s are present, the plural Hals or the plural $R^b$s may be the same or different.

When two adjacent groups of $Z^1$ to $Z^5$ are $CR^b$, $R^b$s in the adjacent $CR^b$s may be bonded to each other to form a ring.

However, the substituted or unsubstituted heterocyclic group having 5 to 30 ring atoms in the $R^b$ is not a group represented by the following formula (A), and further, the substituent of each of the above groups does not include the group represented by the following formula (A).

Each group in the following formula (I) and (I-2) will be explained below.

As the aromatic hydrocarbon group having 6 to 30 ring carbon atoms (preferably 6 to 14 ring carbon atoms) in $R^a$, W, $R^b$ and $R^c$, a non-fused aromatic hydrocarbon group and a fused aromatic hydrocarbon group can be given. Specific Examples thereof include a phenyl group, a naphthyl group, a phenanthryl group, a biphenyl group, a terphenyl group, a quaterphenyl group, a fluoranthenyl group, a triphenylenyl group, a phenanthrenyl group, a fluorenyl group, a spirofluorenyl group, a 9,9-diphenylfluorenyl group, a 9,9'-spirobi[9H-fluorene]-2-yl group, a 9,9'-dimethylfluorenyl group, a benzo[a]triphenylenyl group, a naphtho[1,2-c]phenanthrenyl group, a naphtho[1,2-a]triphenylenyl group, a dibenzo[a,c]triphenylenyl group and a benzo[b]fluoranthenyl group. Of these, a phenyl group, a naphthyl group, a biphenyl group, a terphenyl group, a phenanthrenyl group, a triphenylenyl group, a fluorenyl group, a spirobifluorenyl group and a fluoranthenyl group are preferable.

As the heterocyclic group having 5 to 30 ring atoms (preferably 5 to 14 ring atoms) in $R^a$, W, $R^b$ and $R^c$, a non-fused heterocyclic group and a fused heterocyclic group can be given. However, the heterocyclic group having 5 to 30 ring atoms is not those as in the above formula (A).

More specifically, a pyrrol ring, a isoindole ring, a benzofuran ring, an isobenzofuran ring, a dibenzothiophene ring, an isoquinoline ring, a quinoxaline ring, a phenanthridine ring, a phenanthroline ring, a pyridine ring, a pyrazine ring, a pyrimidine ring, a pyridazine ring, a triazine ring, an indole ring, a quinoline ring, an acridine ring, a pyrrolidine ring, a dioxane ring, a piperidine ring, a morpholine ring, a piperazine ring, a furan ring, a thiophene ring, an oxazole ring, an oxadiazole ring, a benzoxazole ring, a thiazole ring, a thiadiazole ring, a benzothiazole ring, a triazole ring, an imidazole ring, a benzimidazole ring, a pyran ring, a dibenzofuran ring, a benzo[c]dibenzofuran ring and a group formed of derivatives thereof can be given. Of these, a dibenzofuran group, a dibenzothiophene ring and a group formed of derivatives thereof are preferable.

As the alkyl group having 1 to 30 carbon atoms (preferably 1 to 6 carbon atoms) in $R^a$, $R^b$ and $R^c$, a methyl group, an ethyl group, an n-propyl group, an isopropyl group, an n-butyl group, an s-butyl group, an isobutyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, a neopentyl group, a 1-methylpentyl group, a cyclopropyl group, a cyclobutyl group, a cyclopentyl group, a cyclohexyl group, a cyclooctyl, an adamanthyl group and the like can be given. Of these, a methyl group, an ethyl group, an n-propyl group, an isopropyl group, an n-butyl group, an s-butyl group, an isobutyl group, a t-butyl group, a cyclopentyl group and a cyclohexyl group are preferable.

As the substituted or unsubstituted silyl group in $R^a$, a trimethysilyl group, a triethylsilyl group, a tributylsilyl group, a dimethylethylsilyl group, a t-butyldimethylsilyl group, a vinyldimethylsilyl group, a propyldimethylsilyl group, a dimethylisopropylsilyl group, a dimethylpropylsilyl group, a dimethylbutylsilyl group, a dimethyltertbutylsilyl group, a dimethylisopropylsilyl group, a phenyldimethylsilyl group, a diphenylmethylsilyl group, a diphenyltertbutylsilyl group, a triphenylsilyl group and the like can be given. Of these, a trimethylsilyl group, a triethylsilyl group, a t-butyldimethylsilyl group a vinyldimethylsilyl group and a propyldimethylsilyl group are preferable.

As the halogen atom, fluorine, chlorine, bromine and iodine can be given, for example. Fluorine is preferable.

As the nitrogen-containing six-membered ring in Az, a pyrimidine ring, a pyridine ring, a triazine ring, a quinazoline ring and the like can be given. A pyrimidine ring is preferable.

As the fused polycyclic group which contains a nitrogen-containing six-membered ring in Az, a quinozoline ring and the like can be given.

As the arbitrary substituent referred to as by the above-mentioned "substituted or unsubstituted", a halogen atom (fluorine, chlorine, bromine, iodine), a cyano group, an alkyl group having 1 to 20 (preferably 1 to 6) carbon atoms, a cycloalkyl group having 3 to 20 (preferably 5 to 12) carbon atoms, an alkoxy group having 1 to 20 (preferably 1 to 5) carbon atoms, a haloalkyl group having 1 to 20 (preferably 1 to 5) carbon atoms, a haloalkoxy group having 1 to 20 (preferably 1 to 5) carbon atoms, an alkylsilyl group having 1 to 10 (preferably 1 to 5) carbon atoms, an aryl group (aromatic hydrocarbon group) having 6 to 30 (preferably 6 to 18) ring carbon atoms, an aryloxy group having 6 to 30 (preferably 6 to 18) ring carbon atoms, an arylsilyl group having 6 to 30 (preferably 6 to 18) carbon atoms, an aralkyl group having 7 to 30 (preferably 7 to 20) carbon atoms and a heteroaryl group (heterocyclic group) having 5 to 30 (preferably 5 to 18) ring atoms can be given. However, the heteroaryl group (heterocyclic group) includes no group represented by the above formula (A).

As the alkyl group, silyl group, aromatic hydrocarbon group and heterocyclic group which are given above as the arbitrary substituent, those mentioned above can be given.

As the cycloalkyl group, a group obtained by making the exemplified alkyl group having 3 or more carbon atoms into an aliphatic ring structure can be given.

As the haloalkyl group, a group obtained by replacing one or more hydrogen atom in the alkyl group by halogen atoms can be given. As the halogen atom, fluorine is preferable. In addition, a trifluoromethyl group, a 2,2-trifluoroethyl group and the like can be given.

As the alkoxy group, a methoxy group, an ethoxy group, a propoxy group, a pentyloxy group, a hexyloxy group and the like can be given.

As the haloalkoxy group, a group obtained by replacing one or more hydrogen atom in the alkoxy group by halogen atoms can be given. As the halogen atom, fluorine is preferable.

As the aryloxy group, a group obtained by replacing one hydrogen atom in a non-fused aromatic hydrocarbon group and fused aromatic hydrocarbon group by a —O— group can be given.

As the aralkyl group, a group obtained by replacing one hydrogen atom in a non-fused aromatic hydrocarbon group and fused aromatic hydrocarbon group by an alkyl group can be given.

Among the above-mentioned arbitrary substituents, fluorine, a cyano group, an alkyl group, a cycloalkyl group, an alkylsilyl group, an aryl group (aromatic hydrocarbon group), a heteroaryl group (cyclocyclic group) are particularly preferable. However, the heteroaryl group (cyclocyclic group) includes no group represented by the above formula (A).

Herein, the "a to b carbon atoms" in the expression "substituted or unsubstituted XX group having a to b carbon atoms" represents the number of carbons in the case that the XX group is unsubstituted, excluding the number of carbons as the substituents when the XX group is substituted. In the organic EL device material of the invention, the hydrogen atom includes isotopes having a different number of neutrons, i.e. light hydrogen (protium), deuterium and tritium.

As the Az substituted by W in the formula (I), the following groups can be given.

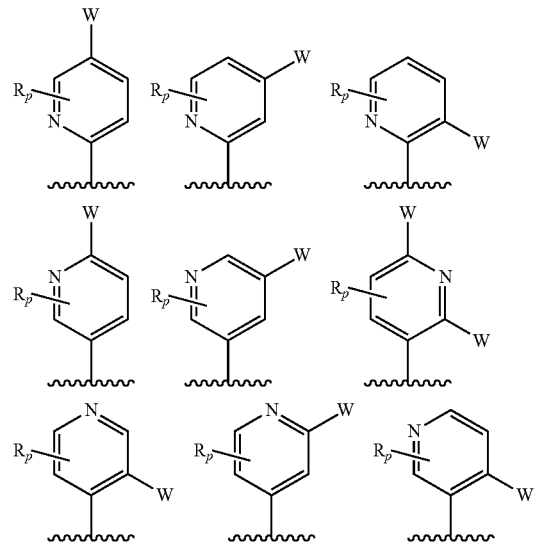

-continued

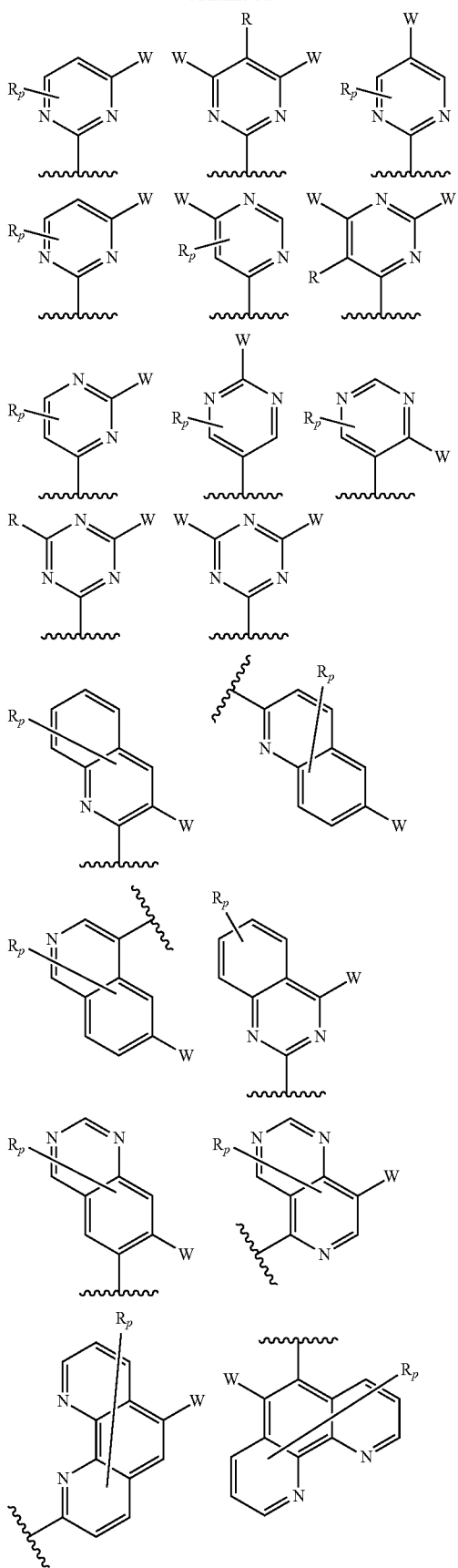

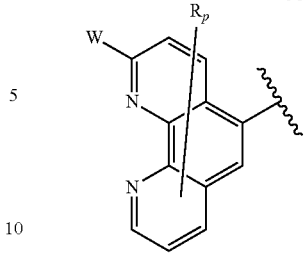

In the above formula, the wavy line represents the position to which the nitrogen atom of the carbazole group is bonded.

R is the group which is substituted in Az, and is independently a halogen atom, a substituted or unsubstituted aromatic hydrocarbon group having 6 to 30 ring carbon atoms, a substituted or unsubstituted heterocyclic group having 5 to 30 ring atoms or a substituted or unsubstituted alkyl group having 1 to 30 carbon atoms.

In the case of plural $R^5$, the plural $R^5$ may be the same as or different from each other.

p is an integer of 1 to 6.

W and q are as defined in the above formula (I).

Az is preferably a ring group selected from the group consisting of a substituted or unsubstituted pyrimidine ring, a substituted or unsubstituted pyridine ring, a substituted or unsubstituted triazine ring and a substituted or unsubstituted quinazoline ring, with a nitrogen-containing six-membered ring group being more preferable.

It is preferred that Az be a substituted or unsubstituted nitrogen-containing six-membered ring or a fused polycyclic group which contains a nitrogen-containing six-membered ring, each having 1 to 3 nitrogen atoms.

It is more preferred that Az be a group represented by the following formula (X). That is, the organic EL device material of the invention is preferably an organic device material represented by the above formula (I-2).

$$Z^4 \underset{Z^5}{\overset{Z^3}{=}} Z^2 \atop Z^1 \quad (X)$$

It is preferred that 1 to 3 of $Z^1$ to $Z^5$ be a nitrogen atom. It is particularly preferred that $Z^1$ and $Z^5$ be a nitrogen atom.

W is preferably an aromatic hydrocarbon group having 6 to 30 ring carbon atoms which has one or more (1 to 5, preferably 1 to 2, and more preferably 1) cyano groups as a substituent, or a heterocyclic group having 5 to 30 ring atoms which has one or more (1 to 5, preferably 1 to 2, and more preferably 1) cyano groups as a substituent. However, the aromatic hydrocarbon group having 6 to 30 ring carbon atoms and the heterocyclic group having 5 to 30 ring atoms as W may have a substituent in addition to the cyano group.

As the aromatic hydrocarbon group having 6 to 30 ring carbon atoms and the heterocyclic group having 5 to 30 ring atoms as W, a cyano group-substituted phenyl group, a cyano group-substituted biphenyl group, a cyano group-substituted naphthyl group, a cyano group-substituted phenanthryl group, a cyano group-substituted 9,9-diphenylfluorenyl group, a cyano group-substituted 9,9'-spirobi[9H-fluorene]-2-yl group, a cyano group-substituted 9,9-dimethylfluorenyl group, a cyano group-substituted dibenzofuranyl group, a cyano group-substituted dibenzothiophenyl, a cyano group-substituted triphenylenyl group, a cyano-substituted dibenzothiophenyl group, a cyano-substituted dibenzothiophenyl group, a cyano-substituted dibenzofuranyl group and the like can be given.

As W, a cyano group-substituted phenyl group, a cyano group-substituted biphenyl group, a cyano group-substituted 9,9-diphenylfluorenyl group, a cyano group-substituted 9,9'-spirobi[9H-fluorene]-2-yl group, a cyano group-substituted 9,9-dimethylfluorenyl group, a cyano group-substituted dibenzofuranyl group and a cyano group-substituted dibenzothiophenyl are preferable, with a cyano group-substituted phenyl group, a cyano group-substituted biphenyl group such a 4-cyanobiphenyl group, a 3-cyanobiphenyl group or a 2-cyanobiphenyl group, a cyano group-substituted 9,9-dimethylfluorenyl group, a cyano group-substituted 9,9'-spirobi[9H-fluorene]-2-yl group, a cyano group-substituted 9,9-dimethylfluorenyl group, a cyano group-substituted dibenzofuranyl group and a cyano group-substituted dibenzothiophenyl being more preferable.

Due to W being a cyano group-substituted phenyl group, a cyano group-substituted biphenyl group or a cyano group-substituted fluorenyl group, the triplet energy level tends to be higher as compared with the case where W itself is a cyano group. As a result, when the corresponding compound is contained in an emitting layer of an organic EL device, the luminous efficiency is preferably higher.

When the cyano group-substituted aromatic hydrocarbon group having 6 to 30 ring carbon atoms and the cyano group-substituted heterocyclic group having 5 to 30 ring atoms as W may have a substituent in addition to the cyano group, examples of the substituent include those exemplified in the arbitrary substituent in the above-mentioned "substituted or unsubstituted".

W is preferably a cyano-substituted phenyl group, a cyano-substituted biphenyl group, a cyano-substituted 9,9-diphenylfluorenyl group, a cyano-substituted 9,9'-spirobi[9H-fluorene]-2-yl group, a cyano-substituted 9,9-dimethylfluorenyl group, a cyano-substituted dibenzofuranyl group or a cyano-substituted dibenzothiophenyl group, with a cyano-substituted phenyl group and a cyano-substituted biphenyl group being particularly preferable.

q represents the number of W which is substituted in Az, and is preferably 1 or 2, with 1 being more preferable.

It is more preferred that at least one of $X^3$ and $X^6$ be $CR^a$, the $R^a$ being dependently a substituted or unsubstituted aromatic hydrocarbon group having 6 to 30 ring carbon atoms, or a substituted or unsubstituted heterocyclic group having 5 to 30 ring atoms. When at least one of $X^3$ and $X^6$ is $CR^a$, the stability of materials is more improved by introducing a substituted or unsubstituted aromatic hydrocarbon group having 6 to 30 ring carbon atoms or a substituted or unsubstituted heterocyclic group having ring atoms into the positions of $X^3$ and $X^6$ which have high activity in $X^1$ to $X^4$ and $X^5$ to $X^5$, respectively.

Also, it is more preferred that at least one of $X^2$ and $X^7$ be $CR^a$, the $R^a$ being dependently a substituted or unsubstituted aromatic hydrocarbon group having 6 to 30 ring carbon atoms, or a substituted or unsubstituted heterocyclic group having 5 to 30 ring atoms. When at least one of $X^2$ and $X^7$ is $CR^a$, the stability of materials is more improved due to the wide broadening pi-cloud.

Here, in the case above, it is further preferable that $R^a$ in $CR^a$ of $X^3$ and $X^6$, or $X^2$ and $X^7$ is an aromatic hydrocarbon group or a heterocyclic group and $X^1$ to $X^8$ excluding them is CH.

It is preferred that $R^a$ be selected from the group consisting of a substituted or unsubstituted phenyl group, a substituted or unsubstituted naphthyl group, a substituted or unsubstituted biphenyl group, a substituted or unsubstituted terphenyl group, a substituted or unsubstituted quaterphenyl group, a substituted or unsubstituted triphenylenyl group, a substituted or unsubstituted phenanthrenyl group, a substituted or unsubstituted fluorenyl group, a substituted or unsubstituted spirofluorenyl group, a substituted or unsubstituted 9,9-diphenylfluorenyl group, a substituted or unsubstituted 9,9'-spirobi[9H-fluorene]-2-yl group, a substituted or unsubstituted 9,9'-dimethylfluorenyl group, a substituted or unsubstituted benzo[c]phenanthrenyl group, a substituted or unsubstituted benzo[a]triphenylenyl group, a substituted or unsubstituted naphtho[1,2-c]phenanthrenyl group, a substituted or unsubstituted naphtha[1,2-a]triphenylenyl group, a substituted or unsubstituted dibenzo[a,c]triphenylenyl group, a substituted or unsubstituted debenzothiophene ring, a substituted or unsubstituted isoquinoline ring, a substituted or unsubstituted quinoxaline ring, a substituted or unsubstituted pyridine ring, a substituted or unsubstituted pyrazine ring, a substituted or unsubstituted pyrimidine ring, a substituted or unsubstituted pyridazine ring, a substituted or unsubstituted triazine ring, a substituted or unsubstituted quinoline ring, a substituted or unsubstituted dibenzofuran ring, a substituted or unsubstituted benzo[c]dibenzofuran ring, a substituted or unsubstituted alkyl group having 1 to 30 carbon atoms, a substituted or unsubstituted silyl group and a cyano group.

$Z^1$ to $Z^5$ which are not the carbon atoms bonding to the nitrogen atom or W are independently CH or $CR^b$. It is preferred that $R^b$ be selected from the group consisting of a substituted or unsubstituted phenyl group, a substituted or unsubstituted naphthyl group, a substituted or unsubstituted biphenyl group, a substituted or unsubstituted terphenyl group, a substituted or unsubstituted quaterphenyl group, a substituted or unsubstituted triphenylenyl group, a substituted or unsubstituted phenanthrenyl group, a substituted or unsubstituted fluorenyl group, a substituted or unsubstituted spirofluorenyl group, a substituted or unsubstituted 9,9-diphenylfluorenyl group, a substituted or unsubstituted 9,9'-spirobi[9H-fluorene]-2-yl group, a substituted or unsubstituted 9,9'-dimethylfluorenyl group, a substituted or unsubstituted benzo[c]phenanthrenyl group, a substituted or unsubstituted benzo[a]triphenylenyl group, a substituted or unsubstituted naphtho[1,2-c]phenanthrenyl group, a substituted or unsubstituted naphtha[1,2-a]triphenylenyl group, a substituted or unsubstituted dibenzo[a,c]triphenylenyl group, a substituted or unsubstituted debenzothiophene ring, a substituted or unsubstituted isoquinoline ring, a substituted or unsubstituted quinoxaline ring, a substituted or unsubstituted pyridine ring, a substituted or unsubstituted pyrazine ring, a substituted or unsubstituted pyrimidine ring, a substituted or unsubstituted pyridazine ring, a substituted or unsubstituted triazine ring, a substituted or unsubstituted quinoline ring, a substituted or unsubstituted dibenzofuran ring, a substituted or unsubstituted benzo[c]dibenzofuran ring and a substituted or unsubstituted alkyl group having 1 to 30 carbon atoms.

The organic EL device material of the invention is characterized that it has a carbazole ring or a azacarbazole ring (hereinafter collectively referred to as "carbazole skeleton") as a hole-injecting and/or transporting unit and a cyano group-substituted heterocyclic ring (nitrogen-containing heterocyclic ring Az) as an electron-injecting and/or transporting unit, and the structure in which the $9^{th}$ nitrogen atom in the carbazole skeleton as the hole-injecting and/or transporting unit and the main skeleton in the electron-injecting and/or transporting unit (carbon atom in the nitrogen-containing heterocyclic ring) are bonded directly.

When comparing the case where the 9$^{th}$ nitrogen atom in the carbazole skeleton and the carbon atom in the nitrogen-containing heterocyclic ring Az are bonded directly with the case where these are bonded through a linking group (aromatic ring, for example), for the twisting of the bond on the 9$^{th}$ nitrogen atom in the carbazole skeleton, the degree thereof in the case where Az is bonded directly is smaller. Hence, it is thought to be difficult to dissociate the bond on the 9$^{th}$ nitrogen atom in the carbazole skeleton. Therefore, the direct bond to Az is thought to result in more stable as a compound. The stability is assumed to contribute to a prolonged life of the organic EL device material of the invention.

In the organic EL device material of the invention, the electron-transporting unit represented by -Az-Wq of a nitrogen-containing six-membered ring or fused polycyclic ring containing a nitrogen-containing six-membered ring which contains a cyano group is bonded to a hole-transporting carbazole skeleton, the electron-transporting unit being obtained by introducing a cyano group-substituted aromatic hydrocarbon group or a cyano group-substituted heterocyclic group into the nitrogen-containing six-membered ring or fused polycyclic ring containing a nitrogen-containing six-membered ring. As a result, the carrier balance in a molecule becomes good, whereby an organic EL device using the material has a prolonged life.

Further, in the organic EL device material of the invention, the carrier balance in a molecule becomes favorable, without mutually affecting adversely the properties of the hole-injecting and/or transporting carbazole skeleton and the electron-injecting and/or transporting group having a cyano group, whereby an organic EL device using the material has prolonged life.

The method for producing the organic EL device material of the invention is not particularly restricted. The organic EL device material of the invention can be produced using a known method. For example, it can be produced by the coupling reaction of a carbazole derivative and an aromatic halogen compound using a copper catalyst described in Tetrahedron 40 (1984) 1435 to 1456 or a palladium catalyst described in Journal of American Chemical Society 123 (2001) 7727 to 7729.

Specific examples of the organic EL device material of the invention will be described below, but not limited to the following compounds.

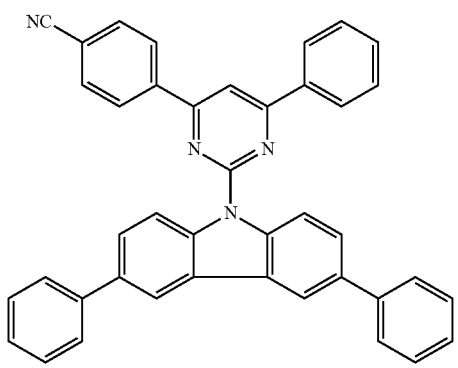

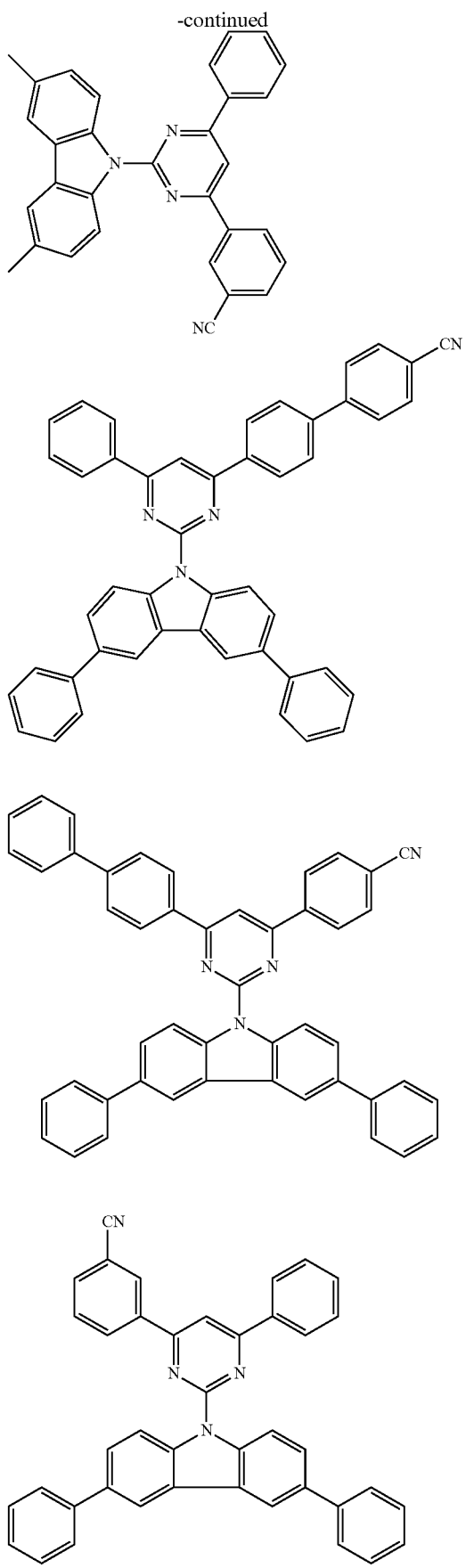

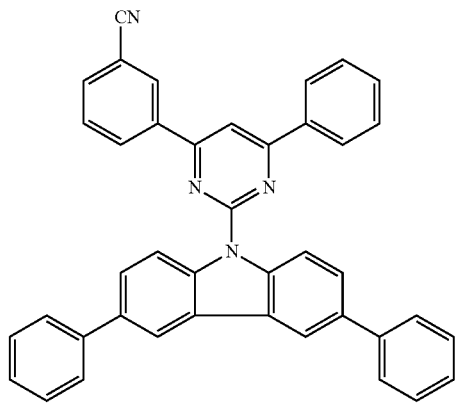

-continued
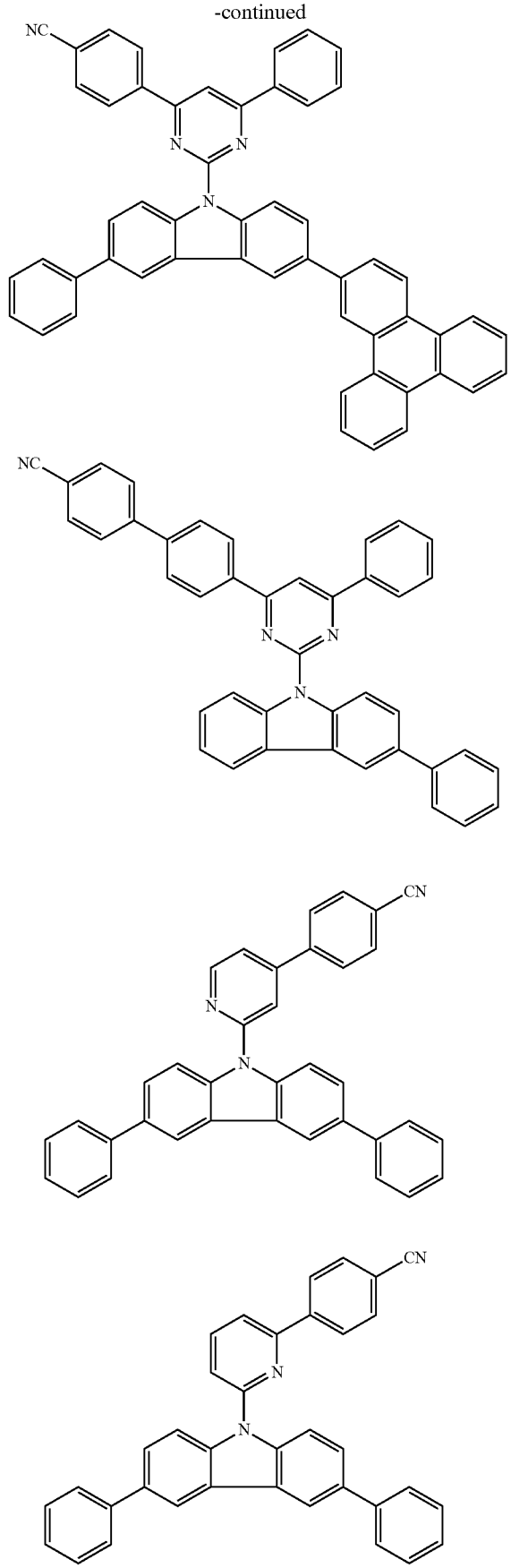
-continued
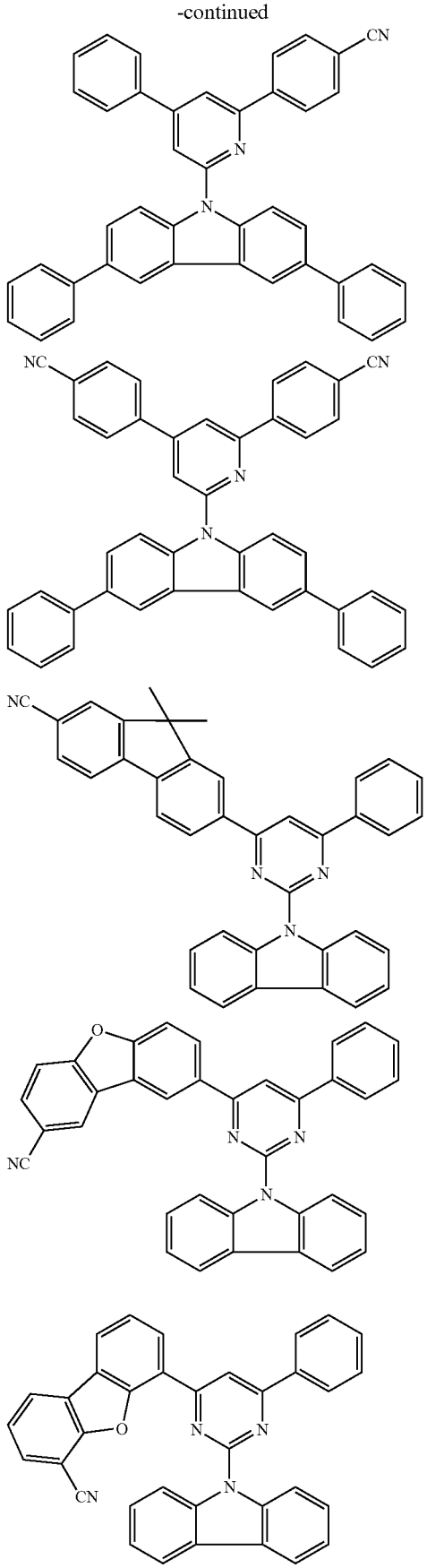

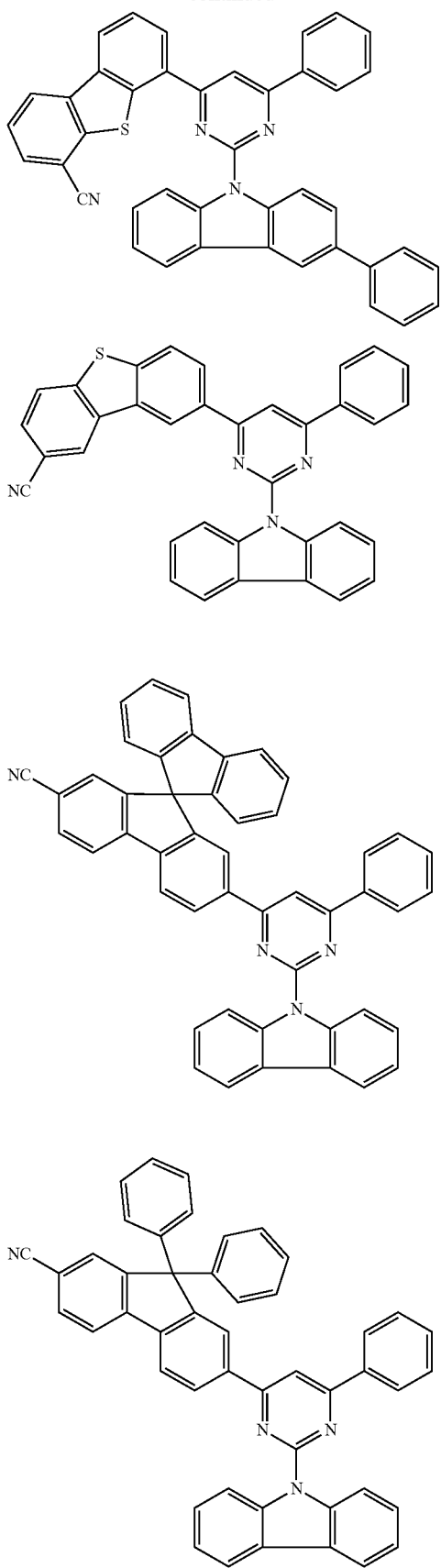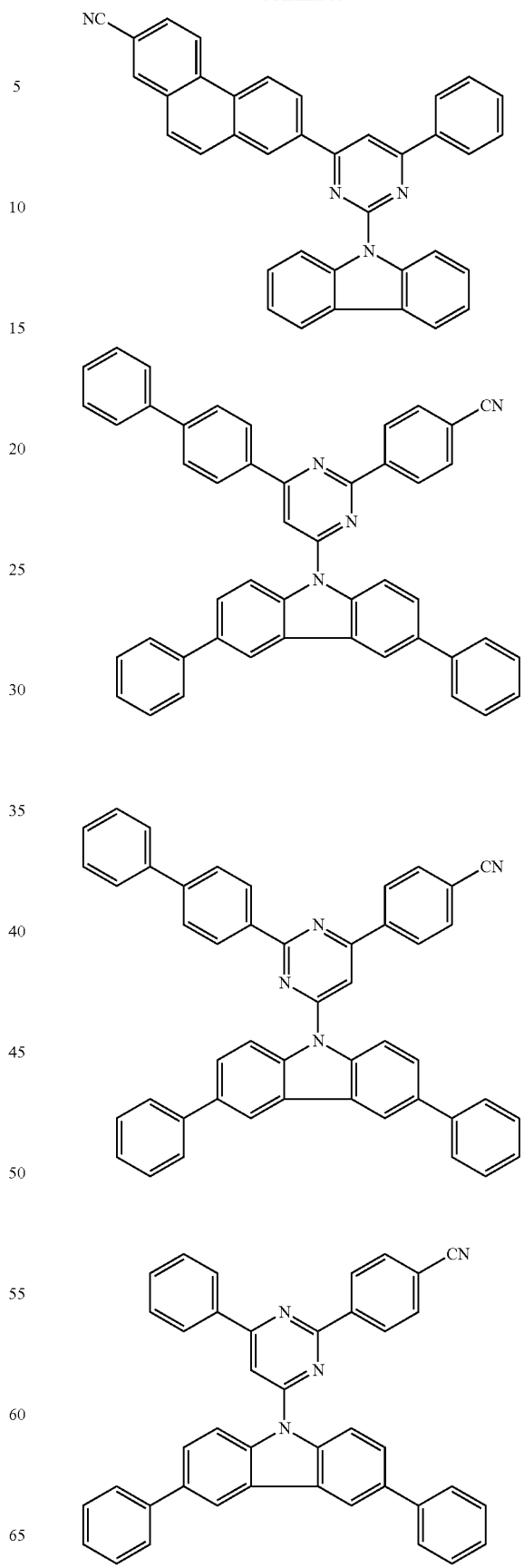

21
-continued
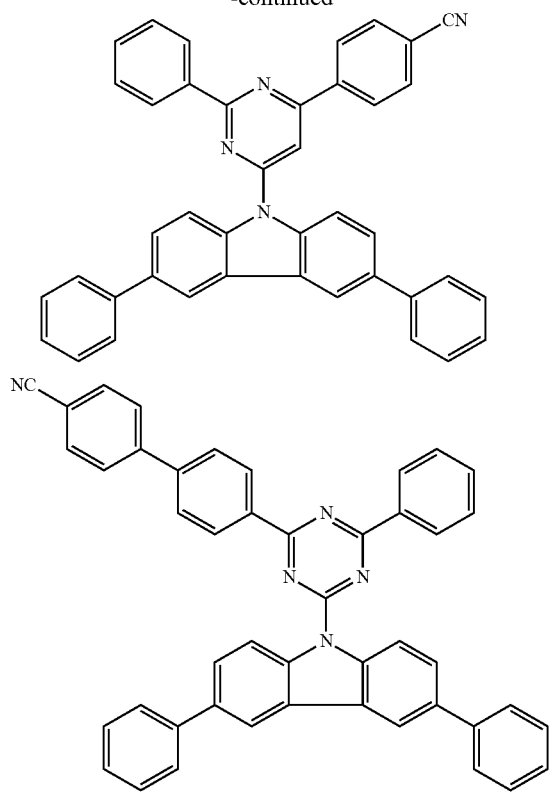
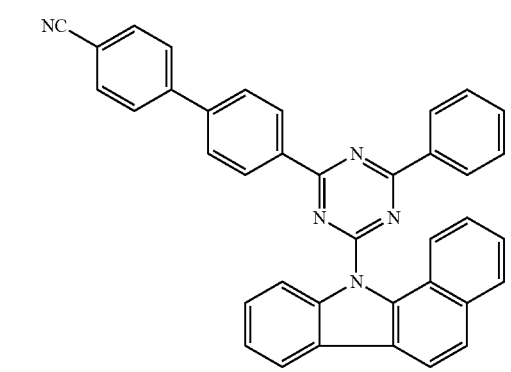
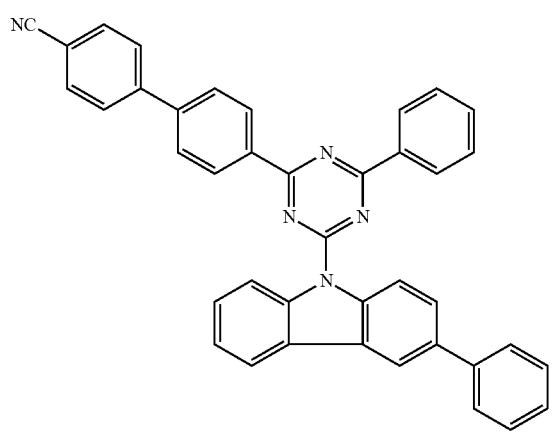
22
-continued
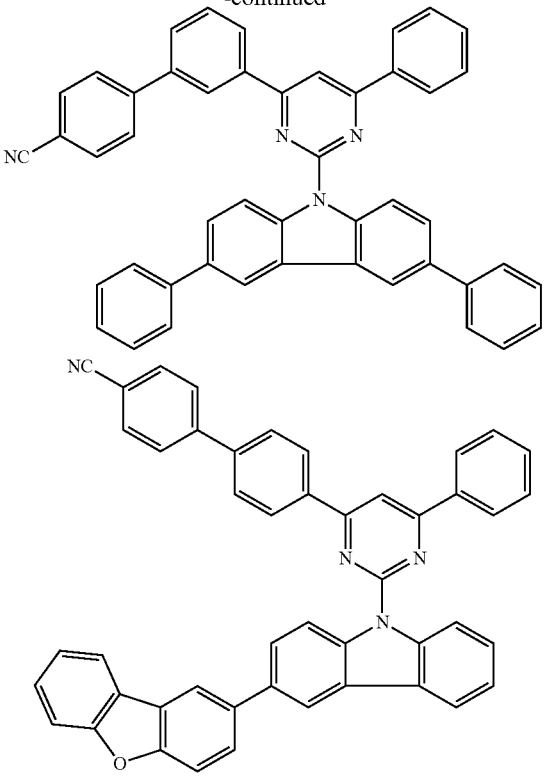
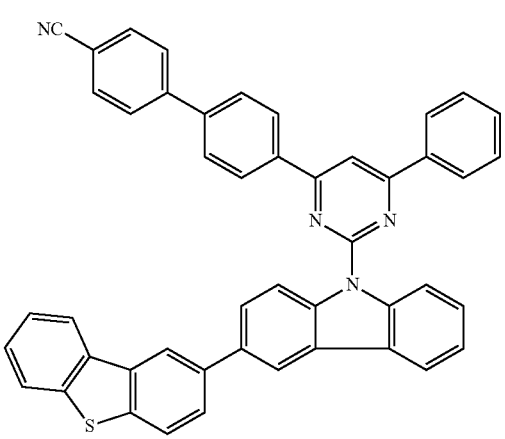
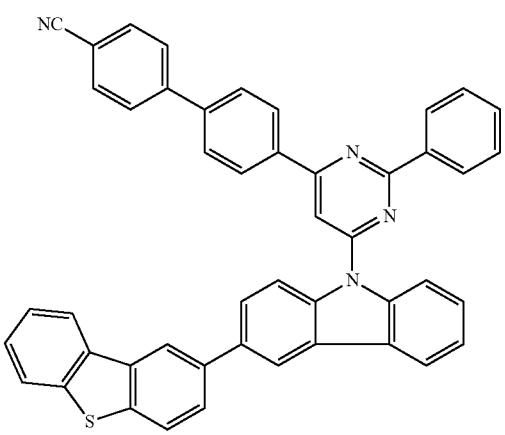

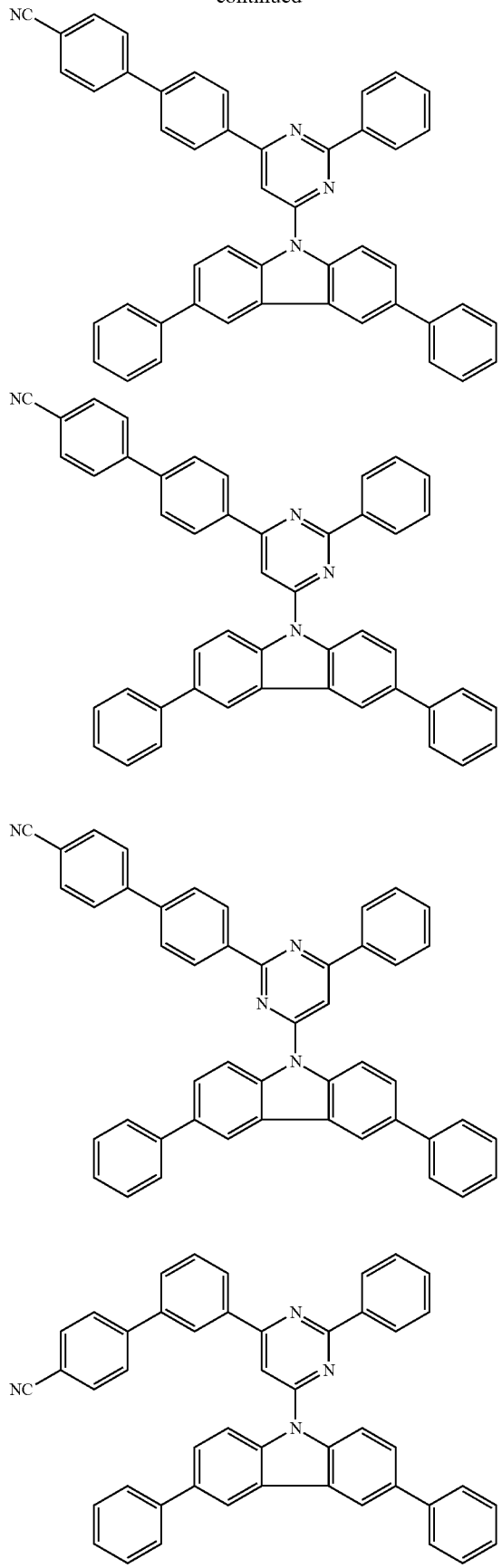
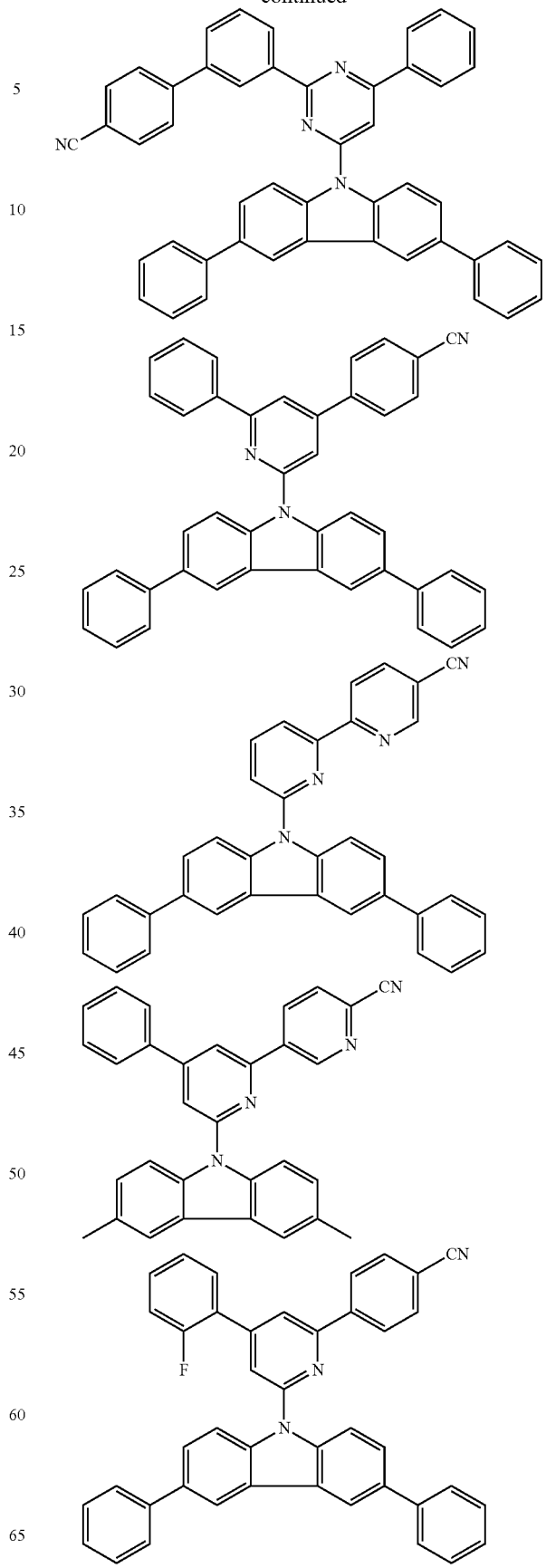

25
-continued
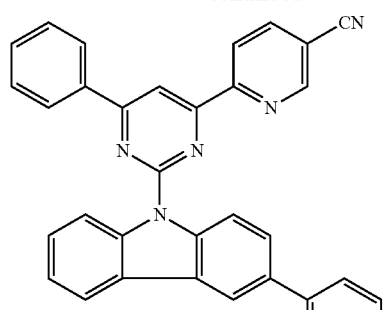
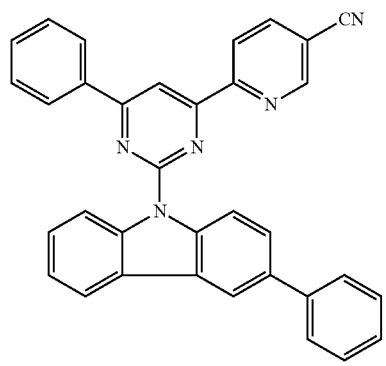
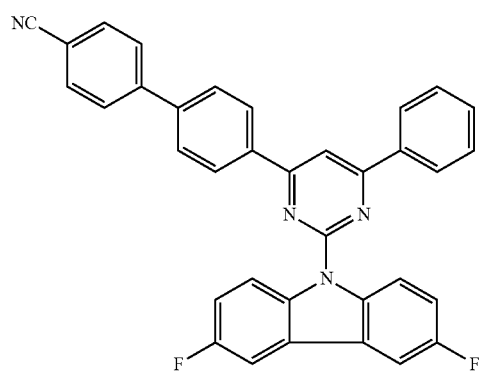
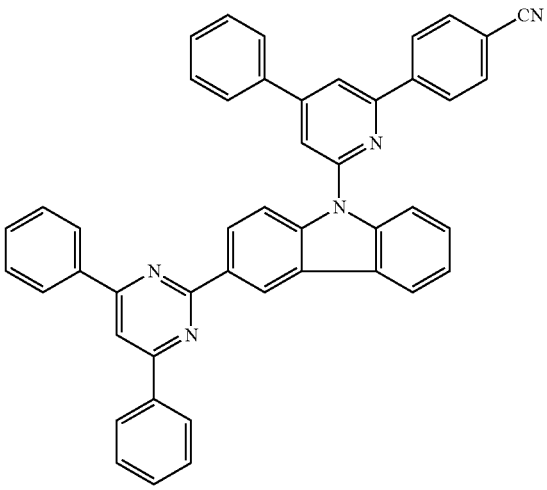
26
-continued
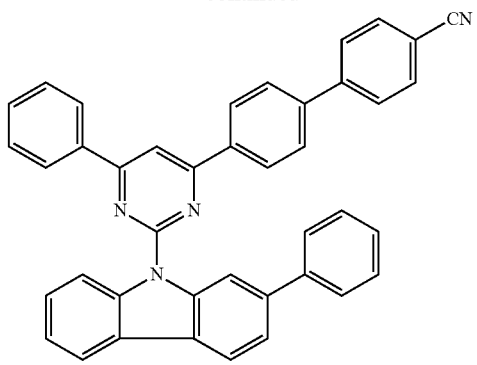
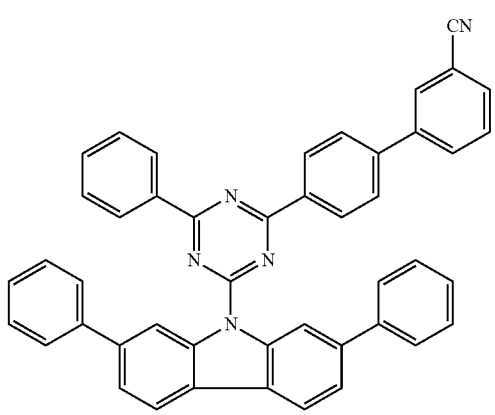
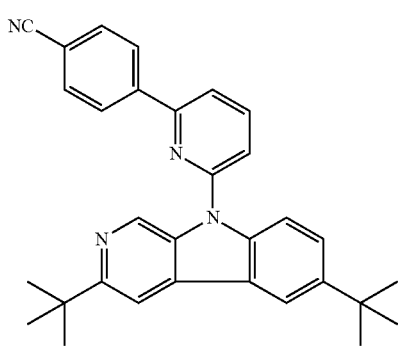
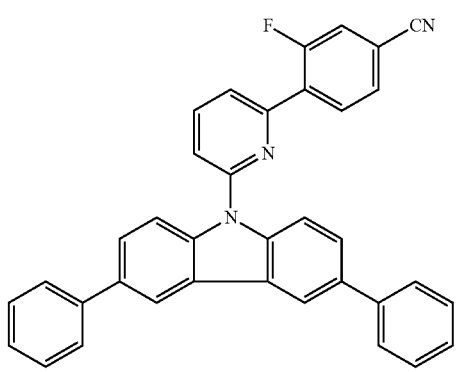

27
-continued
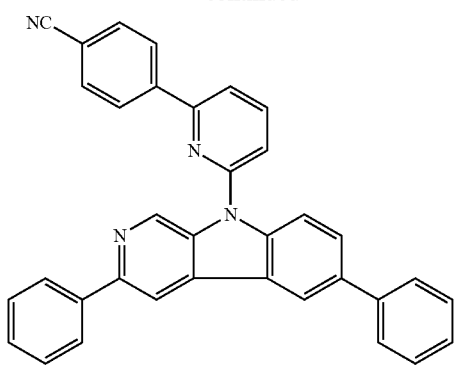
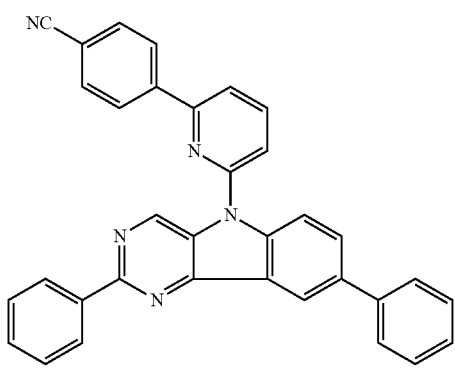
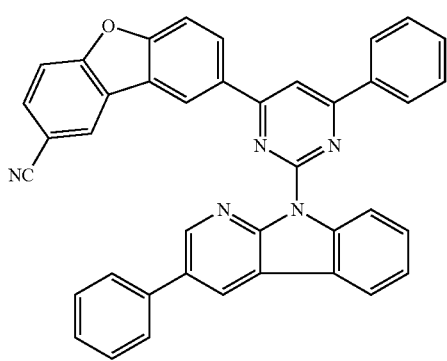
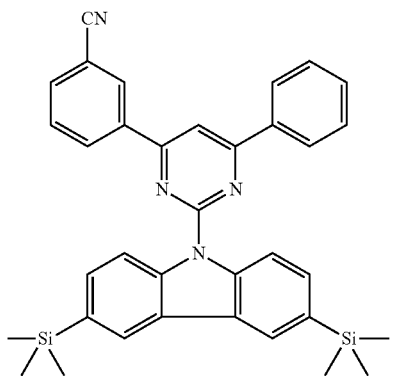
28
-continued
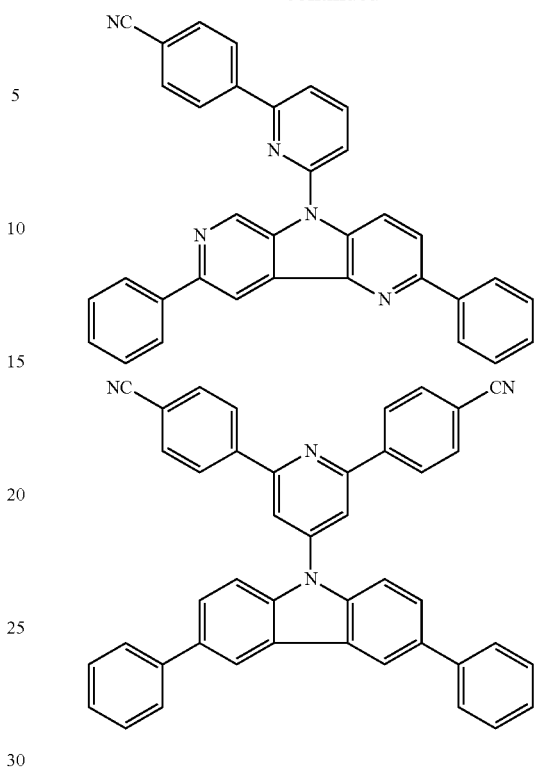
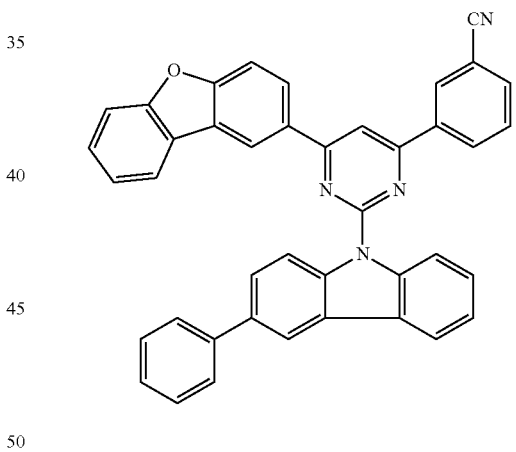
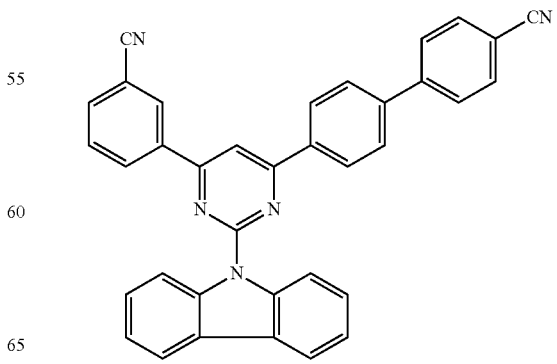

-continued
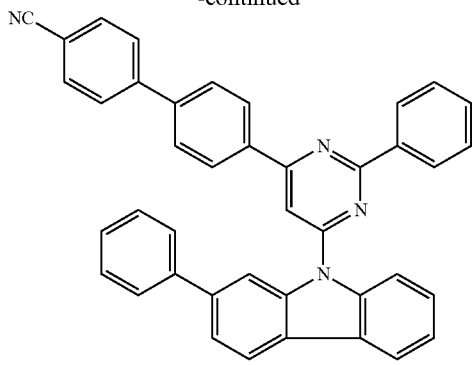
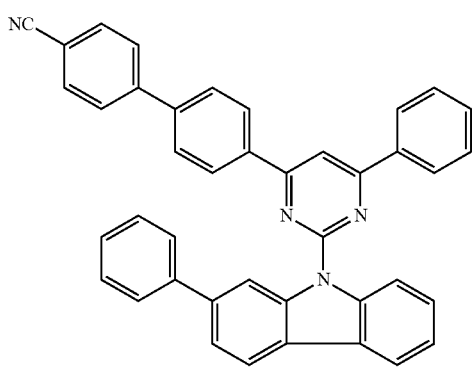
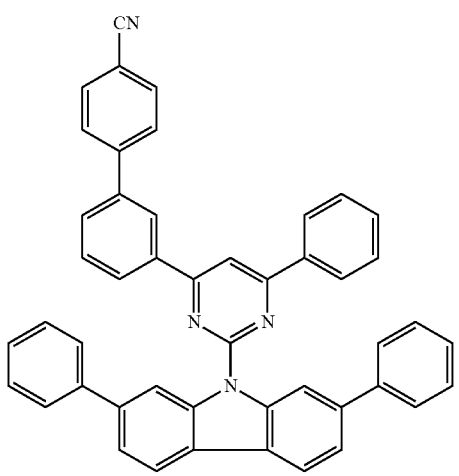
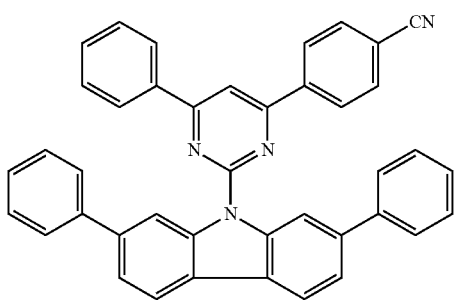
-continued
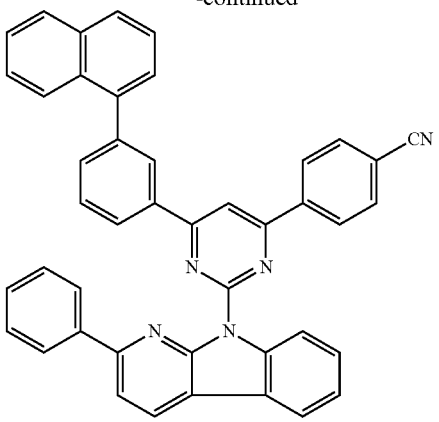
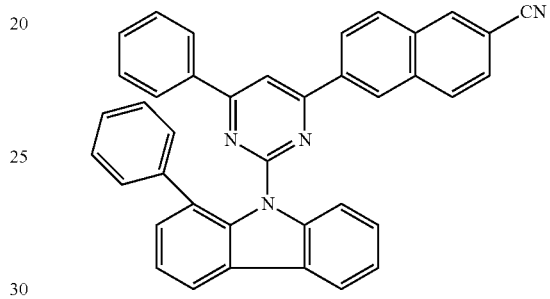
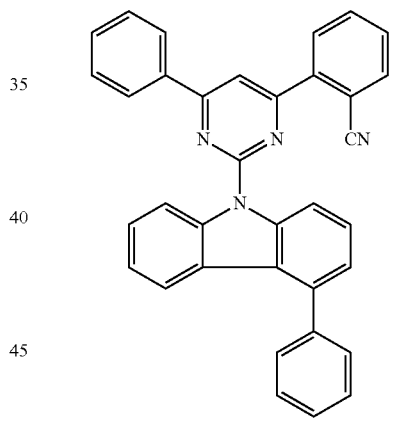
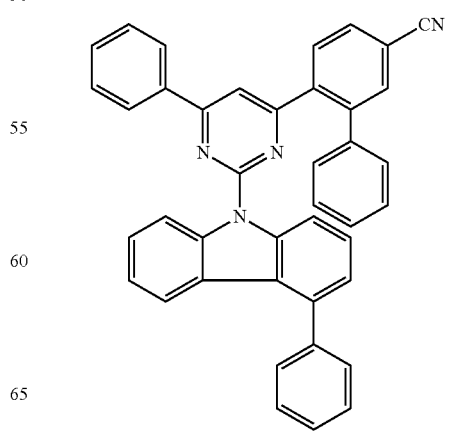

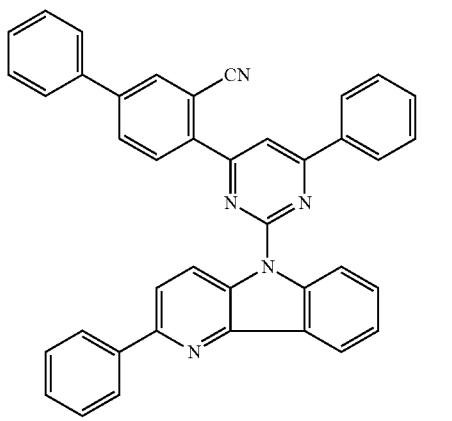
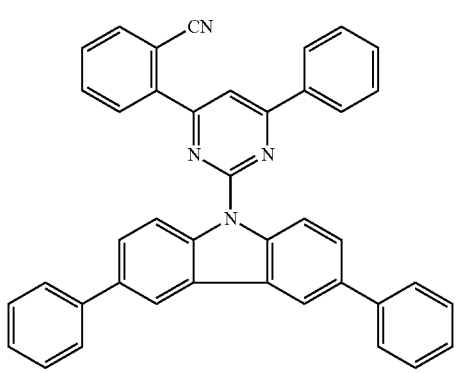
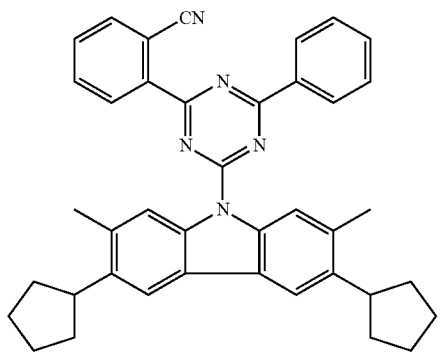
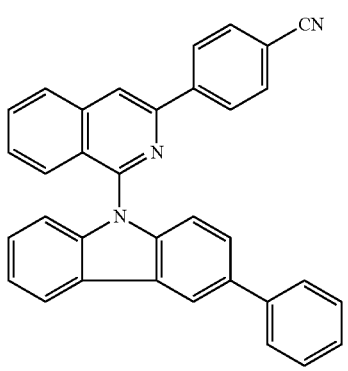
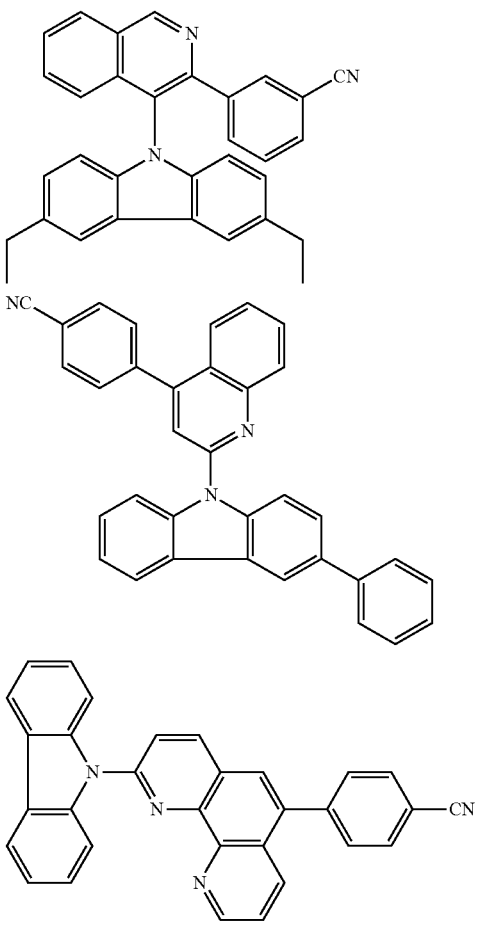
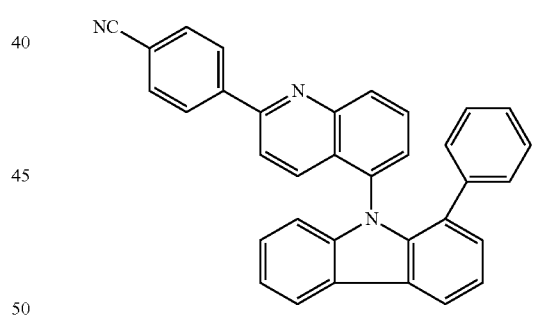
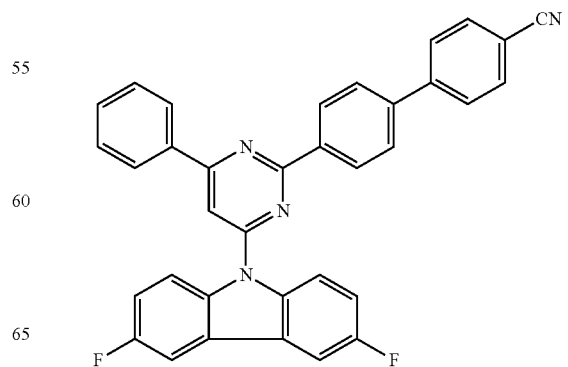

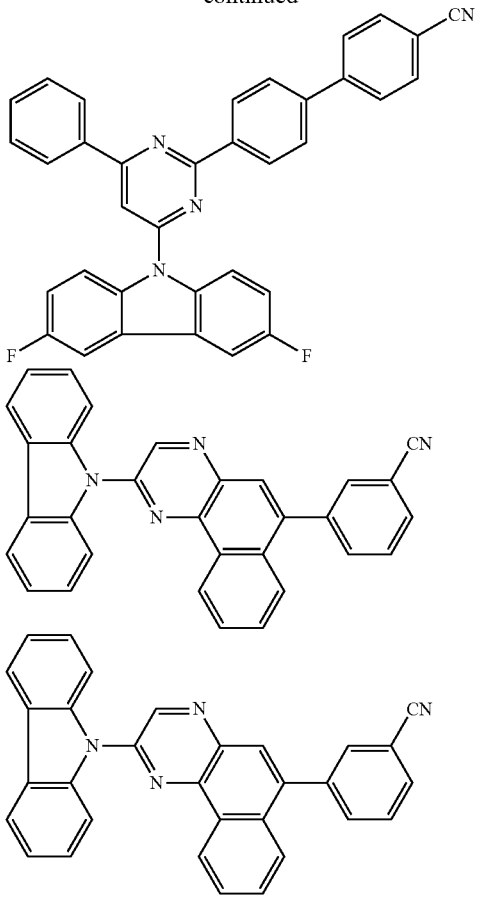

(Organic EL Device)

Next, the embodiments of the organic EL device of the invention are explained.

The organic EL device of the invention comprises organic thin film layers including an emitting layer between a cathode and an anode. Due to the organic EL device material of the invention contained in at least one layer of the organic thin film layers, the organic EL device is allowed to prolong life.

Examples of the organic thin film layer containing the organic EL device material of the invention include a hole-transporting layer, an emitting layer, an electron-transporting layer, a space layer and a blocking layer, but not limited thereto. The organic EL device material of the invention is preferably contained in an emitting layer, with use as a host material in the emitting layer being particularly preferable. In addition, the emitting layer contains a fluorescent material or phosphorescent material preferably, with a phosphorescent material being particularly preferable. Further, the organic EL device material of the invention is suitable for a blocking layer.

The organic EL device of the invention may be either a fluorescent or phosphorescent type monochrome emitting device or a fluorescent/phosphorescent hybrid type white color emitting device. Further, it may be either a simple device having a single emitting unit or a tandem type device having a plurality of emitting units. Among these, it is a phosphorescent type device preferably. Here, the term of "emitting unit" means the minimum unit which comprises one or more organic layers, one of which is an emitting layer, and can emit light by recombining injected holes and injected electrons.

Therefore, as a representative device constitution of a simple organic EL device, the following constitutions can be given.

(1) Anode/Emitting Unit/Cathode

The emitting unit mentioned above may be a stacked type emitting unit comprising a plurality of phosphorescent layers or fluorescent layers. In this case, between each emitting layer, a space layer may be provided in order to prevent diffusion of excitons generated in the phosphorescent layer to the fluorescent layer. The representative layer configurations of the emitting unit are given as follows.

(a) Hole-transporting layer/emitting layer (/electron-transporting layer)

(b) Hole-transporting layer/first phosphorescent layer/second phosphorescent layer (/electron-transporting layer)

(c) Hole-transporting layer/phosphorescent layer/space layer/fluorescent layer (/emitting layer)

(d) Hole-transporting layer/first phosphorescent layer/second phosphorescent layer/space layer/fluorescent layer (/electron-transporting layer)

(e) Hole-transporting layer/first phosphorescent layer/space layer/second phosphorescent layer/space layer/fluorescent layer (/electron-transporting layer)

(f) Hole-transporting layer/phosphorescent layer/space layer/first fluorescent layer/second fluorescent layer (/electron-transporting layer)

(g) Hole-transporting layer/electron-blocking layer/emitting layer (/electron-transporting layer)

(h) Hole-transporting layer/emitting layer/hole-blocking layer (/electron-transporting layer)

(i) Hole-transporting layer/fluorescent layer/triplet blocking layer (/electron-transporting layer)

The phosphorescent layers or the fluorescent layers mentioned above can emit colors which are different from each other. Specifically, in the stacked emitting layer (d), a configuration such as a hole-transporting layer/first phosphorescent layer (red emission)/second phosphorescent layer (green emission)/space layer/fluorescent layer (blue emission)/electron-transporting layer can be given.

Between each emitting layer and the hole-transporting layer or the space layer, an electron-blocking layer may be provided appropriately. Further, between each emitting layer and the electron-transporting layer, a hole-blocking layer may be appropriately provided. By providing an electron-blocking layer or a hole-blocking layer, it is possible to confine electrons or holes in the emitting layer to increase the possibility of recombination of charges in the emitting layer, whereby the lifetime of a device can be prolonged.

Representative device configuration of a tandem type organic EL device, the following device configurations can be given.

(2) Anode/First Emitting Unit/Intermediate Layer/Second Emitting Unit/Cathode

Here, as for each of the first emitting unit and the second emitting unit, the same emitting unit as mentioned above can be selected.

The intermediate layer is generally called as the intermediate electrode, the intermediate conductive layer, the charge-generating layer, the electron-withdrawing layer, the connecting layer and the intermediate insulating layer, and can have a known material configuration in which electrons are supplied to the first emitting unit and holes are supplied to the second emitting unit.

FIG. 1 shows a schematic configuration of one example of the organic EL device of the invention. An organic EL device 1 comprises a substrate 2, an anode 3, a cathode 4 and an emitting unit 10 between the anode 3 and the cathode 4. The emitting unit 10 comprises an emitting layer 5 that comprises at least one phosphorescent layer containing a phosphorescent host material and a phosphorescent dopant. A hole-injecting/transporting layer 6 or the like may be formed between the emitting layer 5 and the anode 3, and an electron-injecting/transporting layer 7 or the like may be formed between the emitting layer 5 and the cathode 4. Further, an electron-blocking layer may be provided on the side nearer to the anode 3 of the emitting layer and a hole-blocking layer may be provided on the side nearer to the cathode 4 of the emitting layer 5. Due to such a configuration, it is possible to confine electrons or holes in the emitting layer 5, whereby the possibility of formation of excitons in the emitting layer 5 can be increased.

In the specification of the invention, a host combined with a fluorescent dopant is called a fluorescent host, and a host combined with a phosphorescent dopant is called a phosphorescent dopant. The fluorescent host is not distinguished from the phosphorescent host only by the molecular structure. That is, the phosphorescent host means a material that constitutes a phosphorescent layer containing a phosphorescent dopant, and does not mean the phosphorescent host cannot be used as a material constituting a fluorescent layer. The same can be applied to the fluorescent host.

(Substrate)

The organic EL device of the invention is formed on a transparent substrate. A transparent substrate is a substrate which supports the organic EL device, and is preferably a smooth substrate having a 400-to-700-nm-visible-light transmittance of 50% or more. Specific examples thereof include glass plates and polymer plates. Examples of the glass plate include one made from soda-lime glass, barium/strontium-containing glass, lead glass, aluminosilicate glass, borosilicate glass, barium borosilicate glass, and quartz. Examples of the polymer plate include one made from polycarbonate, acrylic polymer, polyethylene terephthalate, polyethersulfone, and polysulfone.

(Anode)

The anode plays a role for injecting holes into the hole-transporting layer or emitting layer. It is effective to use one having a work function of 4.5 eV or higher. Specific examples of the anode material include indium tin oxide alloy (ITO), tin oxide (NESA), indium zinc oxide alloy, gold, silver, platinum, and copper. The anode can be formed by forming these electrode materials into a thin film by a method such as a deposition method and a sputtering method. In the case where emission from the emitting layer is taken out through the anode, the transmittance of the anode for the emission in the visible range is preferably more than 10%. The sheet resistance of the anode is preferably several hundred $\Omega/\square$ or less. The film thickness of the anode, which varies depending upon the material thereof, is usually from 10 nm to 1 μm, preferably from 10 nm to 200 nm.

(Cathode)

The cathode serves to inject electrons to the electron-injection layer, the electron-transporting layer or the emitting layer. It is preferred that the cathode may be formed of a material having a small work function. Although no specific restrictions are imposed on the cathode material, specifically, indium, aluminum, magnesium, magnesium-indium alloy, magnesium-aluminum alloy, aluminum-lithium alloy, aluminum-scandium-lithium alloy, magnesium-silver alloy or the like can be given. As in the case of the anode, the cathode can be formed by forming a thin film by a method such as a deposition method and a sputtering method. If need arises, light is outcoupled from the cathode.

(Emitting Layer)

The emitting layer is an organic layer having an emission function. If a doping system is used, the emitting layer contains a host material and a dopant material. In this case, the host material mainly has a function of promoting electrons and holes to confine the excitons in the emitting layer, and the dopant material has a function of allowing the excitons obtained by the recombination to emit light efficiently.

In the case of a phosphorescent device, the host material mainly has a function of confining excitons generated by the dopant in the emitting layer.

The above-mentioned emitting layer may use a double-host system (also called a host/co-host) that adjusts carrier balance in the emitting layer by combining an electron-transmitting host and a hole-transporting host or the like. It is preferred that the emitting layer contain the first host material and the second host material and that the first host material be the material for the organic EL device of the invention.

By incorporating two or more types of dopant materials having a high quantum efficiency, a double dopant system in which each dopant emits light may be used. Specifically, an embodiment can be given in which yellow emission is realized by using a common emitting layer by allowing a host, a red dopant and a green dopant to be co-deposited.

By allowing the above-mentioned emitting layer to be a stacked structure obtained by stacking a plurality of emitting layers, electrons and holes are allowed to be accumulated in the interface of the emitting layer, the recombination region is allowed to be concentrated on the interface of the emitting layer, whereby the quantum efficiency can be improved.

The degree of easiness in injection of holes to the emitting layer may differ from the degree of easiness in injection of electrons in the emitting layer. Further, the hole-transporting capability and the electron-transporting capability represented by the mobility of holes and electrons in the emitting layer may differ from each other.

As the method for forming the emitting layer, a known method such as deposition, spin coating, or an LB (Langmuir Blodgett) method may be applied. Further, an emitting layer may be formed by forming into a thin film by spin coating or the like a solution obtained by dissolving a binder such as a resin and a material compound in a solvent.

It is preferable that the emitting layer be a molecular deposition film. Here, the molecular deposition film means a thin film formed by deposition of a material compound in a vapor phase or a film formed by solidification of a material compound which is in a solution state or in a liquid state. The molecular deposition film is normally distinguished from a thin film (molecular accumulation film) formed using the LB method by the difference in aggregation structure or higher order structure or the difference in function due to the difference in structure.

The dopant material is selected from a known fluorescent dopant that shows fluorescent emission and a known phosphorescent dopant that shows phosphorescent emission.

The fluorescent dopant is selected from a fluoranthene derivative, a pyrene derivative, an arylacetylene derivative, a fluorene derivative, a boron complex, a perylene derivative, an oxadiazole derivative, an anthracene derivative and a chrysene derivative. Of these, a fluorantene derivative, a pyrene derivative and a boron complex are preferably given.

A phosphorescent dopant (phosphorescent material) that forms the emitting layer is a compound which can emit light from a triplet exciton. Although the type of the dopant is not particularly restricted as long as it can emit from a triplet exciton, the dopant is preferably a metal complex containing at least one metal selected from the group consisting of Ir, Pt, Os, Au, Cu, R$^e$ and Ru. It is preferred that the ligand have an orthometal bond. In respect of a high phosphorescence quantum yield and being capable of further improving the external quantum efficiency of an emitting layer, a metal complex containing a metal atom selected from Ir, Os and Pt is preferable. A metal complex such as an iridium complex, an osmium complex and a platinum complex are preferable, with an orthometalated complex being particularly preferable. An iridium complex and a platinum complex are further preferable, with an orthometalated iridium complex being particularly preferable.

The content of a phosphorescent dopant in the emitting layer is not particularly restricted, and can be appropriately selected according to the purpose. The content is 0.1 to 70 mass %, for example, with 1 to 30 mass % being preferable. If the content of a phosphorescent compound is 0.1 mass % or more, sufficient emission is obtained. If the content is 70 mass % or less, concentration quenching can be eliminated.

Specific examples of the organic metal complex preferable as the phosphorescent dopant are given below.

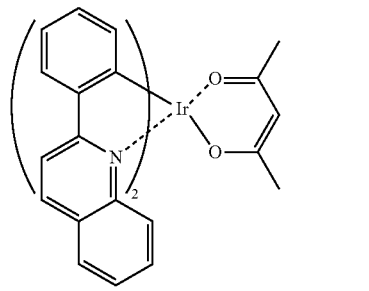

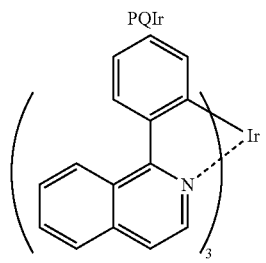

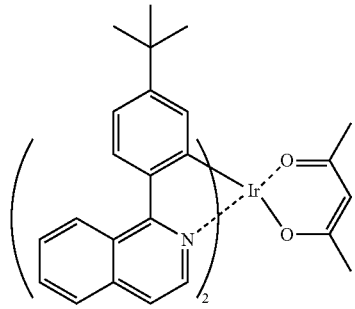

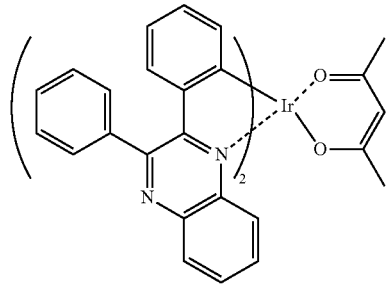

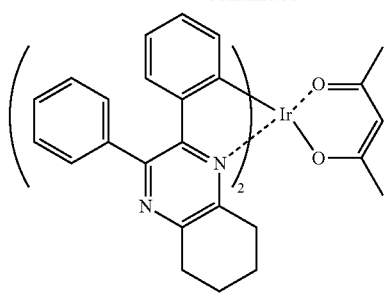

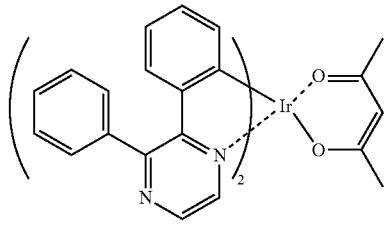

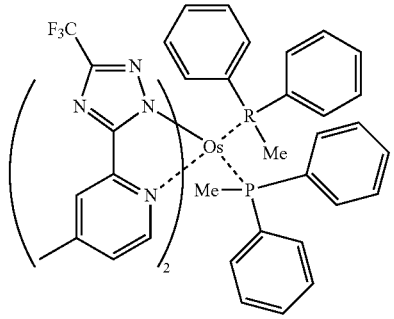

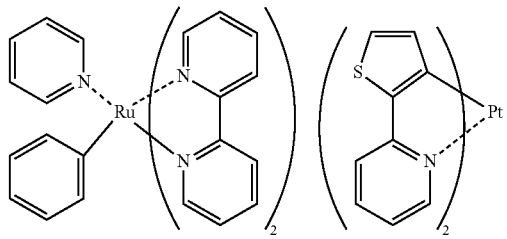

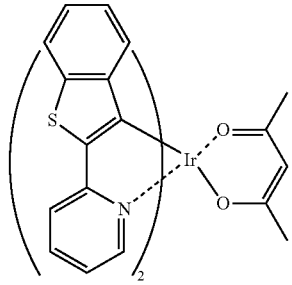

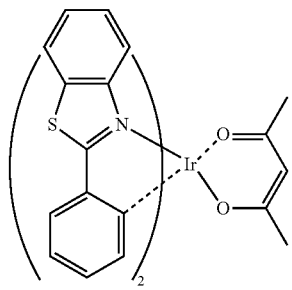

-continued
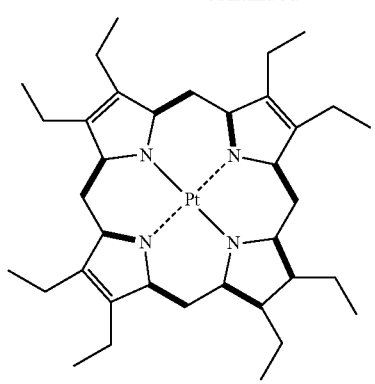
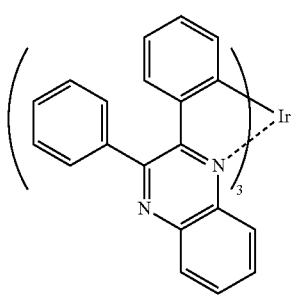
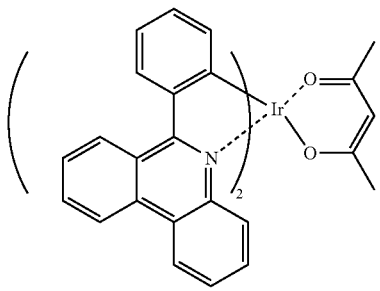
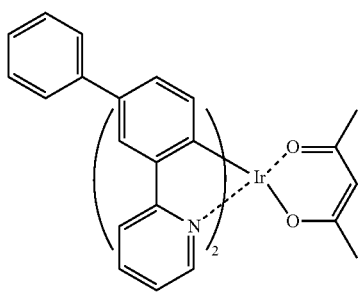
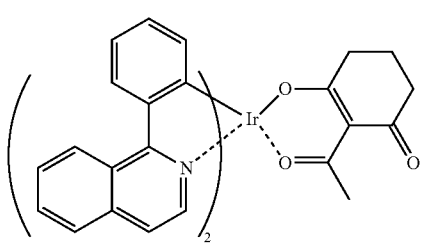
-continued
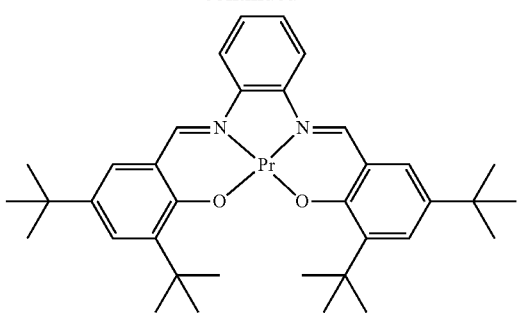
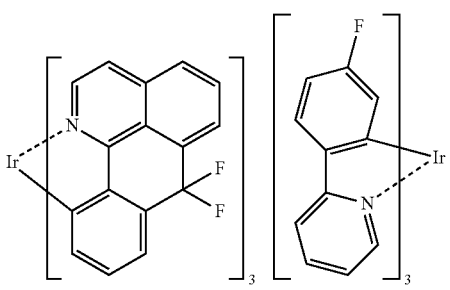
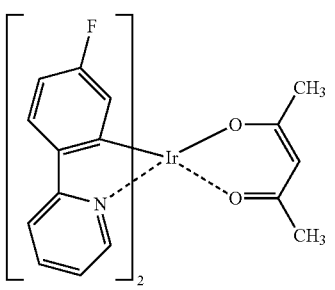
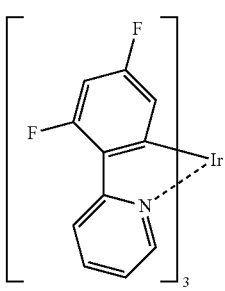
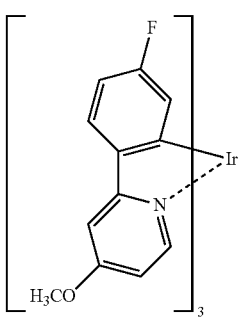

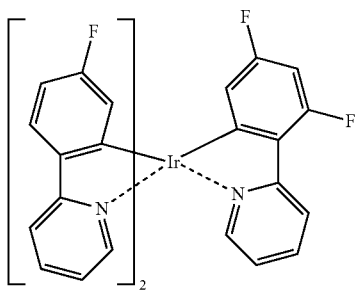
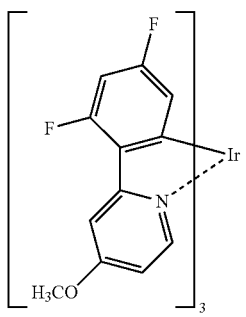
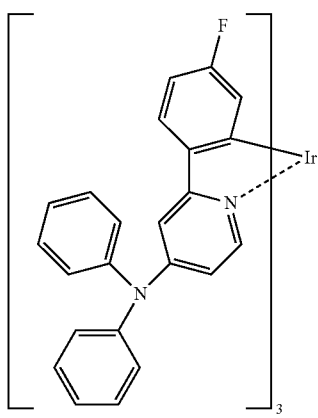
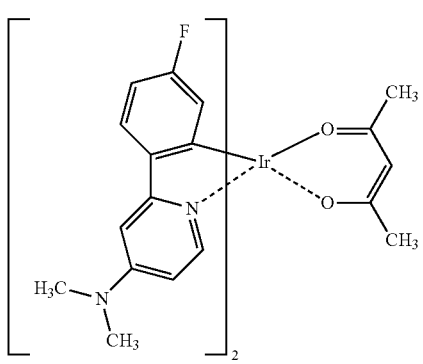
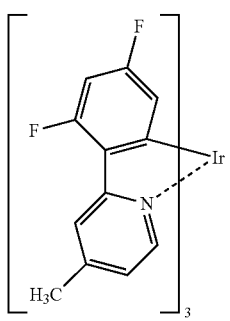
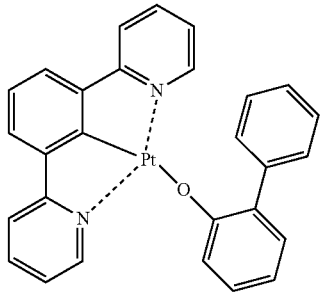
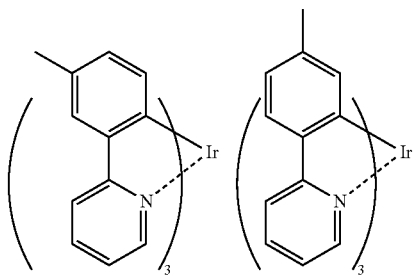
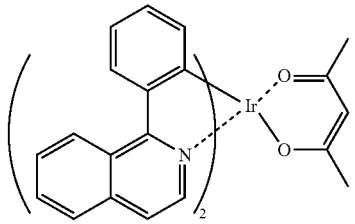
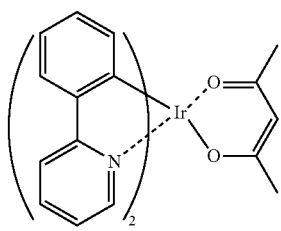
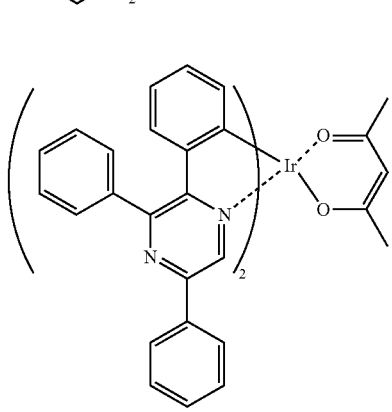
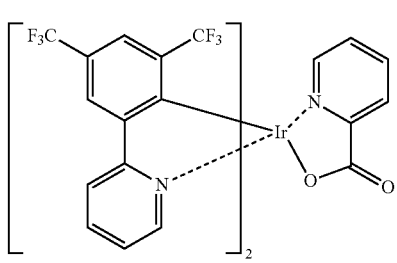

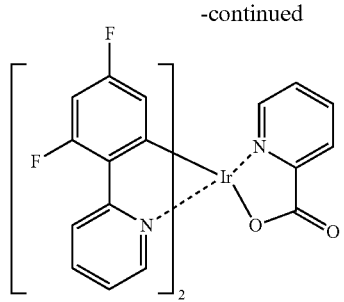
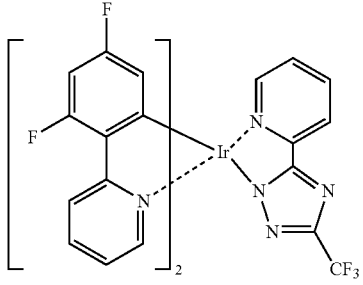
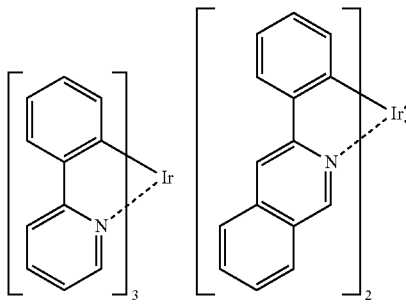
Ir(ppy)₃
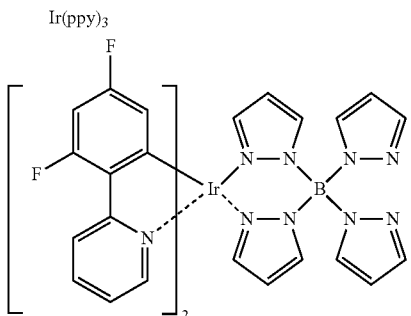
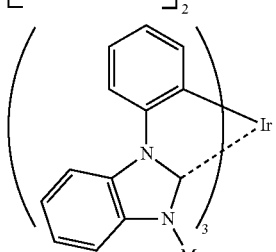
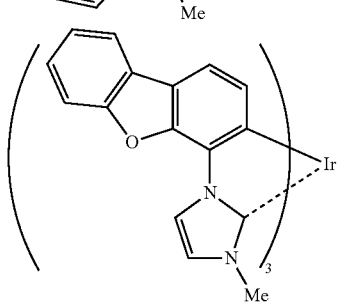
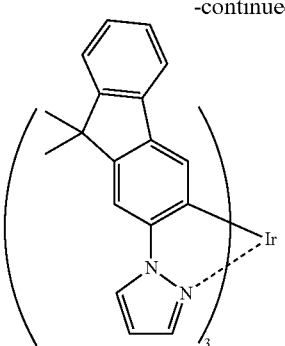
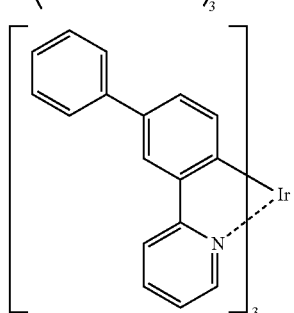
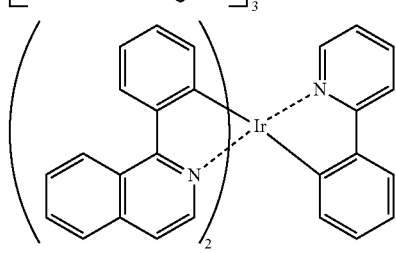
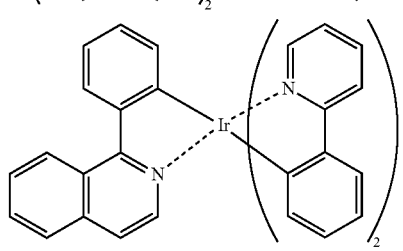
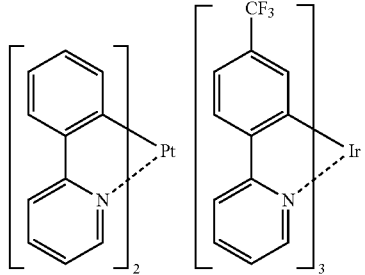
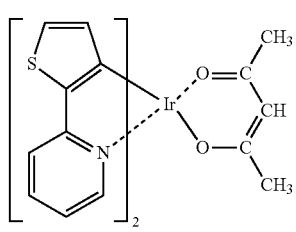

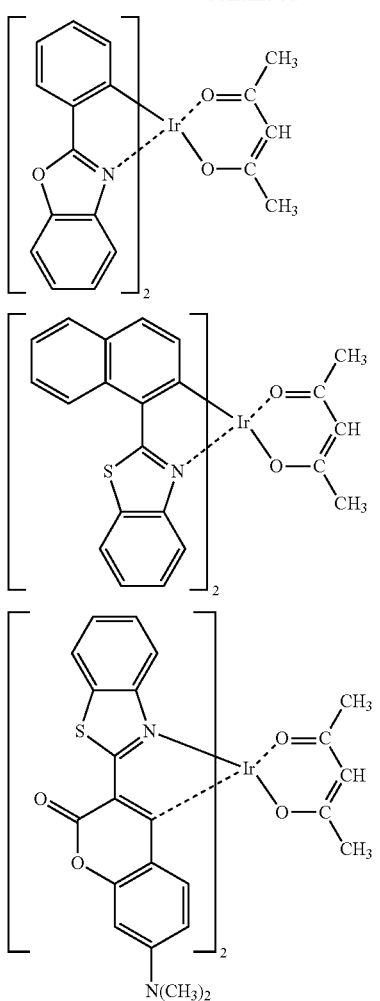
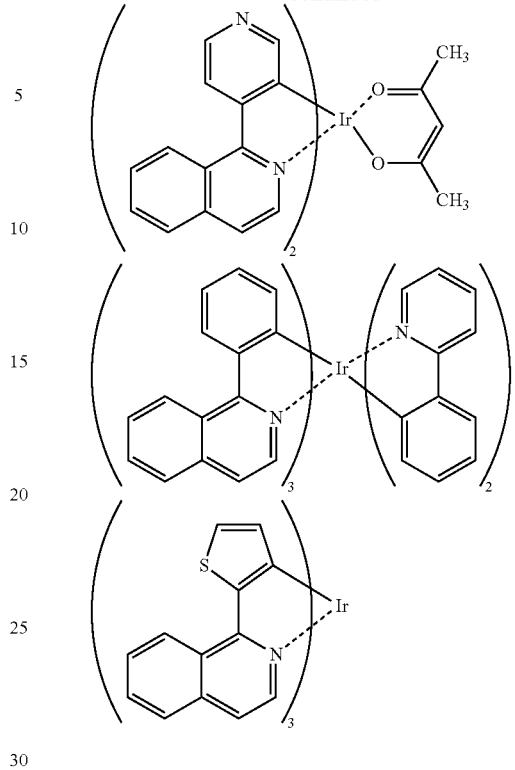

A phosphorescent host is a compound which has a function of allowing a phosphorescent dopant to emit light efficiently by confining the triplet energy of the phosphorescent dopant in the emitting layer efficiently. The material for an organic EL device of the invention is preferable as a phosphorescent host. The emitting layer may contain the material for an organic EL device of the invention singly or in combination of two or more.

When the material for an organic EL device of the invention is used as the host material of the emitting layer, the emission wavelength of the phosphorescent dopant contained in the emitting layer is not particularly restricted. It is preferred that at least one of the phosphorescent dopant materials contained in the emitting layer have a peak of emission wavelength of 490 nm or more and 700 nm or less, more preferably 490 nm or more and 650 nm or less. As the emission color of the emitting layer, red, yellow and green are preferable, for example. By using the compound of the invention as the host material and by constituting the emitting layer by doping a phosphorescent dopant material having such an emission wavelength, the organic EL device can have a long life time.

In the organic EL device of the invention, a compound other than the materials for an organic EL device of the invention can be appropriately selected as a phosphorescent host according to the above-mentioned object.

The material for an organic EL device of the invention and other compounds may be used in combination as the phosphorescent host material in the same emitting layer. If there are a plurality of emitting layers, the material for an organic EL device of the invention can be used as the phosphorescent host material in one of these plurality of emitting layers, and compounds other than the material for an organic EL device of the invention can be used as the phosphorescent host material in another emitting layer. The material for an organic EL device of the invention can be used in an organic layer other than the emitting layer. In this case, compounds other than the material for an organic EL device of the invention may be used as the phosphorescent host of the emitting layer.

As for the compounds other than the material for an organic EL device of the invention, specific examples of the compound preferable as the phosphorescent host include heterocyclic tetracarboxylic anhydrides such as carbazole derivatives, triazole derivates, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted calcone derivatives, styryl anthracene derivatives, fluorenone derivatives, hydrazone derivatives, stilbene derivatives, silazane derivatives, aromatic tertiary amine compounds, styrylamine compounds, aromatic dimethylidene compounds, porphyrin compounds, anthraquinodimethane derivatives, anthrone derivatives, diphenylquinone derivatives, thiopyrandioxide derivatives, carbodiimide derivatives, fluoreniridenemethane derivatives, distyrylpyrazine derivatives and naphthaleneperylene; metal complexes of phthalocyanine derivatives and 8-quinolinol derivatives, various metal complex polysilane compounds represented by metal complexes having metalphthalocyanine, benzoxazole or benzothiazole as a ligand, electroconductive high-molecular oligomers such as poly(N-vinylcarbazole) derivatives, aniline copolymers, thiophene oligomers and polythiophene; and high-molecular compounds such as polythiophene derivatives, polyphenylene derivatives, polyphenylenevinylene derivatives and polyfluorene derivatives. Phosphorescent host compounds can be used individually or as a combination of two or more kinds. Specific compounds shown below can be exemplified.

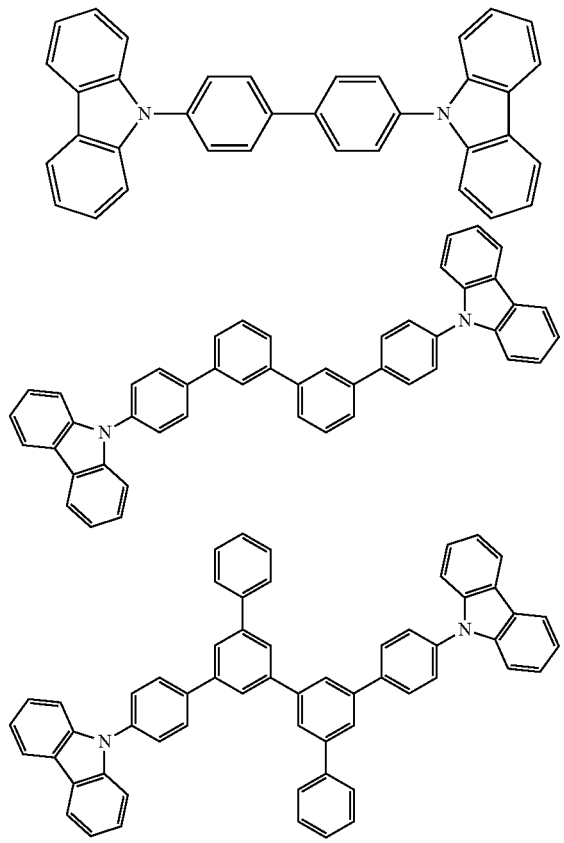

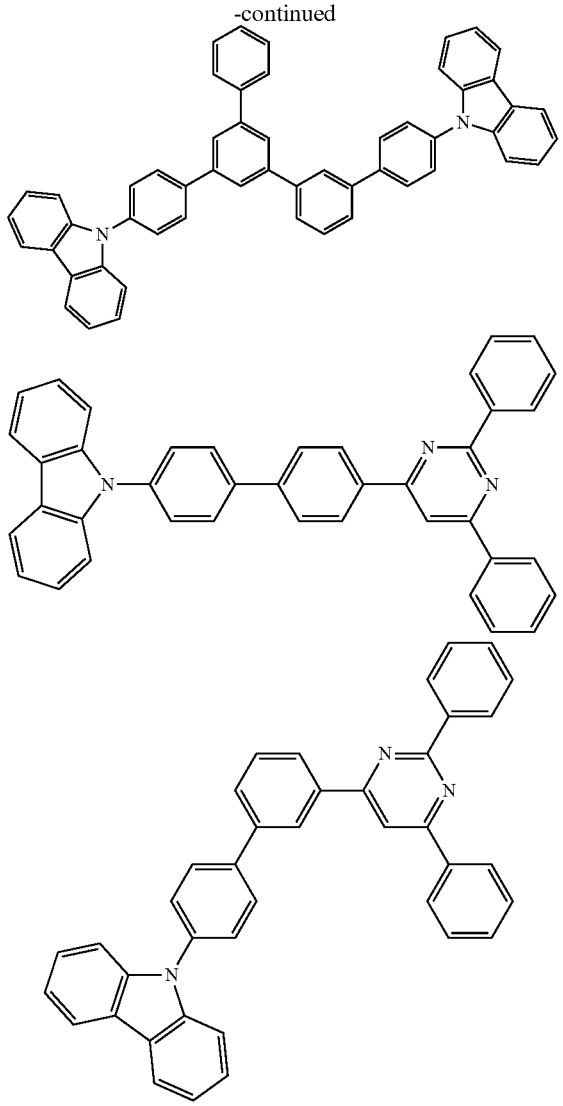

If the emitting layer contains the first host material and the second host material, the material for an organic EL device of the invention may be used as the first host material, and compounds other than the material for an organic EL device of the invention may be used as the second host material. In the invention, the "first host material" and the "second host material" mean that a plurality of host materials contained in the emitting layer may be different in structure from each other, and the difference between the "first" and the "second" is not defined by the content of the host material in the emitting layer.

No specific restrictions are imposed on the second host material, and compounds other than the material for an organic EL device of the invention and are the same as above as the compounds preferable as the phosphorescent host can be given. As the second host material, a compound having no cyano group is preferable. As the second host, a carbazole derivative, an arylamine derivative, a fluorenone derivative and an aromatic tertiary amine compound are preferable.

The thickness of the emitting layer is preferably 5 to 50 nm, more preferably 7 to 50 nm, with 10 to 50 nm being further preferable. If the thickness of the emitting layer is 5 nm or more, the emitting layer can be formed easily. If the thickness of the emitting layer is 50 nm or less, an increase in driving voltage can be avoided.

(Electron-Donating Dopant)

In the organic EL device of the invention, it is preferred that an electron-donating dopant be provided in the interface region of the cathode and the emitting unit. Due to such a configuration, an organic EL device can have improved luminance or a prolonged lifetime. Here, an electron-donating dopant means a dopant containing a metal having a work function of 3.8 eV or less. As specific examples thereof, at least one selected from an alkali metal, an alkali metal complex, an alkali metal compound, an alkaline earth metal, an alkaline earth metal complex, an alkaline earth metal compound, a rare earth metal, a rare earth metal complex and a rare earth metal compound can be given.

As the alkali metal, Na (work function: 2.36 eV), K (work function: 2.28 eV), Rb (work function: 2.16 eV), Cs (work function: 1.95 eV) or the like can be given. Metals having a work function of 2.9 eV or less are particularly preferable. Of these, K, Rb, Cs are preferable, and Rb or Cs is further preferable, with Cs being most preferable. As the alkaline earth metal, Ca (work function: 2.9 eV), Sr (work function: 2.0 to 2.5 eV), Ba (work function: 2.52 eV) or the like can be given. Metals having a work function of 2.9 eV or less are particularly preferred. As the rare earth metal, Sc, Y, Ce, Tb, Yb or the like can be given, and metals having a work function of 2.9 eV or less are particularly preferable.

As the alkali metal compound, an alkali oxide such as $Li_2O$, $Cs_2O$ and $K_2O$ and an alkali halide such as LiF, NaF, CsF and KF can be given. Of these, LiF, $Li_2O$ and NaF are preferable. As the alkaline earth metal compound, BaO, SrO, CaO and a mixture of these (e.g. $Ba_xSr_{1-x}O$ (0<x<1), $Ba_xCa_{1-x}O$ (0<x<1) or the like) can be given. Of these, BaO, SrO and CaO are preferable. As the rare earth metal compound, $YbF_3$, $ScF_3$, $ScO_3$, $Y_2O_3$, $Ce_2O_3$, $GdF_3$, $TbF_2$ or the like can be given. Of these, $YbF_3$, $ScF_3$ and $TbF_2$ are preferable.

No specific restrictions are imposed on the alkali metal complex, the alkaline earth metal complex and the rare earth metal complex, as along as they contain at least one of an alkali metal ion, an alkaline earth metal ion and a rare earth metal ion as the metal ion. As the ligand, quinolinol, benzoquinolinol, acrydinol, phenanthridinol, hydroxyphenyl oxazole, hydroxyphenyl thiazole, hydroxydiaryl oxadiazole, hydroxydiaryl thiadiazole, hydroxyphenyl pyridine, hydroxyphenyl benzimidazole, hydroxybenzo triazole, hyroxyfluborane, bipyridyl, phenanthroline, phthalocyanine, porphyrin, cyclopentadiene, β-diketone, azomethine, and derivatives thereof are preferable, but not limited thereto.

The electron-donating dopant is preferably added in the form of a layer or an island in the interfacial region. As the formation method, a method is preferable in which, while depositing an electron-donating dopant by the resistance heating deposition method, an organic compound (an emitting material or an electron-injecting material) that forms an interfacial region is simultaneously deposited, whereby a electron-donating dopant is dispersed in the organic substance. The dispersion concentration is preferably organic compound:electron-donating dopant=100:1 to 1:100 in terms of molar ratio, with 5:1 to 1:5 being more preferable.

When forming an electron-donating dopant in the form of a layer, after forming into a layer the emitting material or the electron-injecting material which is the organic layer of the interface, the electron-reducing dopant is singly deposited by the resistance heating deposition method, preferably in a layer thickness of 0.1 to 15 nm. When forming an electron-donating dopant in the form of an island, after forming into an island the emitting material or the electron-injecting material which is the organic layer of the interface, the electron-donating dopant is singly deposited by the resistance heating deposition method, preferably in an island thickness of 0.05 to 1 nm.

In the organic EL device of the invention, the ratio of the main component and the electron-donating dopant is preferably main component:electron-donating dopant 5:1 to 1:5 in terms of molar ratio, with 2:1 to 1:2 being further preferable.

(Electron-Transporting Layer)

The electron-transporting layer is an organic layer formed between the emitting layer and the cathode and has a function of transporting electrons from the cathode to the emitting layer. If the electron-transporting layer is formed of a plurality of layers, an organic layer closer to the cathode may often be defined as an electron-injecting layer. The electron-injecting layer has a function of injecting electrons efficiently from the cathode to an organic layer unit.

As the electron-transporting material used in the electron-transporting layer, an aromatic heterocyclic compound having one or more hetero atoms in its molecule is preferable. A nitrogen-containing ring derivative is particularly preferable. As the nitrogen-containing ring derivative, an aromatic ring having a nitrogen-containing six-membered ring skeleton or a nitrogen-containing five-membered ring skeleton, or a fused aromatic ring compound having a nitrogen-containing six-membered ring skeleton or a nitrogen-containing five-membered ring skeleton is preferable.

As this nitrogen-containing ring derivative, a nitrogen-containing ring metal chelate complex represented by the following formula (A) is preferable.

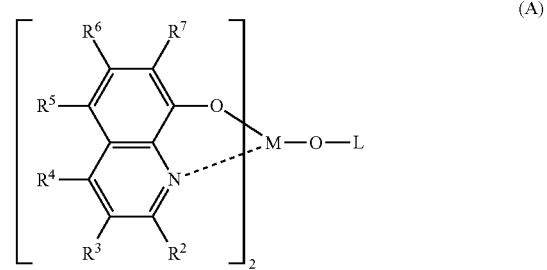

(A)

$R^2$ to $R^7$ in the formula (A), which is a nitrogen-containing metal chelate complex, are independently a hydrogen atom, a deuterium atom, a halogen atom, a hydroxyl group, an amino group, a hydrocarbon group having 1 to 40 carbon atoms, an alkoxy group having 1 to 40 carbon atoms, an aryloxy group having 6 to 50 carbon atoms, an alkoxycarbonyl group or an aromatic heterocyclic group having 5 to 50 ring carbon atoms, which may be substituted.

As the halogen atom, fluorine, chlorine, bromine, iodine or the like can be given.

Examples of the amino group which may be substituted include an alkylamino group, an arylamino group and an aralkylamino group.

The alkylamino group and the aralkylamino group are represented by $—NQ^1Q^2$. $Q^1$ and $Q^2$ are independently an alkyl group having 1 to 20 carbon atoms or an aralkyl group having 1 to 20 carbon atoms. One of $Q^1$ and $Q^2$ may be a hydrogen atom or a deuterium atom.

The arylamino group is represented by $—NAr^1Ar^2$. $Ar^1$ and $Ar^2$ are independently a non-fused aromatic hydrocarbon group having 6 to 50 carbon atoms or fused aromatic hydrocarbon atoms having 6 to 50 carbon atoms. One of $Ar^1$ and $Ar^2$ may be a hydrogen atom or a deuterium atom.

The hydrocarbon group having 1 to 40 carbon atoms includes an alkyl group, an alkenyl group, a cycloalkyl group, an aryl group and an aralkyl group.

The alkoxycarbonyl group is represented by —COOY', and Y' is an alkyl group having 1 to 20 carbon atoms.

M is aluminum (Al), gallium (Ga) or indium (In), with In being preferable.

L is a group represented by the following formulas (A') or (A").

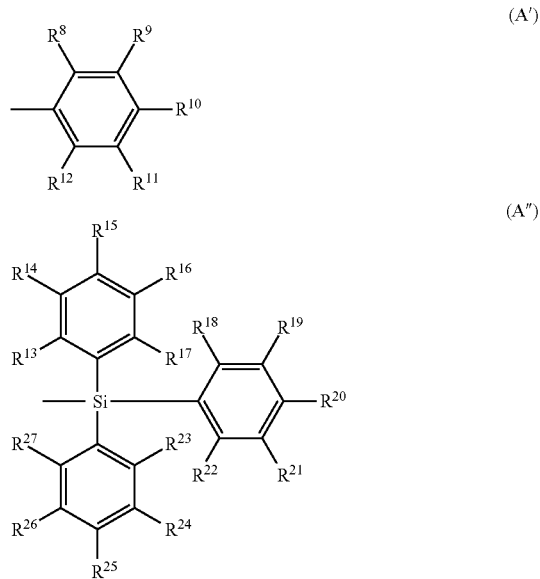

In the formula (A'), $R^8$ to $R^{12}$ are independently a hydrogen atom, a deuterium atom or a substituted or unsubstituted hydrocarbon group having 1 to 40 carbon atoms, and adjacent groups may form a ring structure. $R^{13}$ to $R^{27}$ in the formula (A") are independently a hydrogen atom, a deuterium atom or a substituted or unsubstituted hydrocarbon group having 1 to 40 carbon atoms, and adjacent groups may form a ring structure.

The hydrocarbon group having 1 to 40 carbon atoms represented by $R^8$ to $R^{12}$ and $R^{13}$ to $R^{27}$ in the formulas (A) and (A") are the same as the hydrocarbon group represented by $R^2$ to $R^7$ in the formula (A) which is the nitrogen-containing chelate complex. As the divalent group represented by $R^8$ to $R^{12}$ and $R^{13}$ to $R^{27}$ in which adjacent groups form a ring structure, a tetramethylene group, a pentamethylene group, a hexamethylene group, a diphenylmethane-2,2'-diyl group, a diphenylethane-3,3'-diyl group, a diphenylpropane-4,4'-diyl group or the like can be given.

The electron-transmitting compound used in the electron-transporting layer is preferably a metal complex of 8-hydroxyquinoline or a derivative thereof, an oxadiazole derivative or a nitrogen-containing heterocyclic derivative. Specific examples of the metal complexes of 8-hydroxyquinoline or derivatives thereof include metal chelate oxynoid compounds containing a chelate of oxine (generally, 8-quinolinol or 8-hydroxyquinoline). For example, tris(8-quinolinol)aluminum can be used. As the oxadizole derivative, the following can be given.

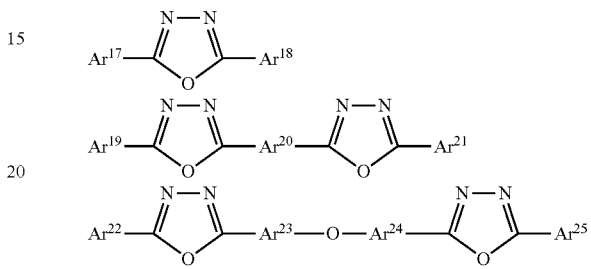

In the above formula, $Ar^{17}$, $Ar^{18}$, $Ar^{19}$, $Ar^{21}$, $Ar^{22}$ and $Ar^{25}$ are independently a substituted or unsubstituted aromatic hydrocarbon group or fused aromatic hydrocarbon group having 6 to 50 carbon atoms. $Ar^{17}$ and $Ar^{18}$, $Ar^{19}$ and $Ar^{21}$ and $Ar^{22}$ and $Ar^{25}$ may be the same or different. As the aromatic hydrocarbon group or the fused aromatic hydrocarbon group, a phenyl group, a naphthyl group, a biphenyl group, an anthranyl group, a perylenyl group, a pyrenyl group or the like can be given. As the substituent, an alkyl group having 1 to 10 carbon atoms, an alkoxy group having 1 to 10 carbon atoms, a cyano group, and the like can be given.

$Ar^{20}$, $Ar^{23}$ and $Ar^{24}$ are independently a substituted or unsubstituted divalent aromatic hydrocarbon group or fused aromatic hydrocarbon group having 6 to 50 carbon atoms, and $Ar^{23}$ and $Ar^{24}$ may be the same or different. As the divalent aromatic hydrocarbon group or the divalent fused aromatic hydrocarbon group, a phenylene group, a naphthylene group, a biphenylene group, an anthranylene group, a perylenylene group, a pyrenylene group or the like can be given. As the substituent, an alkyl group having 1 to 10 carbon atoms, an alkoxy group having 1 to 10 carbon atoms, a cyano group, and the like can be given.

As for these electron-transmitting compounds, one capable of forming a thin film is preferably used. Specific examples of these electron-transmitting compounds, the following can be given.

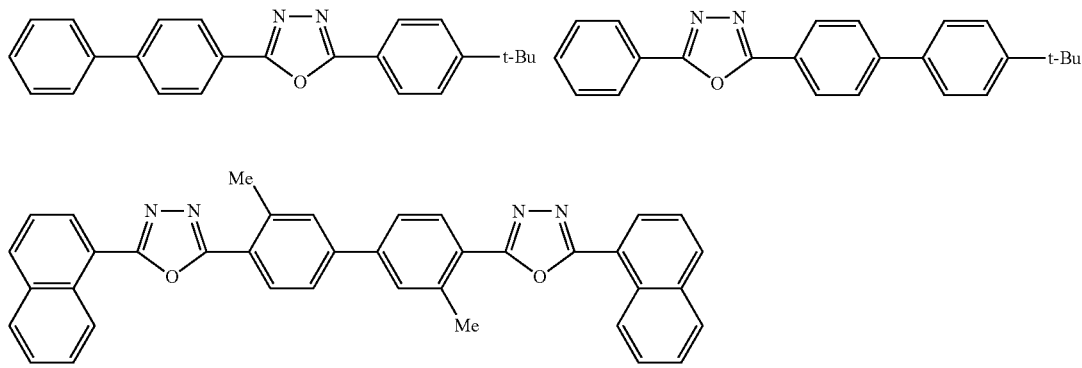

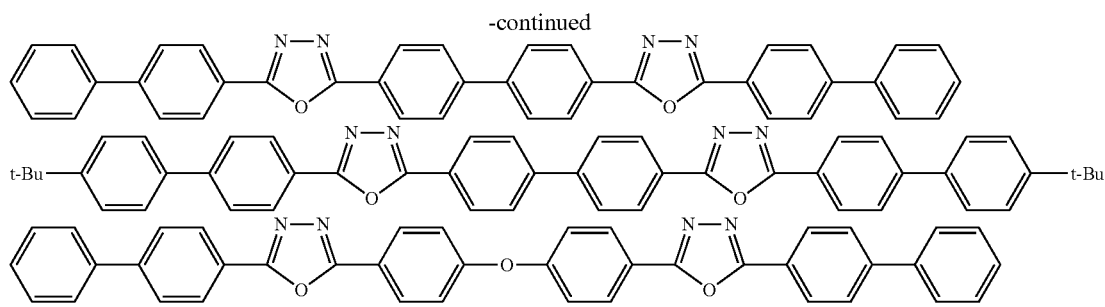

The nitrogen-containing heterocyclic derivative as the electron-transmitting compound is a nitrogen-containing heterocyclic derivative formed of an organic compound represented by the following formulas. A nitrogen-containing compound which is not a metal complex can be given. For example, a five-membered ring or six-membered ring having a skeleton represented by the following formula (B) or one having a structure represented by the following formula (C) can be given.

(B)

(C)

In the formula (C), X is a carbon atom or a nitrogen atom. $Z_1$ and $Z_2$ are independently a group of atoms capable of forming a nitrogen-containing heterocyclic ring.

It is further preferred that the nitrogen-containing heterocyclic derivative be an organic compound comprising a nitrogen-containing aromatic polycyclic group composed of a five-membered ring or a six-membered ring. Further, in the case of a nitrogen-containing aromatic polycyclic group comprising plural nitrogen atoms, a nitrogen-containing aromatic polycyclic organic compound having a skeleton obtained by combination of the above formulas (B) and (C) or the above formulas (B) and (D) is preferable.

(D)

The nitrogen-containing group of the above-mentioned nitrogen-containing aromatic polycyclic organic compound is selected from the nitrogen-containing heterocyclic groups represented by the following formulas.

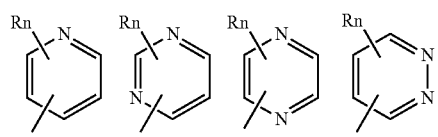

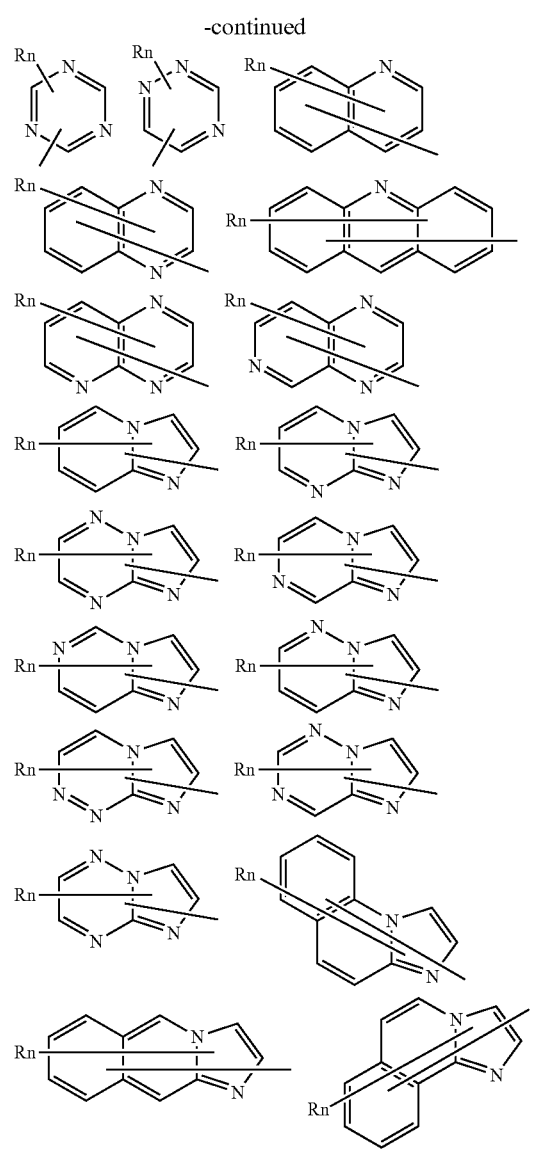

In each of the above formulas, R is an aromatic hydrocarbon group or fused aromatic hydrocarbon group having 6 to 40 carbon atoms or an aromatic heterocyclic group or fused aromatic heterocyclic group having 3 to 40 carbon atoms, an alkyl group having 1 to 20 carbon atoms or an alkoxy group having 1 to 20 carbon atoms; and n is an integer in a range of 0 to 5. When n is an integer of 2 or more, plural Rs may be the same or different.

A further preferable specific compound is a nitrogen-containing heterocyclic derivative represented by the following formula (D1):

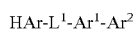

in the formula (D1), HAr is a substituted or unsubstituted nitrogen-containing heterocyclic group having 3 to 40 carbon atoms; $L^1$ is a single bond, a substituted or unsubstituted aromatic hydrocarbon group or fused aromatic hydrocarbon group having 6 to 40 carbon atoms, or a substituted or unsubstituted aromatic heterocyclic group or fused aromatic heterocyclic group having 3 to 40 carbon atoms; $Ar^1$ is a substituted or unsubstituted divalent aromatic hydrocarbon group having 6 to 40 carbon atoms; and $Ar^2$ is a substituted or unsubstituted aromatic hydrocarbon group or fused aromatic hydrocarbon group having 6 to 40 carbon atoms, or substituted or unsubstituted aromatic heterocyclic group or fused aromatic heterocyclic group having 3 to 40 carbon atoms.

HAr is selected from the following group, for example.

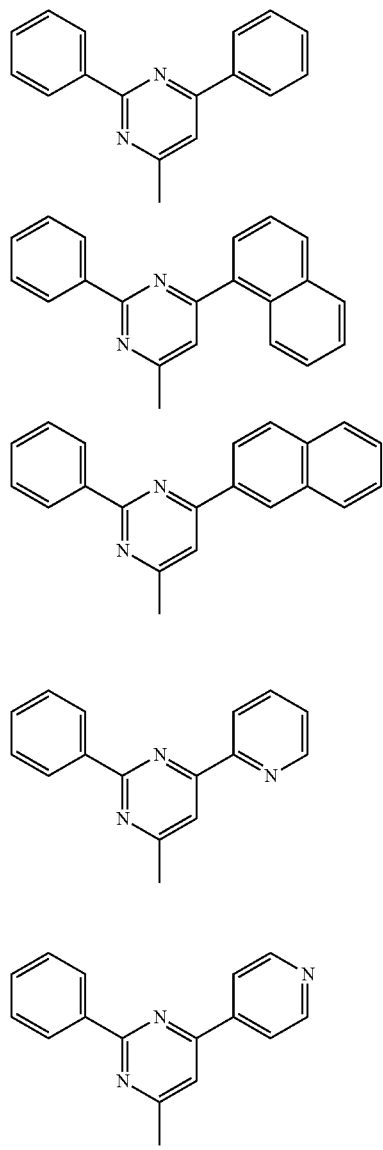

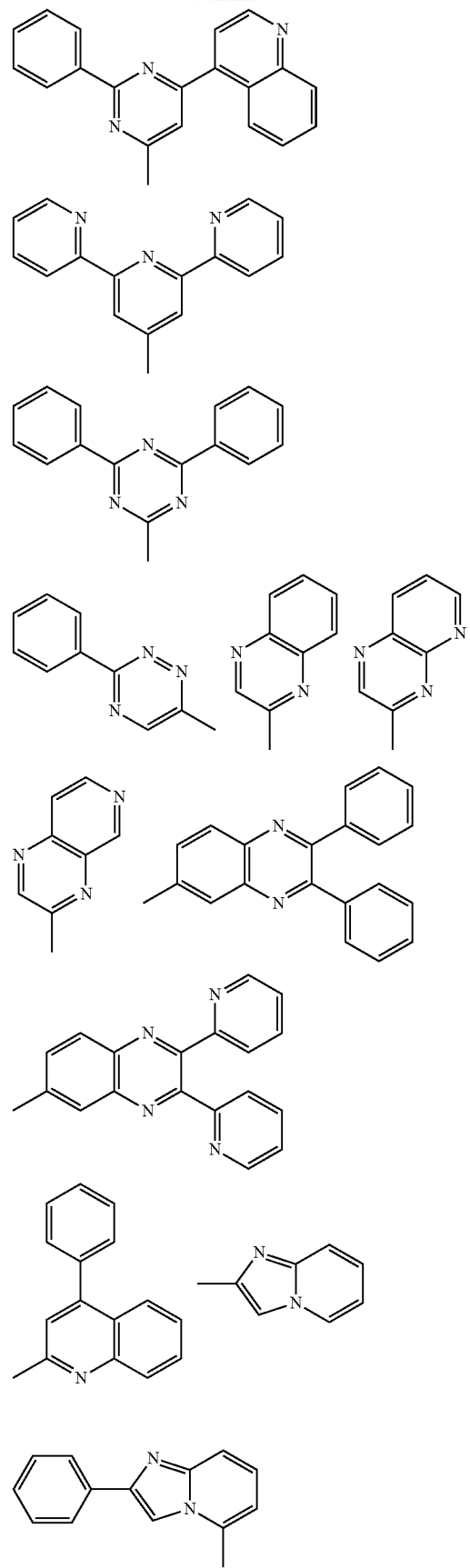

-continued

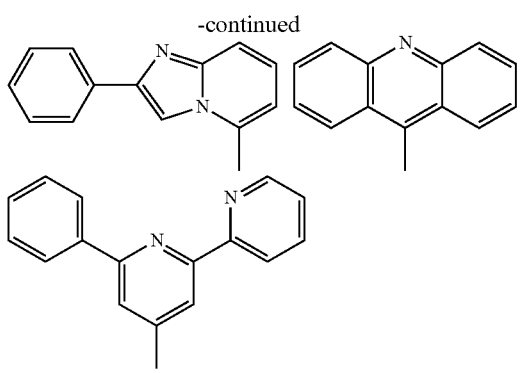

$L^1$ in the above formula (D1) is selected from the following groups, for example.

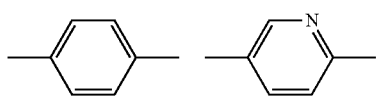

$Ar^1$ in the formula (D1) is selected from arylanthranyl groups represented by the following formulas (D2) and (D3):

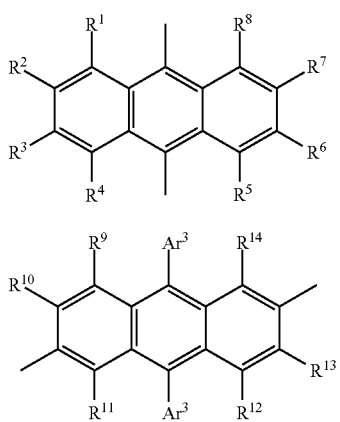

In the formulas (D2) and (D3), $R^1$ to $R^{14}$ are independently a hydrogen atom, a deuterium atom, a halogen atom, an alkyl group having 1 to 20 carbon atoms, an alkoxy group having 1 to 20 carbon atoms, an aryloxy group having 6 to 40 carbon atoms, a substituted or unsubstituted aromatic hydrocarbon group or fused aromatic hydrocarbon group having 6 to 40 carbon atoms, or a substituted or unsubstituted aromatic heterocyclic group or fused aromatic heterocyclic group having 3 to 40 carbon atoms; and $Ar^3$ is a substituted or unsubstituted aromatic hydrocarbon group or fused aromatic hydrocarbon group having 6 to 40 carbon atoms or a substituted or unsubstituted aromatic heterocyclic group or fused aromatic heterocyclic group having 3 to 40 carbon atoms. All of $R^1$ to $R^8$ may be a nitrogen-containing heterocyclic derivative that may be a hydrogen atom or a deuterium atom.

$Ar^2$ in the formula (D1) is selected from the following group, for example.

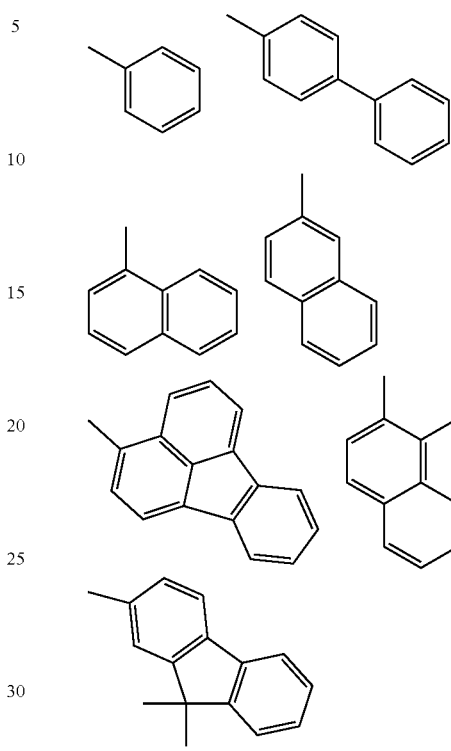

Other than those mentioned above, the following compound can be preferably used for the nitrogen-containing aromatic polycyclic organic compound as the electron-transmitting compound.

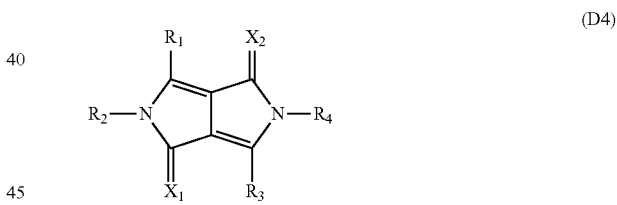

In the formula (D4), $R_1$ to $R_4$ are independently a hydrogen atom, a deuterium atom, a substituted or unsubstituted aliphatic group having 1 to 20 carbon atoms, a substituted or unsubstituted alicyclic group having 3 to 20 carbon atoms, a substituted or unsubstituted aromatic ring group having 6 to 50 carbon atoms, or a substituted or unsubstituted heterocyclic group having 3 to 50 carbon atoms; and $X_1$ and $X_2$ are independently an oxygen atom, a sulfur atom or a dicyanomethylene group.

The following compound can also be preferably used for the electron-transmitting compound.

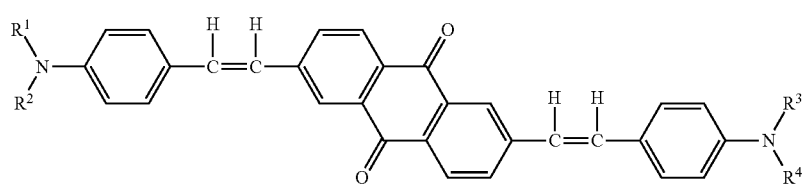

In the formula (D5), $R^1$, $R^2$, $R^3$ and $R^4$, which may be the same or different, are an aromatic hydrocarbon group or a fused aromatic hydrocarbon group represented by the following formula (D6).

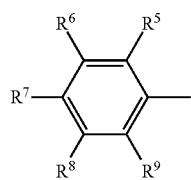

(D6)

In the formula (D6), $R^5$, $R^6$, $R^7$, $R^8$ and $R^9$, which may be the same or different, are a hydrogen atom, a deuterium atom, a saturated or unsaturated alkoxy group, a saturated or unsaturated alkyl group having 1 to 20 carbon atoms, an amino group or an alkylamino group having 1 to 20 carbon atoms. At least one of $R^5$, $R^8$, $R^7$, $R^8$ and $R^9$ is a group other than a hydrogen atom or a deuterium atom.

The electron-transmitting compound may be a polymer compound containing the nitrogen-containing heterocyclic group or a nitrogen-containing heterocyclic derivative.

It is particularly preferred that the electron-transporting layer of the organic EL device of the invention contain at least one of nitrogen-containing heterocyclic derivatives represented by the following formulas (E) to (G):

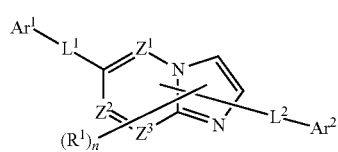

(E)

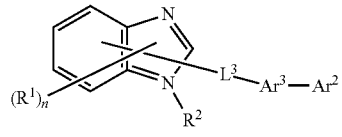

(F)

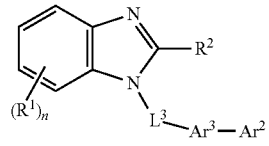

(G)

In the formulas (E) to (G), $Z^1$, $Z^2$ and $Z^3$ are independently a nitrogen atom or a carbon atom.

$R^1$ and $R^2$ are independently a substituted or unsubstituted aryl group having 6 to 50 ring carbon atoms, a substituted or unsubstituted heteroaryl group having 5 to 50 ring atoms, a substituted or unsubstituted alkyl group having 1 to 20 carbon atoms, or a substituted or unsubstituted haloalkly group having 1 to 20 carbon atoms or a substituted or unsubstituted alkoxy group having 1 to 20 carbon atoms.

n represents an integer of 0 to 5 and when n is an integer of 2 or more, plural $R^1$s may be the same or different. Adjacent two groups of $R^1$ may be bonded with each other to form a substituted or unsubstituted hydrocarbon ring.

$Ar^1$ is a substituted or unsubstituted aryl group having 6 to 50 carbon atoms or a substituted or unsubstituted heteroaryl group having 5 to 50 ring atoms.

$Ar^2$ is a hydrogen atom, a substituted or unsubstituted alkyl group having 1 to 20 carbon atoms, a substituted or unsubstituted haloalkyl group having 1 to 20 carbon atoms, a substituted or unsubstituted alkoxy group having 1 to 20 carbon atoms, a substituted or unsubstituted aryl group having 6 to 50 ring carbon atoms or a substituted or unsubstituted heteroaryl group having 5 to 50 ring atoms.

Any one of $Ar^1$ and $Ar^2$ is a substituted or unsubstituted fused aromatic hydrocarbon group having 10 to 50 ring carbon atoms or a substituted or unsubstituted fused aromatic heterocyclic group having 9 to 50 ring atoms.

$Ar^3$ is a substituted or unsubstituted arylene group having 6 to 50 ring carbon atoms or a substituted or unsubstituted heteroarylene group having 5 to 50 ring atoms.

$L^1$, $L^2$ and $L^3$ are independently a single bond, a substituted or unsubstituted arylene group having 6 to 50 ring carbon atoms or a substituted or unsubstituted divalent fused aromatic heterocyclic group having 9 to 50 ring atoms.

As the aryl group having 6 to 50 ring carbon atoms, a phenyl group, a naphthyl group, an anthryl group, a phenanthryl group, a naphthacenyl group, a chrycenyl group, a pyrenyl group, a biphenyl group, a terphenyl group, a tolyl group, a fluoranthenyl group, a fluorenyl group, or the like can be given.

As the heteroaryl group having 5 to 50 ring atoms, a pyrrolyl group, a furyl group, a thienyl group, a silolyl group, a pyridyl group, a quinolyl group, an isoquinolyl group, a benzofuryl group, an imidazolyl group, a pyrimidyl group, a carbazolyl group, a selenophenyl group, an oxadiazolyl group, a triazolyl group, a pyrazinyl group, a pyridazinyl group, a triazinyl group, a quinoxalinyl group, an acrydinyl group, an imidazo[1,2-a]pyridinyl group, an imidazo[1,2-a]pyrimidinyl group, or the like can be given.

As the alkyl group having 1 to 20 carbon atoms, a methyl group, an ethyl group, a propyl group, a butyl group, a pentyl group, a hexyl group or the like can be given.

As the haloalkyl group having 1 to 20 carbon atoms, a group obtained by substituting one or two or more hydrogen atoms of the alkyl group with at least one halogen atoms selected from fluorine, chlorine, iodine and bromine can be given.

As the alkoxy group having 1 to 20 carbon atoms, a group having the above-mentioned alkyl group as an alkyl part can be given.

As the arylene group having 6 to 50 ring carbon atoms, a group obtained by removing one hydrogen atom from the aryl group can be given.

As the divalent fused aromatic heterocyclic group having 9 to 50 ring atoms, a group obtained by removing one hydrogen atom from the fused aromatic heterocyclic group stated as the heteroaryl group can be given.

Although the thickness of the electron-transporting layer is not particularly restricted, the thickness is preferably 1 nm to 100 nm.

The electron-injecting layer which can be provided in adjacent to the electron-transporting layer preferably contains an inorganic compound such as an insulator or a semiconductor in addition to the nitrogen-containing cyclic derivative. Such an insulator or a semiconductor, when contained in the electron-injecting layer, can effectively prevent a current leak, thereby enhancing electron injection properties.

As the insulator, it is preferable to use at least one metal compound selected from the group consisting of an alkali metal chalcogenide, an alkaline earth metal chalcogenide, a halide of an alkali metal and a halide of an alkaline earth metal. When the electron-injecting layer is formed from the alkaline metal chalcogenide or the like, the electron-injecting properties can preferably be further enhanced. Specifically, preferred examples of the alkali metal chalcogenide are $Li_2O$, $K_2O$, $Na_2S$, $Na_2Se$ and $Na_2O$, while preferable example of the alkaline earth metal chalcogenide are CaO, BaO, SrO, BeO, BaS and CaSe. Preferred examples of the halide of the alkali metal include LiF, NaF, KF, LiCl, KCl and NaCl. Preferred examples of the halide of the alkaline earth metal are fluorides such as $CaF_2$, $BaF_2$, $SrF_2$, $MgF_2$ and $BeF_2$, and halides other than the fluoride.

Examples of the semiconductor are one of or a combination of two or more of an oxide, a nitride or an oxidized nitride containing at least one element selected from Ba, Ca, Sr, Yb, Al, Ga, In, Li, Na, Cd, Mg, Si, Ta, Sb and Zn. An inorganic compound for forming the electron-injecting layer is preferably a microcrystalline or amorphous insulative firm. When the electron-injecting layer is formed of such an insulative film, more uniform thin film can be formed, thereby reducing pixel defects such as a dark spot. Examples of such an inorganic compound include an alkali metal chalcogenide, an alkaline earth metal chalcogenide, a halide of an alkali metal and a halide of an alkaline earth metal.

When such an insulator or a semiconductor is used, the preferable thickness of the layer is about 0.1 nm to 15 nm. The electron-injecting layer of the invention preferably contains the above-mentioned electron-donating dopant.

(Hole-Transporting Layer)

The hole-transporting layer is an organic layer formed between the emitting layer and the anode, and has a function of transporting holes from the anode to the emitting layer. If the hole-transporting layer is formed of a plurality of layers, an organic layer nearer to the anode may often be defined as the hole-injecting layer. The hole-injecting layer has a function of injecting holes from the anode to an organic layer unit efficiently.

As the other materials for forming the hole-transporting layer, an aromatic amine compound, e.g. an aromatic amine derivative represented by the following formula (H), can preferably used.

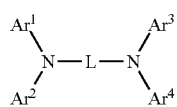
(H)

In the above formula (H), $Ar^1$ to $Ar^4$ are a substituted or unsubstituted aromatic hydrocarbon group or fused aromatic hydrocarbon group having 6 to 50 ring carbon atoms, a substituted or unsubstituted aromatic heterocyclic group or fused aromatic heterocyclic group having 5 to 50 ring atoms or a group obtained by bonding these aromatic hydrocarbon group or fused aromatic hydrocarbon group with an aromatic heterocyclic group or a fused aromatic heterocyclic group.

Further, in the above formula (H), L is a substituted or unsubstituted aromatic hydrocarbon group or fused aromatic hydrocarbon group having 6 to 50 ring carbon atoms, or a substituted or unsubstituted aromatic hydrocarbon group or fused aromatic heterocyclic group having 5 to 50 ring atoms.

Specific examples of the compound represented by the formula (H) are given below.

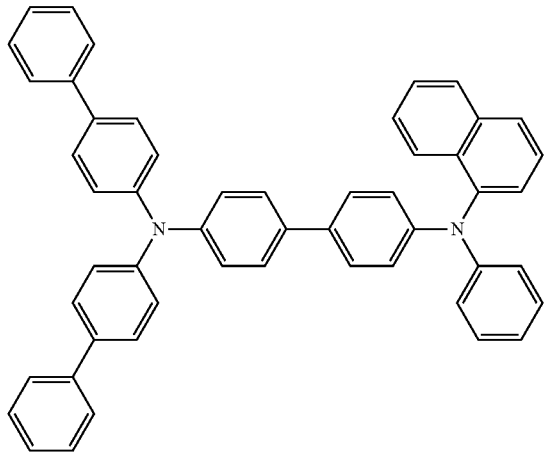

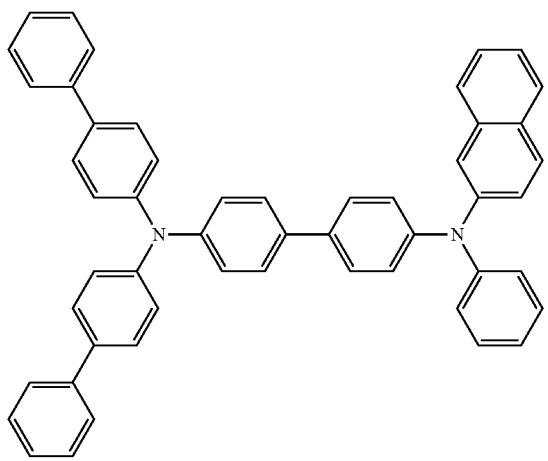

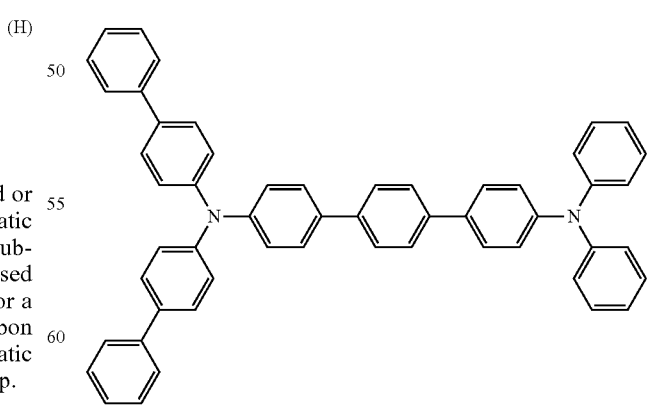

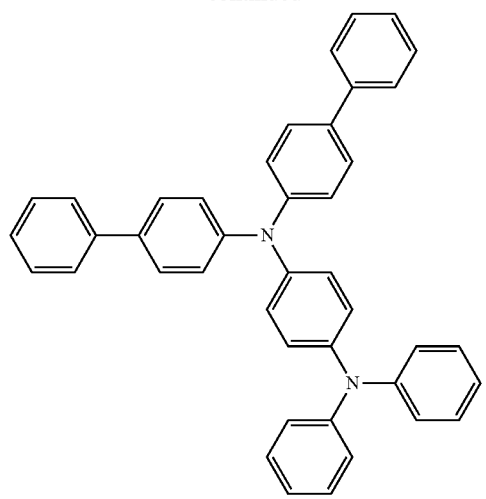
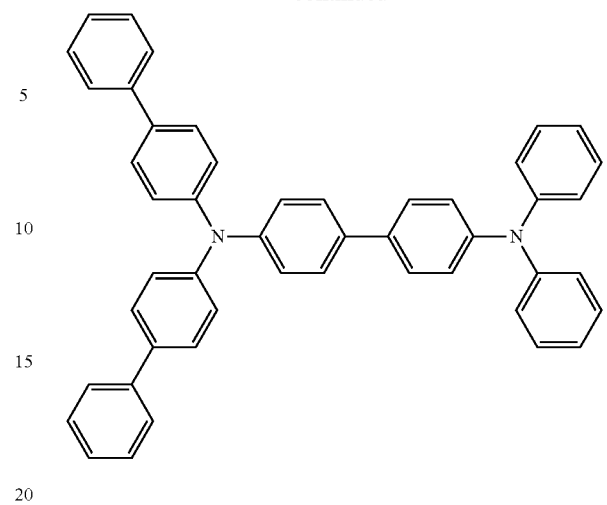
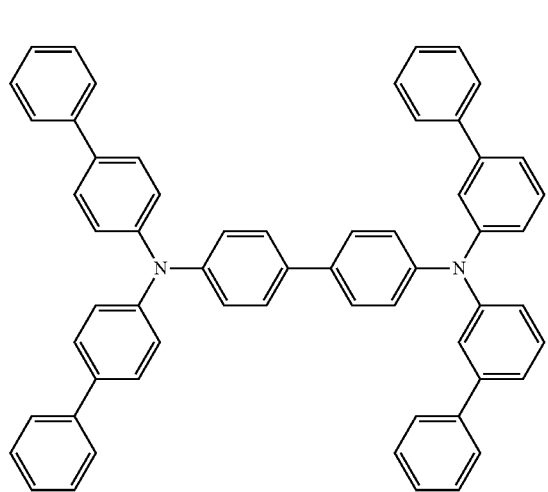
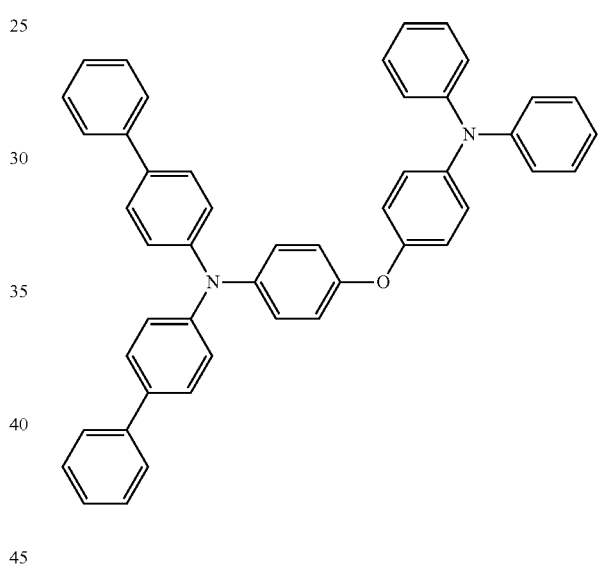
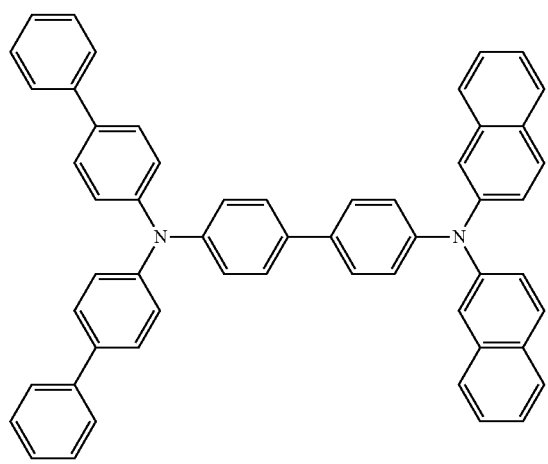
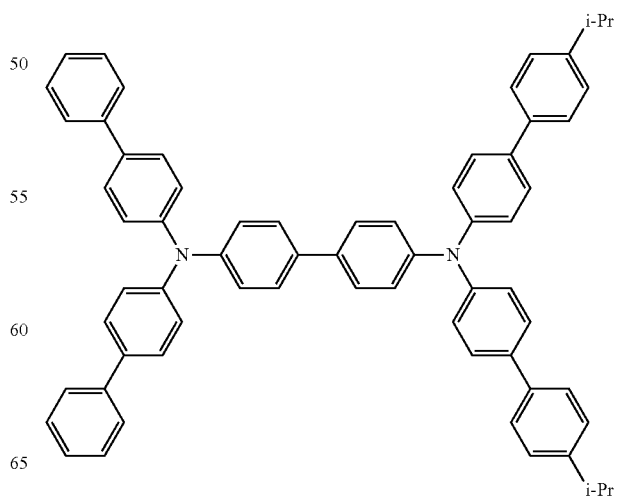

-continued
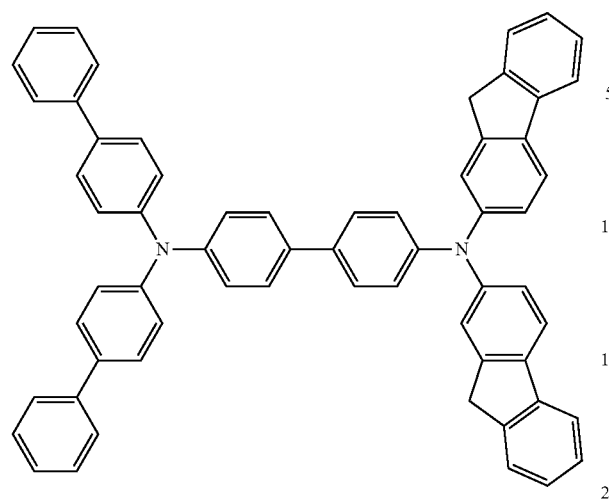
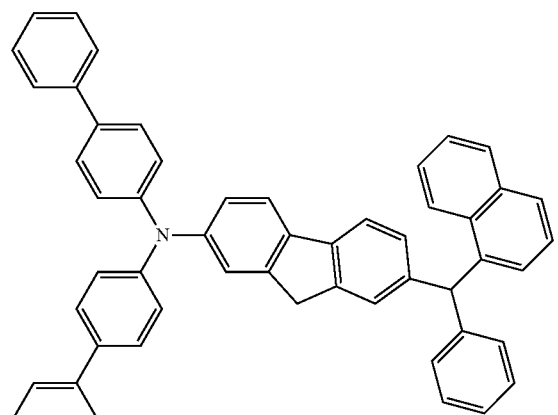
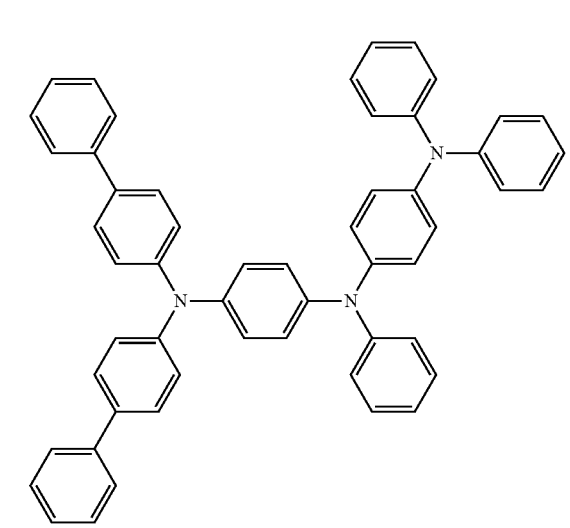
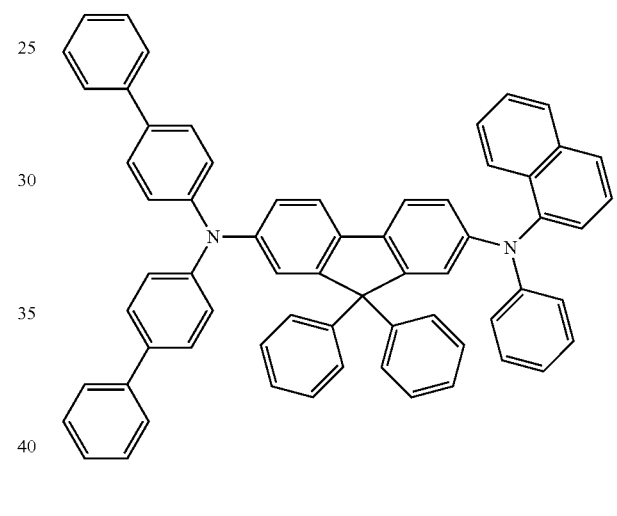
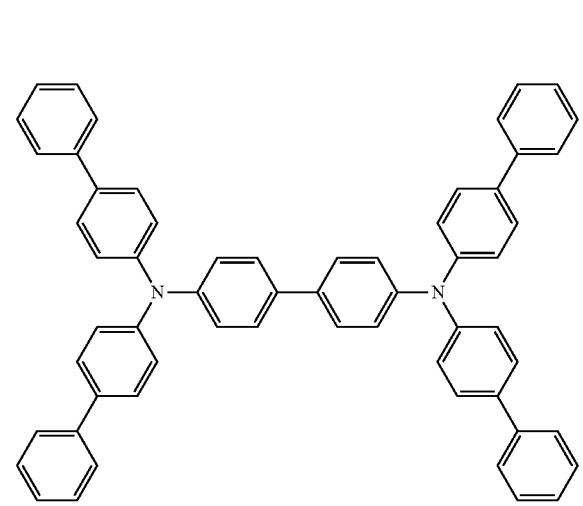
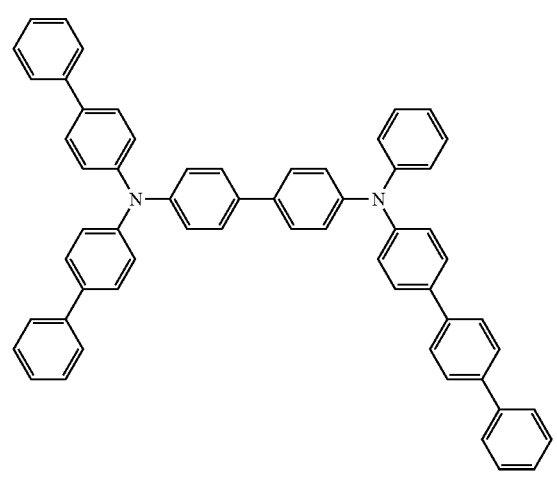

67
-continued
68
-continued
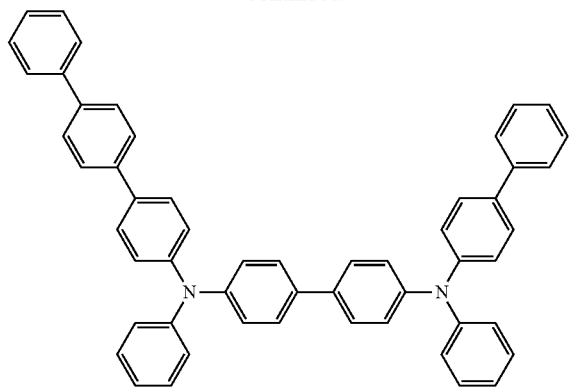
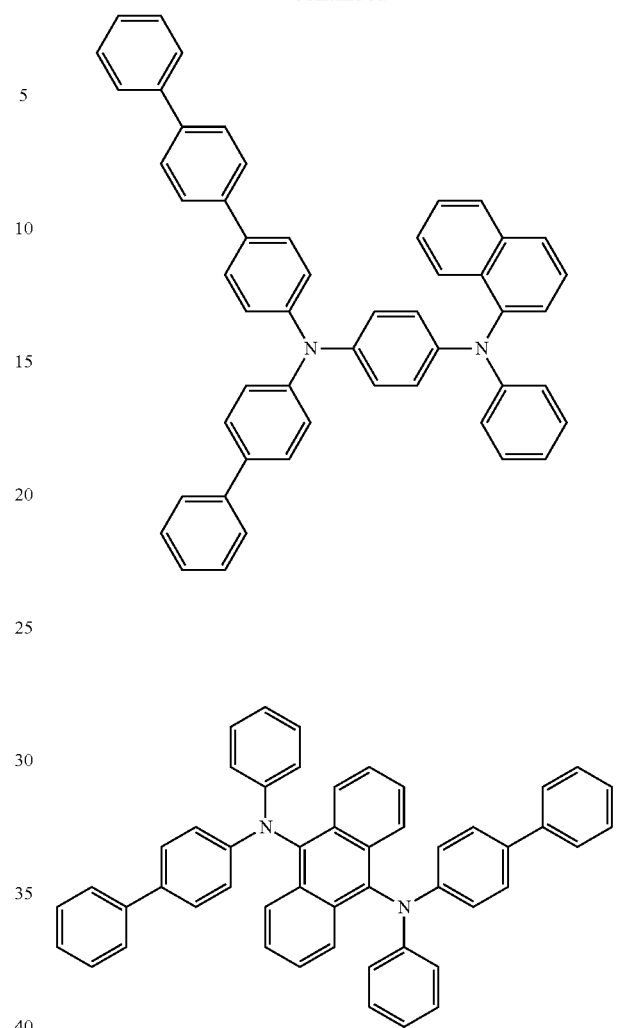
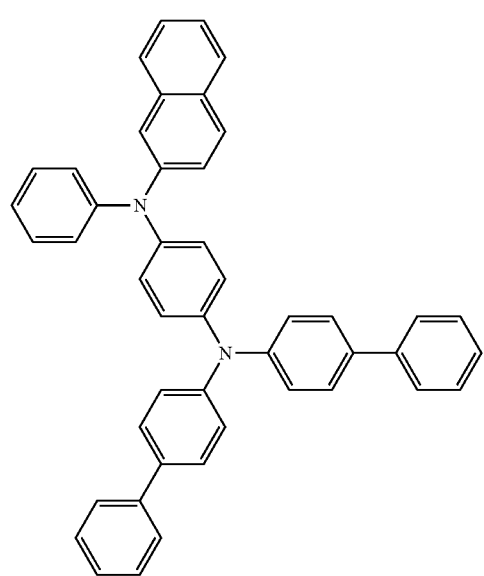
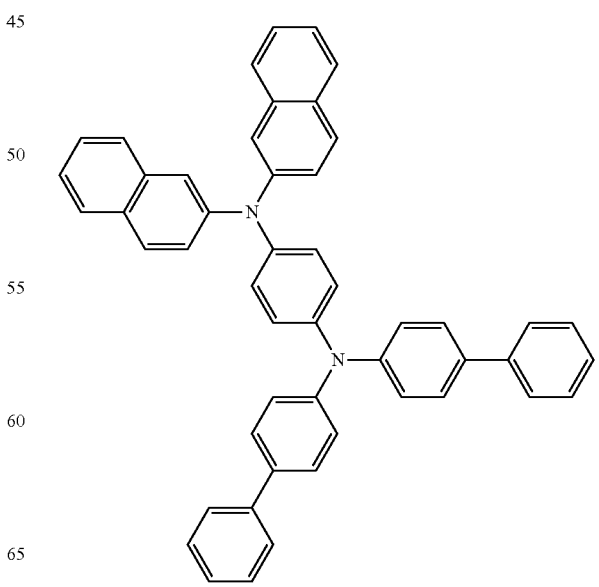

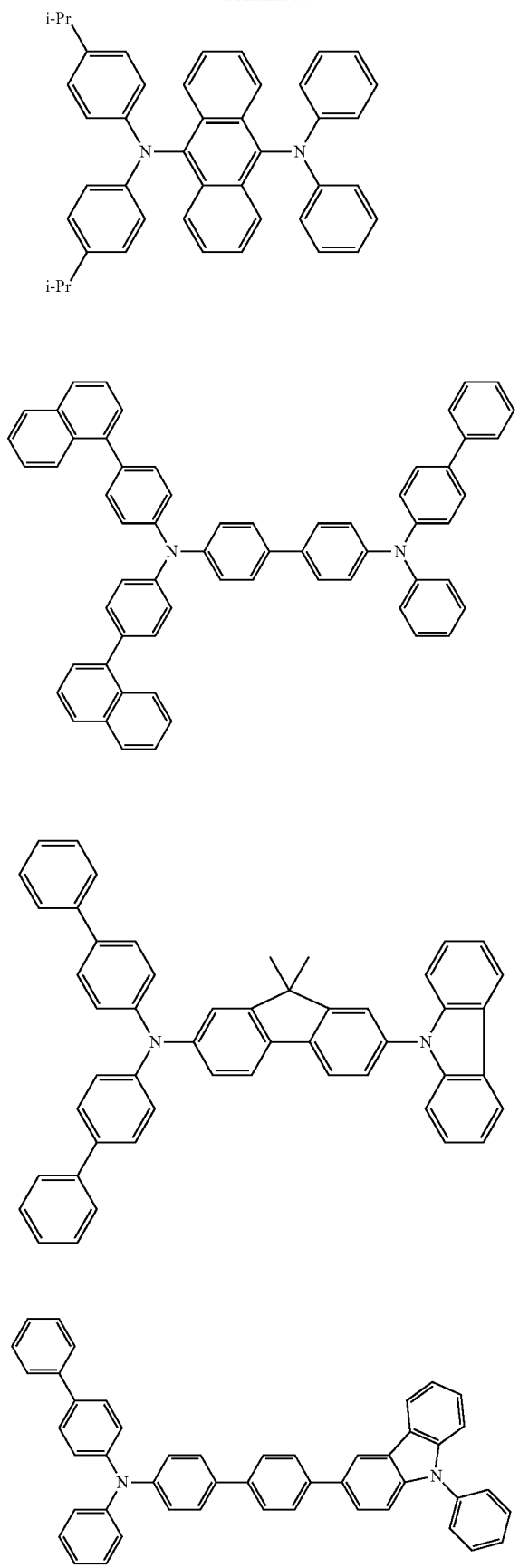

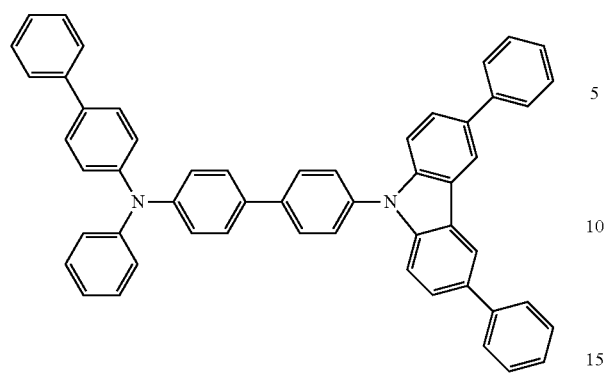
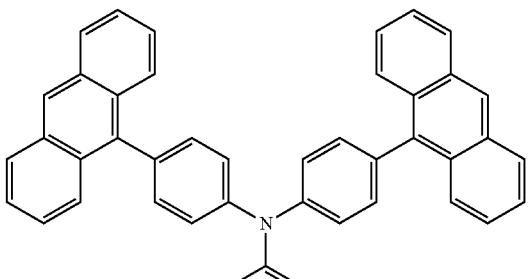
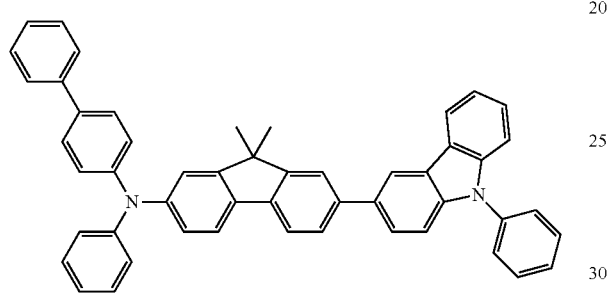
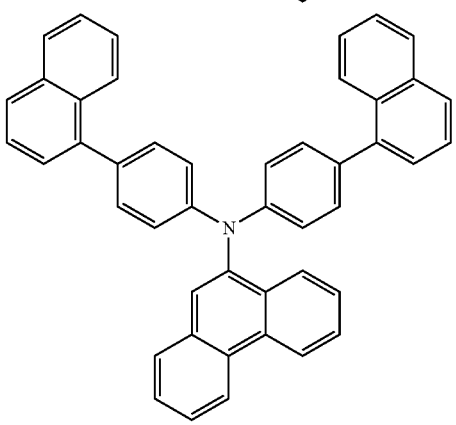
The aromatic amine represented by the following formula (J) can preferably be used for the formation of the hole-transporting layer.
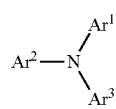
(J)
In the above formula (J), $Ar^1$ to $Ar^3$ are as defined as $Ar^1$ to $Ar^4$ in the formula (H). Specific examples of the compound represented by the formula (J) are shown below, though not limited thereto.
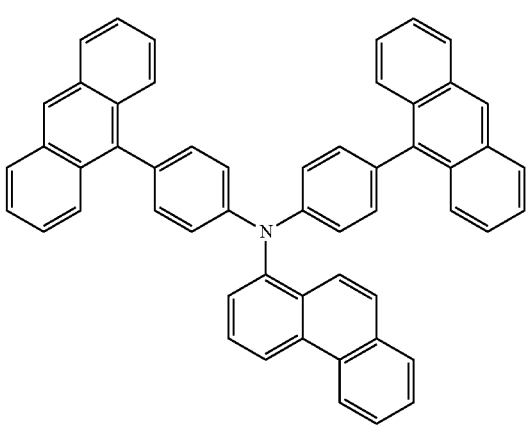
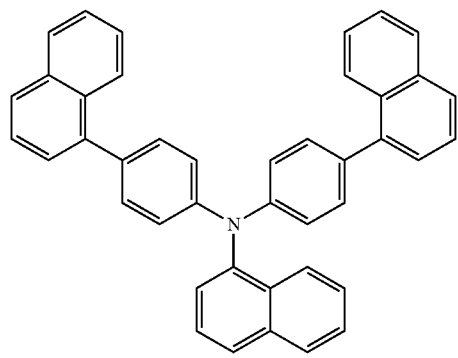
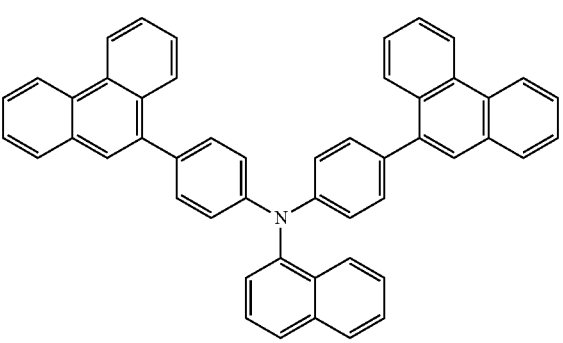

73
-continued
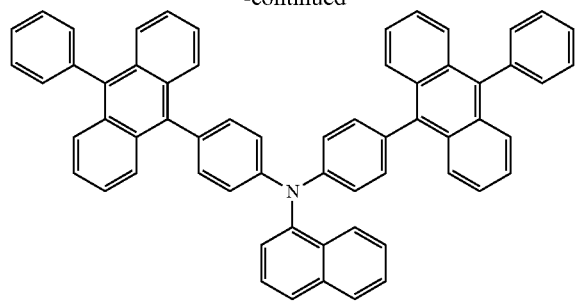
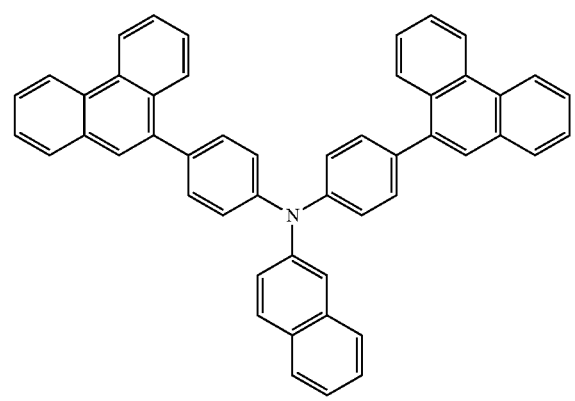
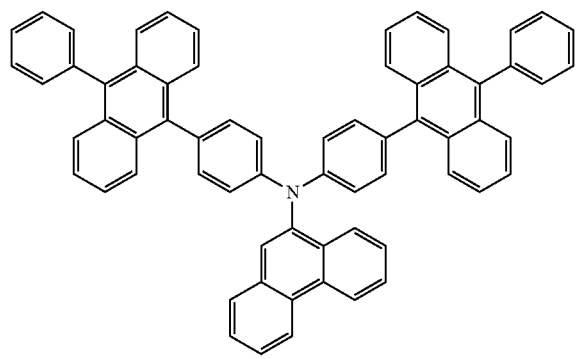
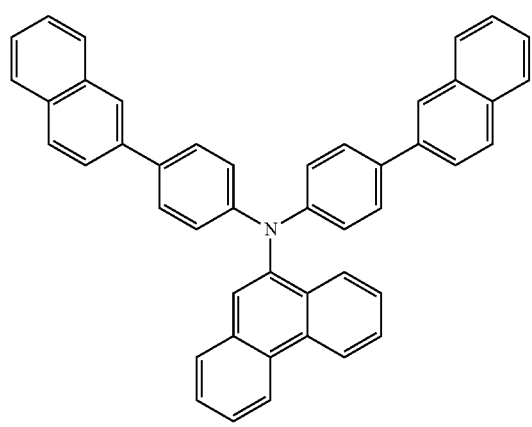
74
-continued
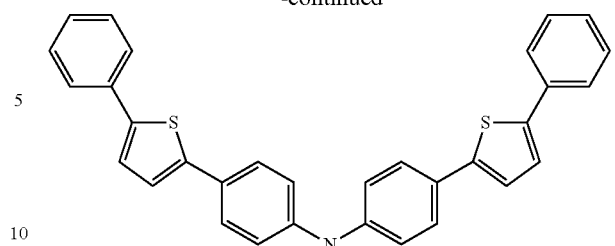
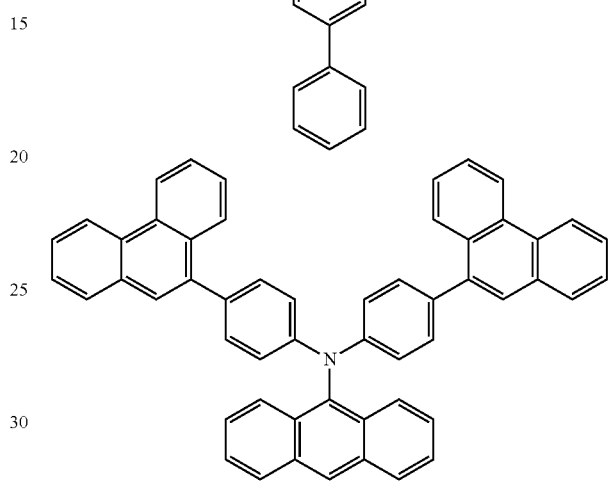
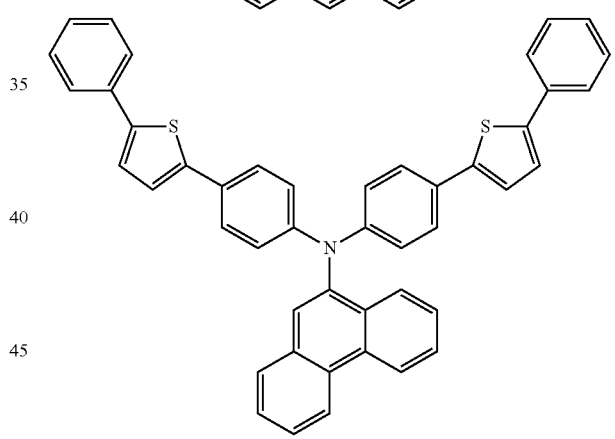
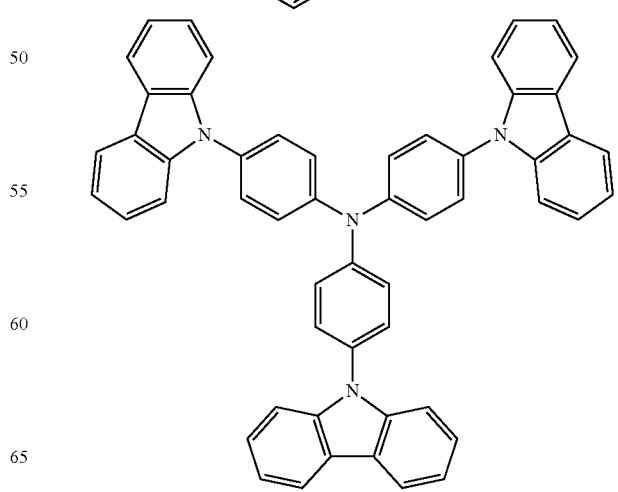

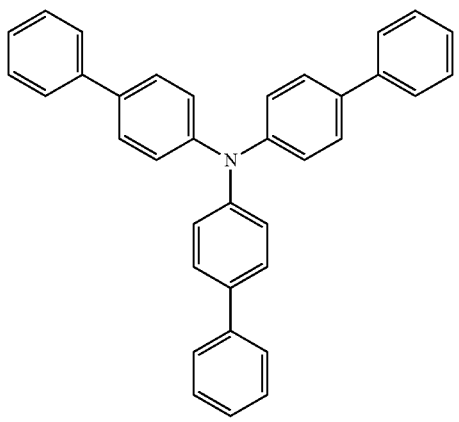

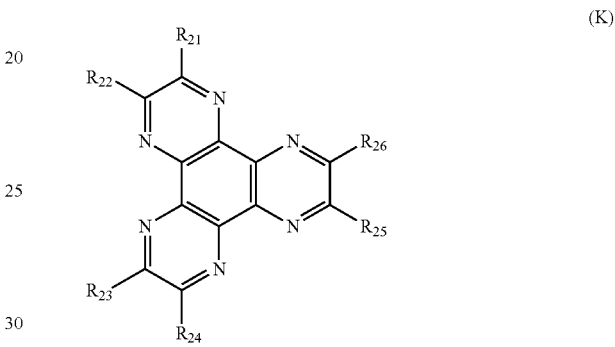

The hole-transporting layer of the organic EL device of the invention may be of a two-layer structure of the first hole-transporting layer (anode side) and the second hole-transporting layer (cathode side).

Although no specific restrictions are imposed on the thickness of the hole-transporting layer, the thickness is preferably 10 to 200 nm.

In the organic EL device of the invention, a layer containing an acceptor material may be connected to the side of the hole-transporting layer or the first hole-transporting layer nearer to the anode. By such a configuration, a decrease in driving voltage or reduction in production cost can be expected.

As the acceptor material, a compound represented by the following formula (K) is preferable.

(K)

[Structure of formula (K) with $R_{21}$ to $R_{26}$ substituents on a pyrazine-fused ring system]

In the above formula (K), $R_{21}$ to $R_{26}$, which may be the same or different, are independently a cyano group, —$CONH_2$, a carboxyl group or —$COOR_{27}$ ($R_{27}$ is an alkyl group having 1 to 20 carbon atoms or a cycloalkyl group having 3 to 20 carbon atoms). One or two or more pairs of $R_{21}$ and $R_{22}$, $R_{23}$ and $R_{24}$ and $R_{25}$ and $R_{26}$ may be bonded to form a group represented by —CO—O—CO—.

As examples of $R_{27}$, a methyl group, an ethyl group, an n-propyl group, an isopropyl group, an n-butyl group, an isobutyl group, a t-butyl group, a cyclopentyl group, a cyclohexyl group or the like can be given.

The thickness of the layer containing an accepter material is not particularly restricted, but it is preferably 5 to 20 nm.

(n/p Doping)

In the above-mentioned hole-transporting layer or the electron-transporting layer, as stated in the U.S. Pat. No. 3,695,714, carrier injection properties can be adjusted by doping (n) of a donating material or doping (p) of an accepter material.

As the representative example of the n-doping, a method in which an electron-transporting material is doped with a metal such as Li and Cs can be given. As the representative example of the p-doping, a method in which a hole-transporting material is doped with an accepter material such as $F_4TCNQ$ (2,3,5,6-tetrafluoro-7,7,8,8-tetracyanoquinodimethane) can be given.

(Space Layer)

The space layer is a layer provided, when a fluorescent layer and a phosphorescent layer are stacked, between the fluorescent layer and the phosphorescent layer in order to prevent diffusion of excitons generated in the phosphorescent layer to the fluorescent layer or in order to adjust carrier balance. The space layer may be provided between the plural phosphorescent layers.

Due to the provision between the emitting layers, the space layer is preferably formed of a material which has both electron-transporting properties and hole-transporting properties. Further, in order to prevent diffusion of triplet energy in the adjacent phosphorescent layers, it is preferred that the triplet energy be 2.6 eV or more. As the material used in the space layer, the same materials as those used in the above-mentioned hole-transporting layer can be given.

(Blocking Layer)

In the organic EL device of the invention, it is preferred that a blocking layer such as an electron-blocking layer, a hole-blocking layer and a triplet-blocking layer be provided in a part adjacent to the emitting layer. Here, the electron-blocking layer is a layer that prevents leakage of electrons from the emitting layer to the hole-transporting layer and the hole-blocking layer is a layer that prevents leakage of holes from the emitting layer to the electron-transporting layer.

The triplet-blocking layer has a function of preventing triplet excitons generated in the emitting layer from diffusing to layers in the vicinity thereof thereby to confine triplet excitons in the emitting layer, whereby energy deactivation of triplet excitons on the molecules other than the emitting dopant molecules in the electron-transporting layer is suppressed.

If a triplet-blocking layer is provided, in a phosphorescent device, the following is assumed. That is, when the triplet energy of the phosphorescent dopant in the emitting layer is taken as $E^T_d$ and the triplet energy of the compound used as the triplet-blocking layer is taken as $E^T_{TB}$, if the relationship $E^T_d<E^T_{TB}$ is satisfied, the triplet excitons of the phosphorescent dopant are confined (i.e. cannot be moved to other molecule) in respect of energy. As a result, energy deactivation other than emission of the dopant becomes impossible, whereby highly efficient emission is realized. However, it is believed that, when the relationship $E^T_d<E^T_{TB}$ is satisfied, if the energy difference $\Delta E^T=E^T_{TB}-E^T_d$ small, under the circumstance of around room temperature at which the device is actually driven, due to the thermal energy of the environment, triplet excitons can move to other molecules endothermically by overcoming the difference $\Delta E^T$. In particular, since the life of excitons is longer in the case of phosphorescent emission as compared with fluorescent emission, effects of the endothermic exciton movement process are tend to be exhibited relatively. This energy difference $\Delta E^T$ is preferably large in relation to the thermal energy at room temperature. It is further preferred that the energy difference be 0.1 eV, with 0.2 eV or more being particularly preferable. On the other hand, in a fluorescent device, the material for an organic EL device of the invention can be used as a triplet-blocking layer of a TTF device configuration as disclosed in WO2010/134350A1.

It is desired that the electron mobility of the material constituting the triplet blocking layer be $10^{-6}$ cm$^2$/Vs or more in an electric field intensity range of 0.04 to 0.5 MV/cm. As the method for measuring the electron mobility of an organic material, several methods including a Time of Flight method are known. Here, the electron mobility is referred to as the electron mobility determined by the impedance spectroscopy.

The electron mobility in the electron-injecting layer is desirably $10^{-6}$ cm$^2$/Vs or more in an electric field intensity range of 0.04 to 0.5 MV/cm. By this electron mobility value, electron injection from the cathode to the electron-transporting layer is promoted, and consequently, electron injection from the cathode to adjacent blocking layer or the emitting layer is promoted, whereby driving at a lower voltage is enabled.

EXAMPLES

The invention will be explained in more detail with reference to Examples below. However the invention is not limited to the following Examples.

<Synthesis of Material for Organic EL Device>

Synthesis 1 (Synthesis of Compound H1)

(1) Synthesis of Intermediate 1

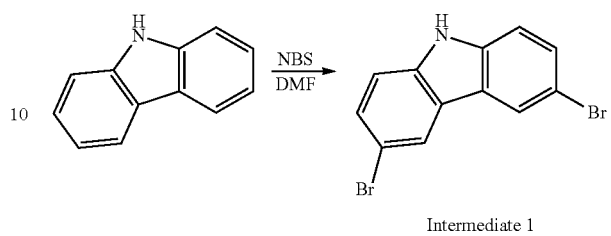

Intermediate 1

Under an argon stream, carbazole (56 g, 334 mmol) and N,N-dimethylformamide (DMF; 250 mL) were placed in a recovery flask having 1000 mL and cooled to −7° C. in an ice bath (sodium chloride added). To the mixture, an N,N-dimethylformamide solution (200 mL) of N-bromosuccinimide (NBS; 119 g, 668 mmol) was added dropwise, and the mixture was stirred at −7° C. for 4 hours.

After clean water was added to the reaction solution and the mixture was heated to room temperature, precipitated solids were taken out by filtration. The recrystallization of the solids obtained was repeated with toluene, thereby to obtain Intermediate 1 (71 g, yield: 65%). By FD-MS (Field Desorption Mass Spectrometry) analysis, the compound obtained was confirmed to be Intermediate 1.

(2) Synthesis of Intermediate 2

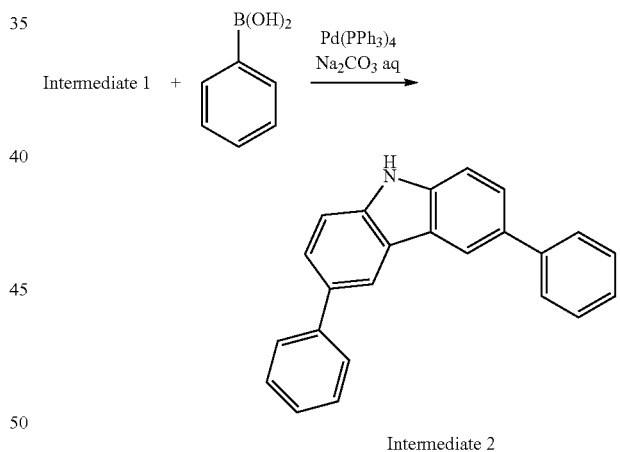

Intermediate 2

Under an argon stream, in a recovery flask having 2000 mL, Intermediate 1 (33 g, 102 mmol), phenylboronic acid (27 g, 221 mmol), tetrakis(triphenylphosphine)palladium (Pd(PPh$_3$)$_4$; 7.0 g, 6.1 mmol), 1,2-dimethoxyethane (600 mL) and 2M sodium carbonate solution (200 mL) were sequentially charged and the mixture was heated under reflux for 8 hours.

After the reaction solution was heated to room temperature, the organic phase was separated, and the organic solvent was distilled away under reduced pressure. The residue obtained was purified by means of silica gel column chromatography to obtain Intermediate 2 (19 g, yield: 58%). By FD-MS analysis, the compound obtained was confirmed to be Intermediate 2.

(3) Synthesis of Intermediate 3

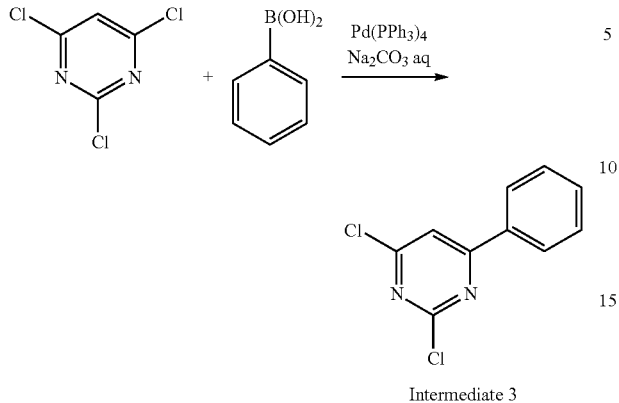

Intermediate 3

Intermediate 3 was synthesized in the same manner as in the synthesis of Intermediate 1, except that 2,4,6-trichloropyrimidine was used instead of Intermediate 1. By FD-MS analysis, the compound obtained was confirmed to be Intermediate 3.

(4) Synthesis of Intermediate 4

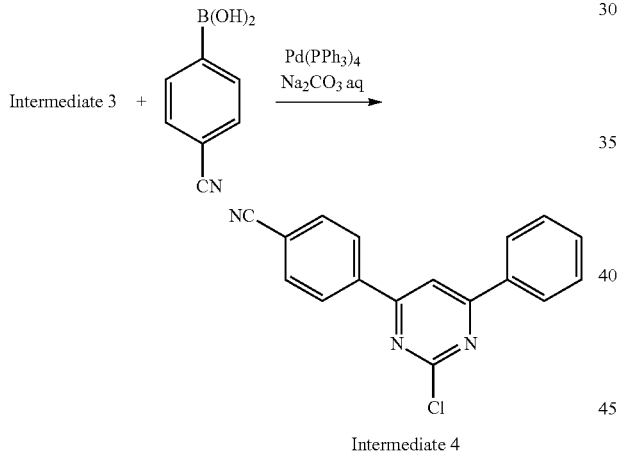

Intermediate 4

Intermediate 4 was synthesized in the same manner as in the synthesis of Intermediate 2, except that Intermediate 3 was used instead of Intermediate 1, and 4-cyanophenylboronic acid was used instead of phenylboronic acid. By FD-MS analysis, the compound obtained was confirmed to be Intermediate 4.

(5) Synthesis of Intermediate 5

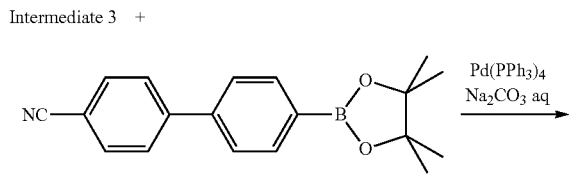

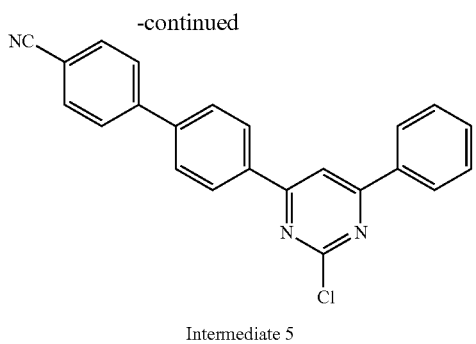

Intermediate 5

Intermediate 5 was synthesized in the same manner as in the synthesis of Intermediate 2, except that Intermediate 3 was used instead of Intermediate 1, and 4'-(4,4,5,5-tetramethyl-1,3,2-dioxaborolane-2-yl) biphenyl-4-carbonitrile was used instead of phenylboronic acid. By FD-MS analysis, the compound obtained was confirmed to be Intermediate 5.

Synthesis Example 1

Synthesis of Compound H1

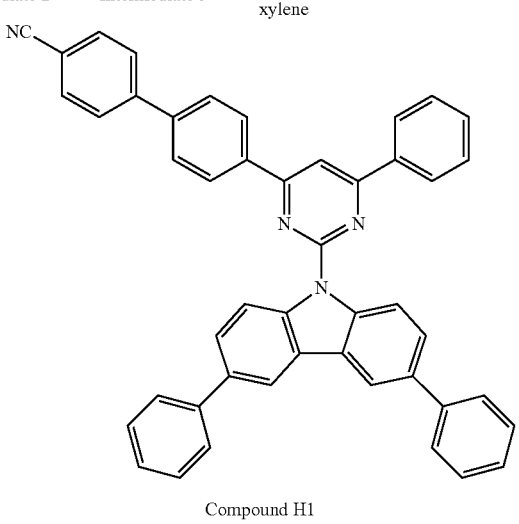

Compound H1

Under an argon stream, Intermediate 2 (2.3 g, 7.2 mmol), Intermediate 5 (3.2 g, 8.6 mmol), tris(dibenzilidene acetone) dipalladium ($Pd_2(dba)_3$; 0.26 g, 0.29 mmol), tri-t-butylphosphonium tetrafluoro borate ($P(tBu)_3 \cdot HBF_4$; 0.21 g, 0.72 mmol), sodium t-butoxide ($NaO_tBu$; 1.4 g, 14 mmol) and anhydrous xylene (40 mL) were sequentially charged and the mixture was heated under reflux for 8 hours.

After the reaction solution was heated to room temperature, the organic phase was separated, and the organic solvent was distilled away under reduced pressure. The residue obtained was purified by means of silica gel column chromatography to obtain 3.6 g of yellowish white solids (Compound H1).

The result of FD-MS for the compound obtained is shown below.

FDMS, calcd for $C_{47}H_{30}N_4=650$. found m/z=650 (M+).

Synthesis Example 2

Synthesis of Compound H2

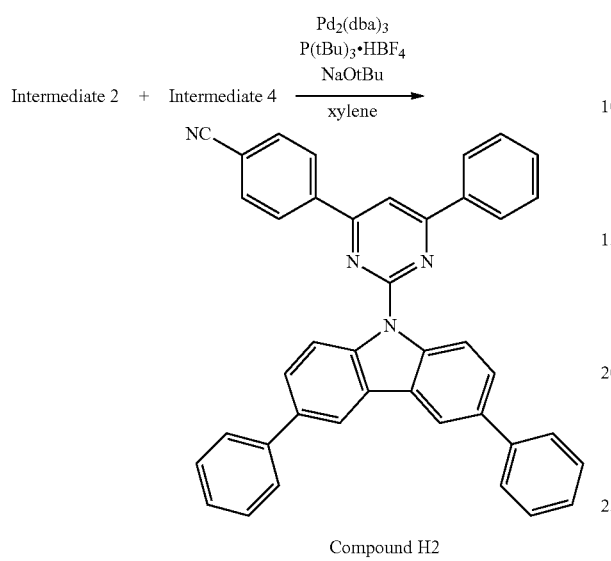

Compound H2

Compound H2 was synthesized in the same manner as in the synthesis of Compound H1 in Synthesis Example 1 (6), except that Intermediate 4 was used instead of Intermediate 5.

The result of FD-MS for the compound obtained is shown below.

FDMS, calcd for C41H26N4=574. found m/z=574 (M+).

Preparation of Organic EL Device and Evaluation of Emitting Performance

Example 1

Fabrication of Organic EL Device

A glass substrate, measuring 25 mm×75 mm×1.1 mm thick, with an ITO transparent electrode (manufactured by Geomatics Co.) was subjected to ultrasonic cleaning in isopropyl alcohol for 5 minutes and then UV ozone cleaning for 30 minutes.

The cleaned glass substrate with transparent electrode lines was mounted on a substrate holder in a vacuum deposition device. First, a 5 nm thick film of the following acceptor compound C-1 was formed by deposition on the surface where the transparent electrode lines were formed, so as to cover the transparent electrode. On the film of compound C-1, as a first hole-transporting material, the following aromatic amine derivative (compound X1) was deposited to form a first hole-transporting layer having a thickness of 65 nm. Subsequent to the formation of the first hole-transporting layer, as a second hole-transporting material, the following aromatic amine derivative (compound X2) was deposited to form a second hole-transporting layer having a thickness of 10 nm.

Furthermore, on the second hole-transporting layer, compound H1 as a host material and the following compound Ir(bzq)$_3$ as a phosphorescent material were co-deposited to form a phosphorescent layer having a thickness of 25 nm. The concentration of compound Ir(bzq)$_3$ in an emitting layer was 10.0 mass %. The co-deposited layer functions as an emitting layer.

Subsequent to the formation of the emitting layer, the following compound ET was deposited to form a 35 nm thick film. The film of compound ET functions as an electron-transporting layer.

Next, as an electron-injecting electrode (cathode), LiF was deposited at a film-formation speed of 0.1 Å/min to form a 1 nm thick film. On the LiF film, a metal Al was deposited to form an 80 nm thick metal cathode, thereby fabricating an organic EL device.

For the organic EL device, the performance by constant current drive at an initial luminance of 10000 cd/m$^2$ (80% life (the time it takes for the luminance decreases to 80% of the initial luminance)) was evaluated. The results are shown in Table 1.

The compounds used in Examples and Comparative Examples are shown below.

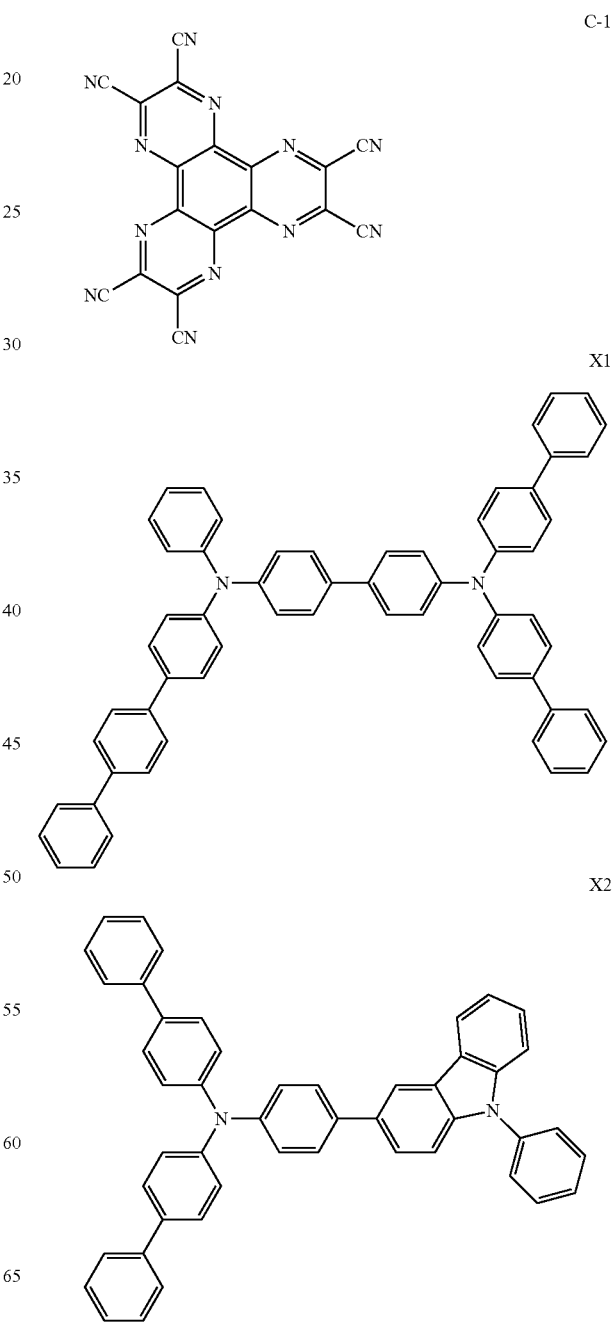

-continued

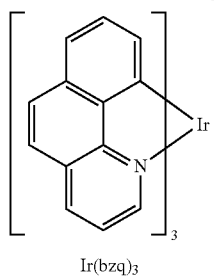

Ir(bzq)₃

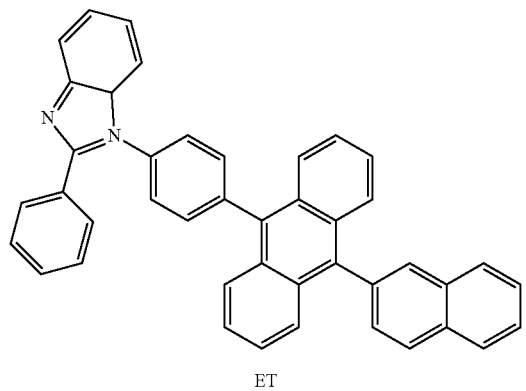

ET

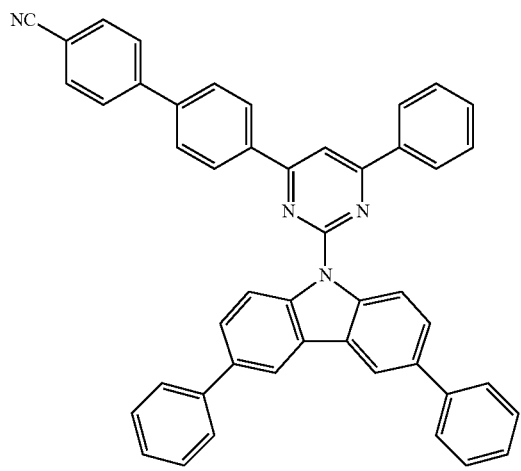

Compound H1

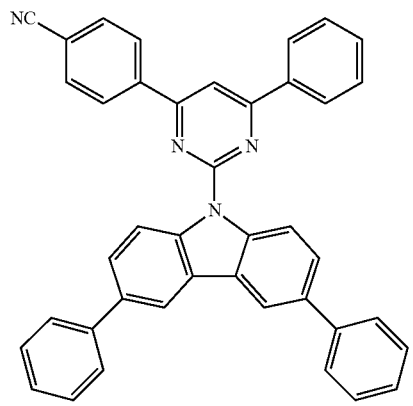

Compound H2

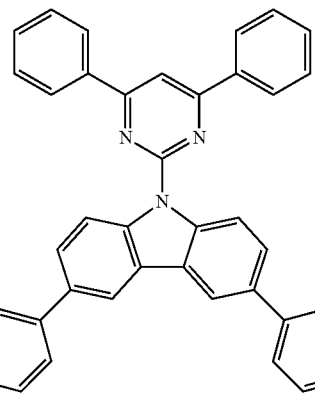

Compound F1

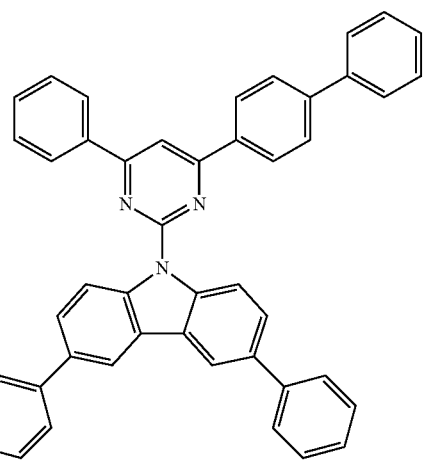

Compound F2

Example 2 and Comparative Examples 1 and 2

Organic EL devices were fabricated in the same manner as in Example 1, except that the emitting layer was formed using the compound in Table 1 instead of the host compound H1 of the emitting layer.

The device performance was evaluated in the same manner as in Example 1. The results are shown in Table 1.

TABLE 1

|  | Emitting layer Host material | 80% Life (hour) |
| --- | --- | --- |
| Example 1 | Compound H1 | 1000 |
| Example 2 | Compound H2 | 900 |
| Com. Example 1 | Compound F1 | 250 |
| Com. Example 2 | Compound F2 | 600 |

Table 1 shows that the organic EL devices of Examples 1 and 2 in which Compounds H1 and H2 containing a cyano group represented by the formula (I) are used as a host material for an emitting layer have a significantly longer life as compared with those of Comparative Examples 1 and 2 in which Compounds F1 and F2 having the same structure except for no cyano group are used as a host material.

INDUSTRIAL APPLICABILITY

The material for an organic EL device is useful for a material realizable of a phosphorescent organic EL device having long life.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the Japanese application specification claiming priority under the Paris Convention and the United State provisional application specification are incorporated herein by reference in its entirety.

The invention claimed is:

1. A material for an organic electroluminescence device represented by formula (I):

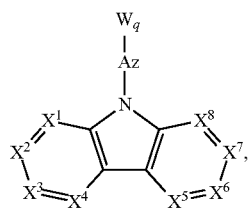

wherein, in the formula (I):
X$^1$ to X$^8$ are independently a nitrogen atom, CH, CHal or CR$^a$;
Hals are independently a halogen atom;
R$^a$s are independently a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted silyl group or a cyano group;
when plural Hals or plural R$^a$s are present, the plural Hals or the R$^a$s may be the same or different;
when two adjacent groups of X$^1$ to X$^5$ are CR$^a$, R$^a$s in the adjacent CR$^a$s may be bonded to each other to form a ring;
Az is a substituted or unsubstituted pyrimidine ring, a substituted or unsubstituted triazine ring, a substituted or unsubstituted quinazoline ring, or a substituted or unsubstituted 1,10-phenanthroline ring;
q is an integer of 1 to 4;
W is an aromatic hydrocarbon group having 6 to 30 ring carbon atoms which is substituted by at least one cyano group and may comprise a substituent that is not a cyano group, or an heterocyclic group having 5 to 30 ring atoms which is substituted by at least one cyano group and may comprise a substituent that is not a cyano group, wherein the substituent that is not a cyano group is one or more selected from the group consisting of an alkyl group having 1 to 20 carbon atoms, an alkoxy group having 1 to 20 carbon atoms, a haloalkyl group having 1 to 20 carbon atoms, a haloalkoxy group having 1 to 20 carbon atoms, an alkylsilyl group having 1 to 10 carbon atoms, an aryloxy group having 6 to 30 ring carbon atoms, an arylsilyl group having 6 to 30 carbon atoms, a dibenzofuran group, and a dibenzothiophene group; and,
when plural Ws are present, the plural Ws may be the same or different;
provided that the substituted or unsubstituted heterocyclic group having 5 to 30 ring atoms and the heterocyclic group having 5 to 30 ring atoms which is substituted by at least one cyano group and may comprise a substituent that is not a cyano group, are not a group represented by formula (A)

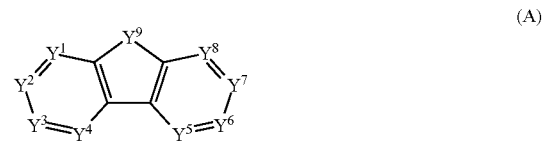

wherein, in formula (A):
Y$^1$ to Y$^8$ are the same as X$^1$ to X$^8$ in the formula (I), or a carbon atom which forms a single bond;
Y$^9$ is NH, NR$^c$, or a nitrogen atom which forms a single bond; and,
R$^c$ is a substituted or unsubstituted aromatic hydrocarbon group having 6 to 30 ring carbon atoms, a substituted or unsubstituted heterocyclic group having 5 to 30 ring atoms or a substituted or unsubstituted alkyl group having 1 to 30 carbon atoms.

2. The material for an organic electroluminescence device according to claim 1,
wherein, in formula (I), Az is a substituted or unsubstituted pyrimidine ring, a substituted or unsubstituted triazine ring, a substituted or unsubstituted quinazoline ring, or a substituted or unsubstituted 1,10-phenanthroline ring;
the substituent of pyrimidine ring, triazine ring, quinazoline ring, or 1,10-phenanthroline ring is one or more selected from the group consisting of a halogen atom, a substituted or unsubstituted aromatic hydrocarbon group having 6 to 30 ring carbon atoms, a substituted or unsubstituted heterocyclic group having 5 to 30 ring atoms, and a substituted or unsubstituted alkyl group having 1 to 30 carbon atoms;
when plural substituents are present, the plural substituents may be the same or different; and,
two adjacent substituents may be bonded to each other to form a ring;
provided that the heterocyclic group having 5 to 30 ring atoms is not a group represented by the formula (A), and further, the substituent of each of the above groups does not include the group represented by the formula (A).

3. The material for an organic electroluminescence device according to claim 1, wherein, in formula (I), Az is a substituted or unsubstituted pyrimidine ring, a substituted or unsubstituted triazine ring or a substituted or unsubstituted quinazoline ring.

4. The material for an organic electroluminescence device according to claim 1, wherein, in formula (I), W is a cyano-substituted phenyl group, a cyano-substituted biphenyl group, a cyano-substituted 9,9-diphenylfluorenyl group, a cyano-substituted 9,9'-spirobi[9H-fluorene]-2-yl group, a cyano-substituted 9,9-dimethylfluorenyl group, a cyano-substituted dibenzofuranyl group or a cyano-substituted dibenzothiophenyl group.

5. The material for an organic electroluminescence device according to claim 1, wherein, in formula (I), q is 1.

6. The material for an organic electroluminescence device according to claim 1, wherein, in formula (I), at least one of the X$^3$ and X$^6$ is CR$^a$, and the R$^a$s are independently a substituted or unsubstituted aromatic hydrocarbon group having 6 to 30 ring carbon atoms or a substituted or unsubstituted heterocyclic group having 5 to 30 ring atoms.

7. The material for an organic electroluminescence device according to claim 1, wherein, in formula (I), at least one of the $X^2$ and $X^7$ is $CR^a$, and the $R^a$s are independently a substituted or unsubstituted aromatic hydrocarbon group having 6 to 30 ring carbon atoms or a substituted or unsubstituted heterocyclic group having 5 to 30 ring atoms.

8. The material for an organic electroluminescence device according to claim 1, wherein, in formula (I), $R^a$ is selected from the group consisting of a substituted or unsubstituted phenyl group, a substituted or unsubstituted naphthyl group, a substituted or unsubstituted biphenyl group, a substituted or unsubstituted terphenyl group, a substituted or unsubstituted quaterphenyl group, a substituted or unsubstituted triphenylenyl group, a substituted or unsubstituted phenanthrenyl group, a substituted or unsubstituted fluorenyl group, a substituted or unsubstituted spirofluorenyl group, a substituted or unsubstituted 9,9-diphenylfluorenyl group, a substituted or unsubstituted 9,9'-spirobi[9H-fluorene]-2-yl group, a substituted or unsubstituted 9,9-dimethylfluorenyl group, a substituted or unsubstituted benzo[c]phenanthrenyl group, a substituted or unsubstituted benzo[a]triphenylenyl group, a substituted or unsubstituted naphtho[1,2-c]phenanthrenyl group, a substituted or unsubstituted naphtho[1,2-a]triphenylenyl group, a substituted or unsubstituted dibenzo[a,c]triphenylenyl group, a substituted or unsubstituted dibenzothiophene ring, a substituted or unsubstituted isoquinoline ring, a substituted or unsubstituted quinoxaline ring, a substituted or unsubstituted pyridine ring, a substituted or unsubstituted pyrazine ring, a substituted or unsubstituted pyrimidine ring, a substituted or unsubstituted pyridazine ring, a substituted or unsubstituted triazine ring, a substituted or unsubstituted quinoline ring, a substituted or unsubstituted dibenzofuran ring, a substituted or unsubstituted benzo[c]dibenzofuran ring, a substituted or unsubstituted alkyl group having 1 to 30 carbon atoms, a substituted or unsubstituted silyl group and a cyano group.

9. The material for an organic electroluminescence device according to claim 2, wherein, in formula (I), Az is a substituted or unsubstituted pyrimidine ring, a substituted or unsubstituted triazine ring, a substituted or unsubstituted quinazoline ring, or a substituted or unsubstituted 1,10-phenanthroline ring, the substituent of pyrimidine ring, triazine ring, quinazoline ring, or 1,10-phenanthroline ring is one or more selected from the group consisting of a substituted or unsubstituted phenyl group, a substituted or unsubstituted naphthyl group, a substituted or unsubstituted biphenyl group, a substituted or unsubstituted terphenyl group, a substituted or unsubstituted quaterphenyl group, a substituted or unsubstituted triphenylenyl group, a substituted or unsubstituted phenanthrenyl group, a substituted or unsubstituted fluorenyl group, a substituted or unsubstituted spirofluorenyl group, a substituted or unsubstituted 9,9-diphenylfluorenyl group, a substituted or unsubstituted 9,9'-spirobi[9H-fluorene]-2-yl group, a substituted or unsubstituted 9,9-dimethylfluorenyl group, a substituted or unsubstituted benzo[c]phenanthrenyl group, a substituted or unsubstituted benzo[a]triphenylenyl group, a substituted or unsubstituted naphtho[1,2-c]phenanthrenyl group, a substituted or unsubstituted naphtho[1,2-a]triphenylenyl group, a substituted or unsubstituted dibenzo[a,c]triphenylenyl group, a substituted or unsubstituted dibenzothiophene ring, a substituted or unsubstituted isoquinoline ring, a substituted or unsubstituted quinoxaline ring, a substituted or unsubstituted pyridine ring, a substituted or unsubstituted pyrazine ring, a substituted or unsubstituted pyrimidine ring, a substituted or unsubstituted pyridazine ring, a substituted or unsubstituted triazine ring, a substituted or unsubstituted quinoline ring, a substituted or unsubstituted dibenzofuran ring, a substituted or unsubstituted benzo[c]dibenzofuran ring and a substituted or unsubstituted alkyl group having 1 to 30 carbon atoms.

10. An organic electroluminescence device comprising:

an anode, a cathode, and one or more organic thin film layers including an emitting layer between the cathode and the anode, wherein at least one of the organic thin film layers comprises the material for an organic electroluminescence device according to claim 1.

11. The organic electroluminescence device according to claim 10, wherein the emitting layer comprises the material for an organic electroluminescence device.

12. The organic electroluminescence device according to claim 10, wherein the emitting layer comprises a phosphorescent material, and the phosphorescent material is an ortho-metalized complex of a metal atom selected from iridium (Ir), osmium (Os) and platinum (Pt).

13. The material for an organic electroluminescence device according to claim 1, which is represented by one of the following formulae:

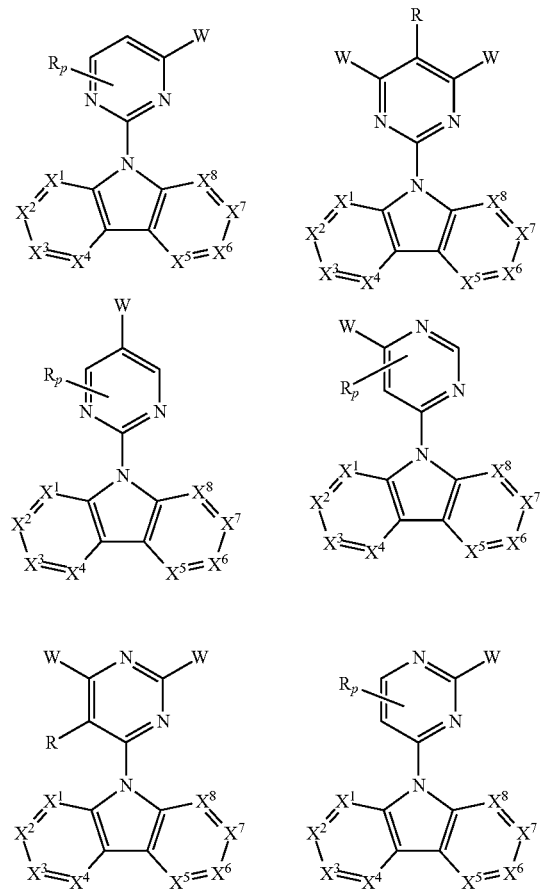

-continued

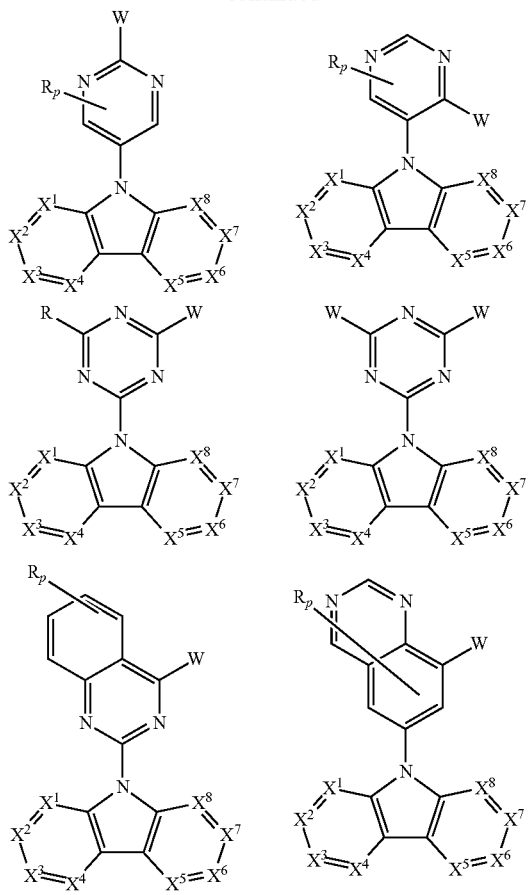

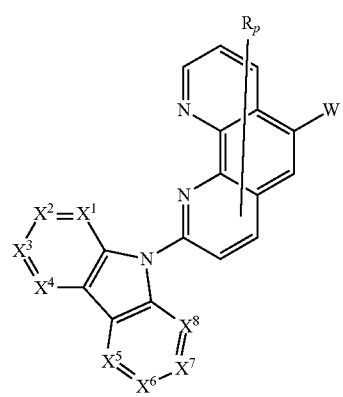

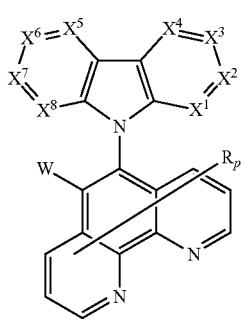

-continued

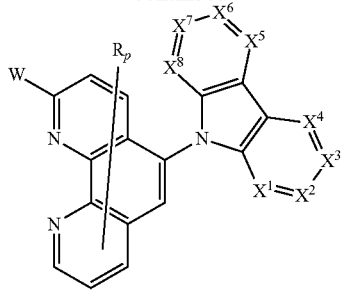

wherein in the formulae:
R is independently a halogen atom, a substituted or unsubstituted aromatic hydrocarbon group having 6 to 30 ring carbon atoms, a substituted or unsubstituted heterocyclic group having 5 to 30 ring atoms or a substituted or unsubstituted alkyl group having 1 to 30 carbon atoms;
in the case of plural Rs, the plural Rs may be the same as or different from each other;
p is an integer of 1 to 6; and
$X^1$ to $X^8$ and W are as defined in the formula (I).

14. The material for an organic electroluminescence device according to claim 13, wherein, in the formulae, R is selected from the group consisting of a substituted or unsubstituted phenyl group, a substituted or unsubstituted naphthyl group, a substituted or unsubstituted biphenyl group, a substituted or unsubstituted terphenyl group, a substituted or unsubstituted quaterphenyl group, a substituted or unsubstituted triphenylenyl group, a substituted or unsubstituted phenanthrenyl group, a substituted or unsubstituted fluorenyl group, a substituted or unsubstituted spirofluorenyl group, a substituted or unsubstituted 9,9-diphenylfluorenyl group, a substituted or unsubstituted 9,9'-spirobi[9H-fluorene]-2-yl group, a substituted or unsubstituted 9,9-dimethylfluorenyl group, a substituted or unsubstituted benzo[c]phenanthrenyl group, a substituted or unsubstituted benzo[a]triphenylenyl group, a substituted or unsubstituted naphtho[1,2-c]phenanthrenyl group, a substituted or unsubstituted naphtho[1,2-a]triphenylenyl group, a substituted or unsubstituted dibenzo[a,c]triphenylenyl group, a substituted or unsubstituted dibenzothiophene ring, a substituted or unsubstituted isoquinoline ring, a substituted or unsubstituted quinoxaline ring, a substituted or unsubstituted pyridine ring, a substituted or unsubstituted pyrazine ring, a substituted or unsubstituted pyrimidine ring, a substituted or unsubstituted pyridazine ring, a substituted or unsubstituted triazine ring, a substituted or unsubstituted quinoline ring, a substituted or unsubstituted dibenzofuran ring, a substituted or unsubstituted benzo[c]dibenzofuran ring, and a substituted or unsubstituted alkyl group having 1 to 30 carbon atoms; and
in the case of plural Rs, the plural Rs may be the same as or different from each other.

15. The material for an organic electroluminescence device according to claim 1, which is represented by formula (I'):

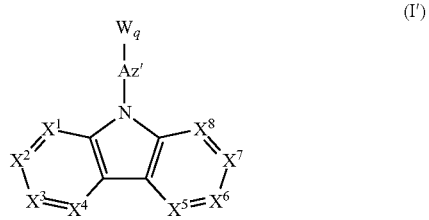

(I')

wherein in formula (I'):

Az' is a substituted or unsubstituted pyrimidine ring; and $X^1$ to $X^8$, q, and W are as defined in formula (I).

16. The material for an organic electroluminescence device according to claim 1, wherein, in formula (I), $X^1$ to $X^8$ are independently CH, CHal, or $CR^a$.

17. The material for an organic electroluminescence device according to claim 1, wherein, in formula (I), W is the heterocyclic group having 5 to 30 ring atoms and the heterocyclic group is a pyrrol ring, a isoindole ring, a benzofuran ring, an isobenzofuran ring, a dibenzothiophene ring, an isoquinoline ring, a quinoxaline ring, a phenanthridine ring, a phenanthroline ring, a pyridine ring, a pyrazine ring, a pyrimidine ring, a pyridazine ring, a triazine ring, an indole ring, a quinoline ring, an acridine ring, a pyrrolidine ring, a dioxane ring, a piperidine ring, a morpholine ring, a piperazine ring, a furan ring, a thiophene ring, an oxazole ring, an oxadiazole ring, a benzoxazole ring, a thiazole ring, a thiadiazole ring, a benzothiazole ring, a triazole ring, an imidazole ring, a benzimidazole ring, a pyran ring, a dibenzofuran ring, or a benzo[c] dibenzofuran ring.

\* \* \* \* \*